(12) United States Patent
Gregorich et al.

(10) Patent No.: US 8,070,792 B2
(45) Date of Patent: Dec. 6, 2011

(54) STENT

(75) Inventors: Daniel Gregorich, New Brighton, MN (US); Timothy S. Girton, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1988 days.

(21) Appl. No.: 10/063,179

(22) Filed: Mar. 28, 2002

(65) Prior Publication Data

US 2002/0095208 A1    Jul. 18, 2002

Related U.S. Application Data

(63) Continuation-in-part of application No. 10/042,634, filed on Jan. 9, 2002, now abandoned, which is a continuation-in-part of application No. 09/957,983, filed on Sep. 21, 2001, now Pat. No. 6,896,696.

(60) Provisional application No. 60/234,548, filed on Sep. 22, 2000, provisional application No. 60/272,906, filed on Mar. 1, 2001, provisional application No. 60/272,651, filed on Mar. 1, 2001.

(51) Int. Cl.
*A61F 29/00* (2006.01)
*A61M 29/00* (2006.01)

(52) U.S. Cl. .................................................... 623/1.15

(58) Field of Classification Search ........ 623/1.11–1.22; 606/108, 198, 191, 194, 195
See application file for complete search history.

(56) References Cited

U.S. PATENT DOCUMENTS

| | | | |
|---|---|---|---|
| 2,836,181 A | 5/1958 | Tapp | 128/334 |
| 3,105,492 A | 10/1963 | Jeckel | 128/334 |
| 3,272,204 A | 9/1966 | Artandi et al. | 128/334 |
| 3,490,975 A | 1/1970 | Lightwood et al. | 156/167 |
| 3,509,883 A | 5/1970 | Dibelius | 128/348 |
| 3,526,228 A | 9/1970 | Lyng | 128/334 |
| 3,562,820 A | 2/1971 | Braun | 3/1 |
| 3,635,215 A | 1/1972 | Shea et al. | 128/130 |
| 3,657,744 A | 4/1972 | Ersek | 3/1 |
| 3,771,526 A | 11/1973 | Rudie | 128/334 |
| 3,868,956 A | 3/1975 | Alfidi | 128/345 |
| 3,993,078 A | 11/1976 | Bergentz | 128/334 R |
| 4,078,167 A | 3/1978 | Banas et al. | 219/121 |
| 4,127,761 A | 11/1978 | Pauley et al. | 219/121 L |
| 4,140,126 A | 2/1979 | Choudhury | 128/325 |
| 4,141,364 A | 2/1979 | Schultze | 128/349 B |
| 4,214,587 A | 7/1980 | Sakura, Jr. | 128/334 R |

(Continued)

FOREIGN PATENT DOCUMENTS

DE    297 01 758    5/1997

(Continued)

OTHER PUBLICATIONS

SMART™ *Stent* Brochure, Cordis, a Johnson & Johnson company, date unknown.

(Continued)

*Primary Examiner* — Vy Q Bui
(74) *Attorney, Agent, or Firm* — Vidas, Arrett & Steinkraus, P.A.

(57) ABSTRACT

A stent comprises a plurality of circumferential bands. Circumferential bands which are adjacent one another are connected one to the other. The circumferential bands include peaks and troughs interconnected by bent struts. The bands may overlap or may be connected by connectors.

6 Claims, 46 Drawing Sheets

U.S. PATENT DOCUMENTS

| | | | | |
|---|---|---|---|---|
| 4,300,244 A | 11/1981 | Bokros | | 3/1.4 |
| 4,313,231 A | 2/1982 | Koyamada | | 3/1.4 |
| 4,319,363 A | 3/1982 | Ketharanathan | | 3/1.4 |
| 4,413,629 A | 11/1983 | Durley, III | | |
| 4,425,908 A | 1/1984 | Simon | | 128/1 R |
| 4,441,215 A | 4/1984 | Kaster | | 3/1.4 |
| 4,470,407 A | 9/1984 | Hussein | | 128/6 |
| 4,501,264 A | 2/1985 | Rockey | | 128/1 R |
| 4,503,569 A | 3/1985 | Dotter | | 3/1.4 |
| 4,512,338 A | 4/1985 | Balko et al. | | 128/1 R |
| 4,535,770 A | 8/1985 | Lemole | | 128/327 |
| 4,550,447 A | 11/1985 | Seiler, Jr. et al. | | 623/1 |
| 4,553,545 A | 11/1985 | Maass et al. | | 128/341 |
| 4,560,374 A | 12/1985 | Hammerslag | | 604/49 |
| 4,580,568 A | 4/1986 | Gianturco | | 128/345 |
| 4,597,389 A | 7/1986 | Ibrahim et al. | | 128/328 |
| 4,647,416 A | 3/1987 | Seiler, Jr. et al. | | 264/118 |
| 4,649,922 A | 3/1987 | Wiktor | | 128/344 |
| 4,655,771 A | 4/1987 | Wallsten | | 623/1 |
| 4,655,776 A | 4/1987 | Lesinski | | 623/10 |
| 4,665,918 A | 5/1987 | Garza et al. | | 128/343 |
| 4,681,110 A | 7/1987 | Wiktor | | 128/343 |
| 4,693,721 A | 9/1987 | Ducheyne | | 623/16 |
| 4,733,665 A | 3/1988 | Palmaz | | 128/343 |
| 4,739,762 A | 4/1988 | Palmaz | | 128/343 |
| 4,740,207 A | 4/1988 | Kreamer | | 623/1 |
| 4,760,849 A | 8/1988 | Kropf | | 128/341 |
| 4,762,128 A | 8/1988 | Rosenbluth | | 128/343 |
| 4,769,029 A | 9/1988 | Patel | | 623/1 |
| 4,771,773 A | 9/1988 | Kropf | | 128/303 R |
| 4,776,337 A | 10/1988 | Palmaz | | 128/343 |
| 4,786,507 A | 11/1988 | Schmidt | | 424/472 |
| 4,787,899 A | 11/1988 | Lazarus | | 623/1 |
| 4,795,458 A | 1/1989 | Regan | | 623/1 |
| 4,795,465 A | 1/1989 | Marten | | 623/9 |
| 4,800,882 A | 1/1989 | Gianturco | | 128/343 |
| 4,820,298 A | 4/1989 | Leveen et al. | | 623/1 |
| 4,830,003 A | 5/1989 | Wolff et al. | | 128/343 |
| 4,842,575 A | 6/1989 | Hoffman, Jr. et al. | | 600/36 |
| 4,848,343 A | 7/1989 | Wallsten et al. | | 128/343 |
| 4,851,009 A | 7/1989 | Pinchuk | | 623/66 |
| 4,856,516 A | 8/1989 | Hillstead | | 128/343 |
| 4,872,874 A | 10/1989 | Taheri | | 623/1 |
| 4,877,030 A | 10/1989 | Beck et al. | | 128/343 |
| 4,878,906 A | 11/1989 | Lindemann et al. | | 623/1 |
| 4,886,062 A | 12/1989 | Wiktor | | 128/343 |
| 4,913,141 A | 4/1990 | Hillstead | | 606/108 |
| 4,922,905 A | 5/1990 | Strecker | | 606/195 |
| 4,950,227 A | 8/1990 | Savin et al. | | 604/8 |
| 4,950,258 A | 8/1990 | Kawai et al. | | 604/281 |
| 4,994,071 A | 2/1991 | MacGregor | | 606/194 |
| 5,015,253 A | 5/1991 | MacGregor | | 623/1 |
| 5,019,090 A | 5/1991 | Pinchuk | | 606/194 |
| 5,035,706 A | 7/1991 | Giantureo et al. | | 606/198 |
| 5,037,392 A | 8/1991 | Hillstead | | 604/96 |
| 5,059,211 A | 10/1991 | Stack et al. | | 606/198 |
| 5,064,435 A | 11/1991 | Porter | | 623/12 |
| 5,091,205 A | 2/1992 | Fan | | 427/2 |
| 5,092,877 A | 3/1992 | Pinchuk | | 623/1 |
| 5,102,417 A | 4/1992 | Palmaz | | 606/195 |
| 5,104,399 A | 4/1992 | Lazarus | | 623/1 |
| 5,104,404 A | 4/1992 | Wolff | | 623/1 |
| 5,108,415 A | 4/1992 | Pinchuk et al. | | 606/194 |
| 5,108,417 A | 4/1992 | Sawyer | | 606/198 |
| 5,122,154 A | 6/1992 | Rhodes | | 600/198 |
| 5,133,732 A | 7/1992 | Wiktor | | 605/195 |
| 5,135,536 A | 8/1992 | Hillstead | | 606/195 |
| 5,139,480 A | 8/1992 | Hickle et al. | | 606/8 |
| 5,147,385 A | 9/1992 | Beck et al. | | 623/1 |
| 5,147,400 A | 9/1992 | Kaplan et al. | | 623/13 |
| 5,158,548 A | 10/1992 | Lau et al. | | 604/96 |
| 5,163,952 A | 11/1992 | Froix | | 623/1 |
| 5,195,984 A | 3/1993 | Schatz | | 606/195 |
| 5,197,978 A | 3/1993 | Hess | | 623/1 |
| 5,217,483 A | 6/1993 | Tower | | 606/198 |
| 5,226,913 A | 7/1993 | Pinchuk | | 623/1 |
| 5,282,823 A | 2/1994 | Schwartz et al. | | 606/198 |
| 5,282,824 A | 2/1994 | Gianturco | | 606/198 |
| 5,292,331 A | 3/1994 | Boneau | | 606/198 |
| 5,304,200 A | 4/1994 | Spaulding | | 606/198 |
| 5,344,425 A | 9/1994 | Sawyer | | 606/198 |
| 5,354,308 A | 10/1994 | Simon et al. | | 606/198 |
| 5,354,309 A | 10/1994 | Schnepp-Pesch et al. | | 606/198 |
| 5,383,892 A | 1/1995 | Cardon et al. | | 606/198 |
| 5,405,377 A | 4/1995 | Cragg | | 623/1 |
| 5,449,373 A | 9/1995 | Pinchasik et al. | | 606/198 |
| 5,465,011 A | 11/1995 | Miller et al. | | |
| 5,569,295 A | 10/1996 | Lam | | 606/198 |
| 5,591,197 A | 1/1997 | Orth et al. | | 606/198 |
| 5,697,971 A | 12/1997 | Fischell et al. | | 623/1 |
| 5,718,713 A | 2/1998 | Frantzen | | 606/198 |
| 5,722,412 A | 3/1998 | Pflugrath et al. | | |
| 5,735,893 A | 4/1998 | Lau et al. | | 623/1 |
| 5,741,327 A | 4/1998 | Frantzen | | 623/1 |
| 5,755,770 A | 5/1998 | Ravenscroft | | 623/1 |
| 5,755,776 A | 5/1998 | Al-Saadon | | 623/1 |
| 5,755,781 A | 5/1998 | Jayaraman | | 623/1 |
| 5,776,161 A | 7/1998 | Globerman | | 606/194 |
| 5,776,183 A | 7/1998 | Kanesaka et al. | | 623/1 |
| 5,800,521 A | 9/1998 | Orth | | 623/1 |
| 5,807,404 A | 9/1998 | Richter | | 623/1 |
| 5,810,872 A | 9/1998 | Kanesaka et al. | | 606/198 |
| 5,824,046 A | 10/1998 | Smith et al. | | 623/1 |
| 5,824,059 A | 10/1998 | Wijay | | 623/1 |
| 5,836,966 A | 11/1998 | St. Germain | | 606/198 |
| 5,876,449 A | 3/1999 | Starck et al. | | 623/12 |
| 5,886,062 A | 3/1999 | Dietrich et al. | | 521/167 |
| 5,893,363 A | 4/1999 | Little et al. | | |
| 5,895,406 A | 4/1999 | Gray et al. | | 606/198 |
| 5,911,754 A | 6/1999 | Kanesaka et al. | | 623/1 |
| 5,913,895 A | 6/1999 | Burpee et al. | | 623/1 |
| 5,916,263 A | 6/1999 | Goicoechea et al. | | 623/1 |
| 5,922,021 A | 7/1999 | Jang | | 623/1 |
| 5,938,682 A | 8/1999 | Hojeibane et al. | | 606/198 |
| 5,938,697 A | 8/1999 | Killion et al. | | 623/1 |
| 5,948,016 A | 9/1999 | Jang | | 623/1 |
| 5,954,743 A | 9/1999 | Jang | | 606/198 |
| 5,957,930 A | 9/1999 | Vrba | | 606/108 |
| 5,980,553 A | 11/1999 | Gray et al. | | |
| 6,017,365 A | 1/2000 | Von Oepen | | 623/1 |
| 6,068,656 A | 5/2000 | Von Oepen | | 623/1.17 |
| 6,113,627 A | 9/2000 | Jang | | 623/1 |
| 6,120,522 A | 9/2000 | Vrba et al. | | 606/190 |
| 6,123,712 A | 9/2000 | Di Caprio et al. | | 606/108 |
| 6,123,721 A | 9/2000 | Jang | | 623/1 |
| 6,129,755 A | 10/2000 | Mathis et al. | | 623/1.15 |
| 6,179,868 B1 | 1/2001 | Burpee et al. | | 623/1.17 |
| 6,193,747 B1 | 2/2001 | Von Oepen | | 623/1.15 |
| 6,200,334 B1 | 3/2001 | Jang | | 623/1.1 |
| 6,235,053 B1 | 5/2001 | Jang | | 623/1.15 |
| 6,331,189 B1 | 12/2001 | Wolinsky et al. | | 623/1.15 |
| 6,352,552 B1 | 3/2002 | Levinson et al. | | 623/1.15 |
| 6,375,677 B1 | 4/2002 | Penn et al. | | 623/1.16 |
| 6,398,805 B1 | 6/2002 | Alt | | 623/1.15 |
| 6,602,285 B1 | 8/2003 | Von Oepen et al. | | 623/1.17 |
| 6,679,911 B2* | 1/2004 | Burgermeister | | 623/1.17 |
| 6,682,554 B2 | 1/2004 | Oepen et al. | | 623/1.15 |
| 6,755,856 B2 | 6/2004 | Fierens et al. | | 623/1.15 |
| 6,887,264 B2* | 5/2005 | Penn et al. | | 623/1.15 |
| 6,896,696 B2* | 5/2005 | Doran et al. | | 623/1.15 |
| 7,179,285 B2 | 2/2007 | Ikeuchi et al. | | 623/1.15 |
| 2001/0020183 A1 | 9/2001 | Jang | | 623/1.15 |
| 2002/0007211 A1 | 1/2002 | Pinchasik et al. | | 623/1.16 |
| 2002/0007212 A1 | 1/2002 | Brown et al. | | 623/1.16 |
| 2002/0019660 A1 | 2/2002 | Gianotti et al. | | 623/1.15 |

FOREIGN PATENT DOCUMENTS

| | | |
|---|---|---|
| DE | 297 02 671 | 5/1997 |
| DE | 297 08 689 | 8/1997 |
| DE | 297 08 879 U1 | 9/1997 |
| DE | 297 16 476 U1 | 2/1998 |
| DE | 298 16 878 | 2/1999 |
| DE | 198 34 956 | 5/1999 |
| EP | 0 364 787 B1 | 4/1990 |
| EP | 0 540 290 B1 | 5/1993 |
| EP | 0 541 443 B1 | 5/1993 |
| EP | 0 606 165 A1 | 7/1994 |

| | | |
|---|---|---|
| EP | 0 734 698 | 10/1996 |
| EP | 0 800 800 | 10/1997 |
| EP | 0 821 920 B1 | 2/1998 |
| EP | 0 876 806 A1 | 11/1998 |
| EP | 1 093 771 A2 | 4/2001 |
| WO | 94/17754 | 8/1994 |
| WO | 96/21404 | 7/1996 |
| WO | 96/26689 | 9/1996 |
| WO | 97/04721 | 2/1997 |
| WO | 97/14375 | 4/1997 |
| WO | 97/25937 | 7/1997 |
| WO | 97/32543 | 9/1997 |
| WO | 97/32544 | 9/1997 |
| WO | 97/33534 | 9/1997 |
| WO | 97/40780 | 11/1997 |
| WO | 97/40781 | 11/1997 |
| WO | 97/40782 | 11/1997 |
| WO | 97/40783 | 11/1997 |
| WO | 97/40874 | 11/1997 |
| WO | 98/20810 | 5/1998 |
| WO | 98/40035 | 9/1998 |
| WO | 99/40876 | 8/1999 |
| WO | WO99/39660 | 12/1999 |
| WO | 00/13611 | 3/2000 |
| WO | 00/30563 | 6/2000 |
| WO | 00/42946 A1 | 7/2000 |
| WO | 00/69366 | 11/2000 |
| WO | 01/01885 | 1/2001 |
| WO | 01/26583 | 4/2001 |
| WO | 01/32099 | 5/2001 |
| WO | 01/32102 | 5/2001 |
| WO | 02/060344 | 8/2002 |
| WO | PCT/US02/13386 | * 11/2003 |

OTHER PUBLICATIONS

Beyar et al., "The BeStent; The Parallel-Serial Jang Stents", *Handbook of Coronary Stents, Second Edition*, 158-171 & 229-234 (1998).

Beyar et al., "Newer Stents: Materials and Designs", *IAGS Proceedings*, 9(5): 363-371 (Jun. 1997).

Roguin et al., Acute and 30-Day Results of the Serpentine Balloon Expandable Stent Implantation in Simple and Complex Coronary Arterial Narrowings:, *The American Journal of Cardiology*, 80:1155-1162 (Nov. 1997).

Roguin et al., "beStent-the serpentine balloon expandable stent: review of mechanical properties and clinical experience", *Artif Organs*, 22(3):243-249 (Mar. 1998).

*Manufacturing Processes for Engineering Materials*, by Serope Kalpakjian, Illinois Institute of Technology, Addison-Wesley Publishing Company, pp. 340.

A View of Vascular Stents, by Richard A. Schartz, MD, from the Arizona Heart Institute Foundation, Phoenix, Arizona, *CIRCULATION*, vol. 79, No. 2, Feb. 1989, pp. 445-457.

The Self-Expanding Mesh Stent, by Ulrich Sigwart, *SECTION IV*, Chapter 29, pp. 605-610.

Brochure Entitled Micro Stent™, by Applied Vascular Engineering, Inc.

Engineering Fluid Mechanics, *Third Edition*, John A. Robertson and Clayton T. Crowe, pp. 94 and pp. 414-421.

*Cambridge Dictionary of Science and Technology*, Cambridge University Pressp. 128.

Improved Dilation Catheter Balloons, by Stanley B. Levy, Ph.D., *Journal of Clinical Engineering*, vol. 11, No. 4, Jul.-Aug. 1986, pp. 291-296.

Self-expanding Stainless Steel Biliary Stents, by Harold G. Coons, MD, *RADIOLOGY 1989*, vol. 170, No. 3, Part 2, pp. 979-983.

Technical Note Entitled Modifications of Gianturco Expandable Wire Stents, by Barry T. Uchida et al., *AJR*, vol. 150, May 1988, pp. 1185-1187.

Brochure from Cook Incorporated regarding Gianturco-Rosch Biliary Z-Stents.

Expandable Biliary Endoprothesis: An Experimental Study, By Carrasco et al., *AJR*, vol. 145, Dec. 1985, pp. 1279-1282.

Gianturco Expandable Metallic Biliary Stents: Results of a European Clinical Trial, by Irving et al., *Interventional Radiology*, vol. 172, No. 2, Aug. 1989, pp. 309-312.

Tracheobronchial Tree: Expandable Metallic Stents Used in Experimental and Clinical Application, Work In Progress, by Wallace et al., *RADIOLOGY*, Feb. 1986, pp. 309-312.

Brochure Entitled AVE Micro Stent™, Instructions for Use, by Applied Vascular Engineering, Inc., pp. 1-15.

U.S. Appl. No. 60/238,178, filed Oct. 5, 2000, DiCaprio et al.
U.S. Appl. No. 10/042,634, filed Jan. 9, 2002.
U.S. Appl. No. 09/957,983, filed Sep. 21, 2001.
U.S. Appl. No. 60/234,548, filed Sep. 22, 2000.
U.S. Appl. No. 60/272,906, filed Mar. 1, 2001.
U.S. Appl. No. 60/272,651, filed Mar. 1, 2001.
PCT International Search Report, PCT/US02/13386 dated Nov. 3, 2003.

* cited by examiner

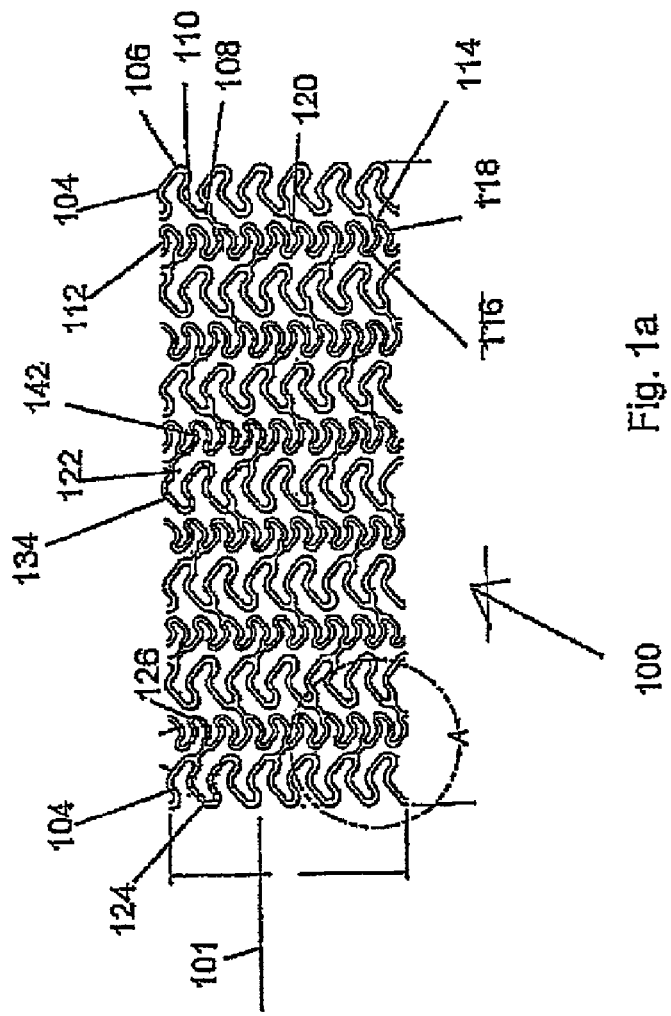
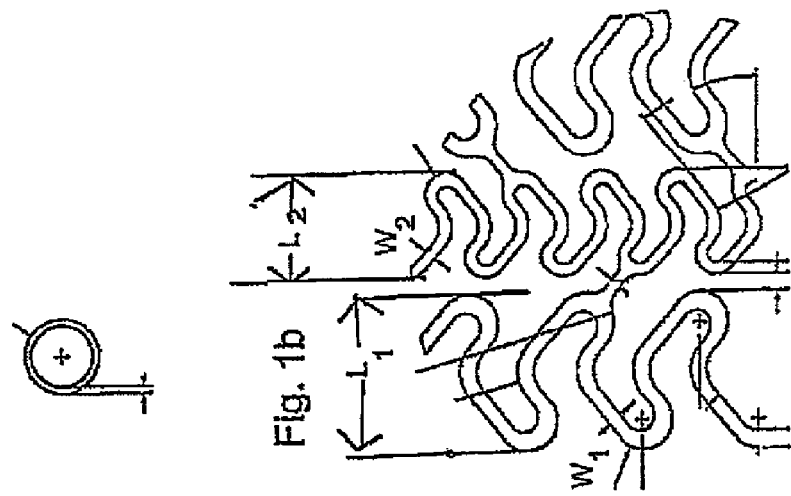

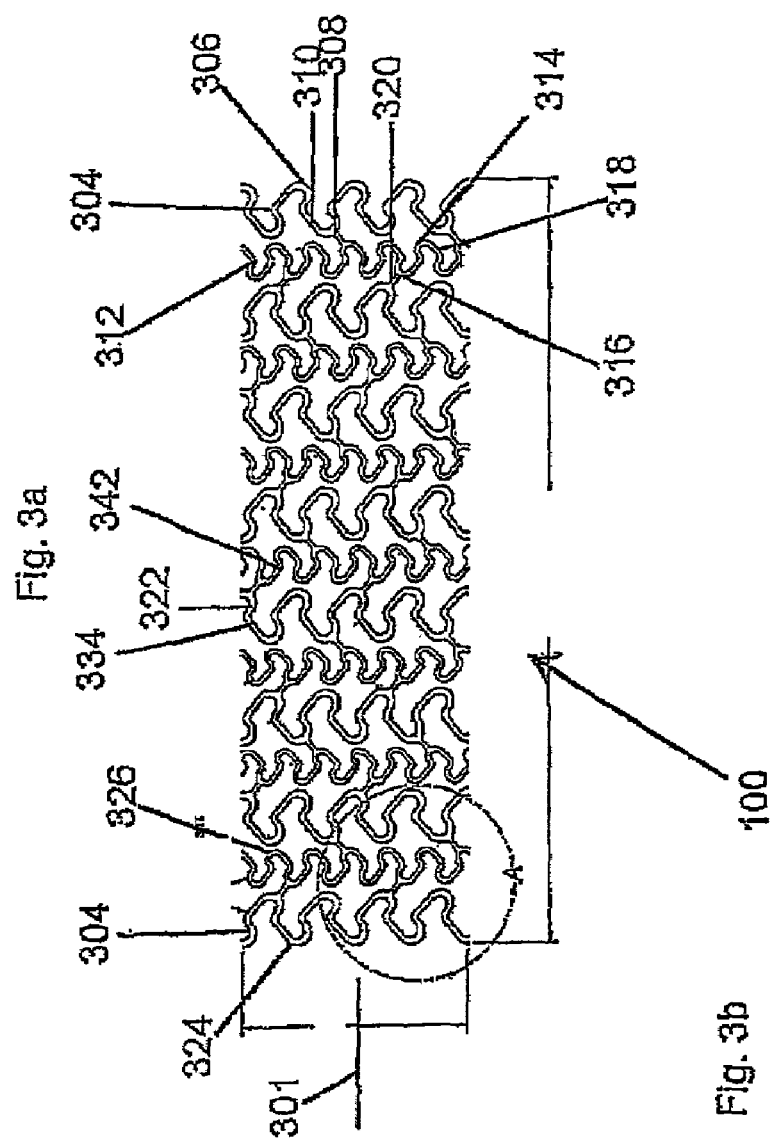
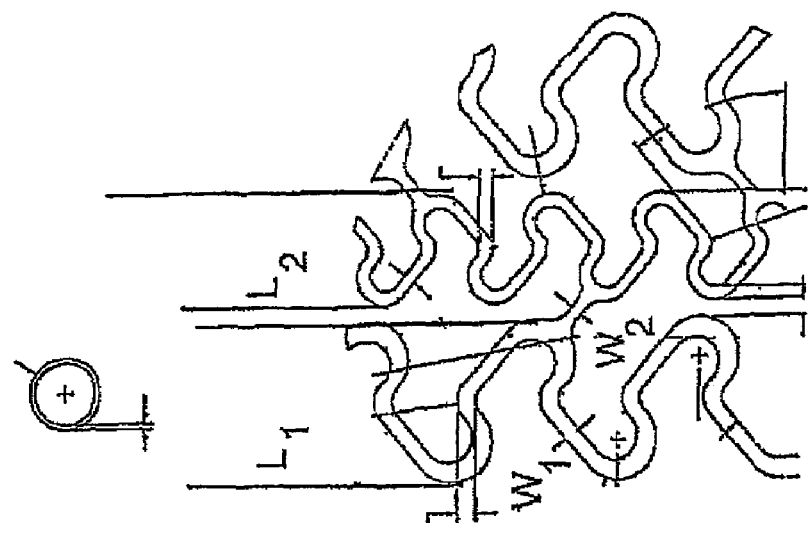
Fig. 3a
Fig. 3b

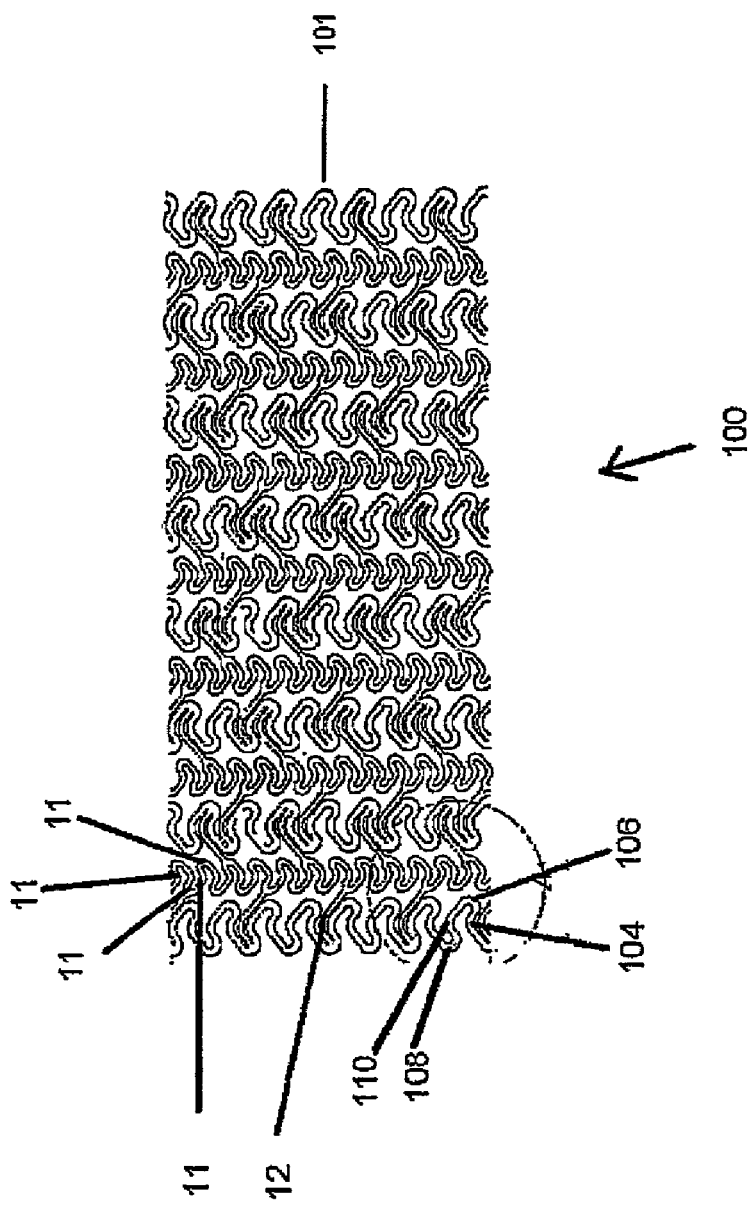
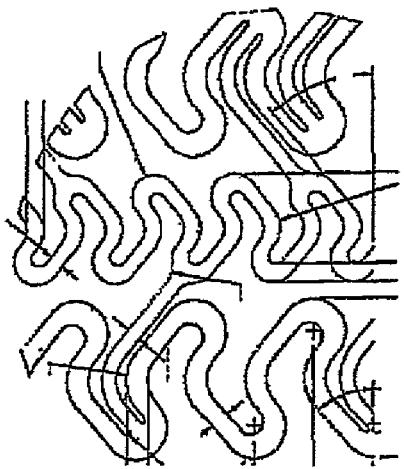
Fig. 12
DETAIL A

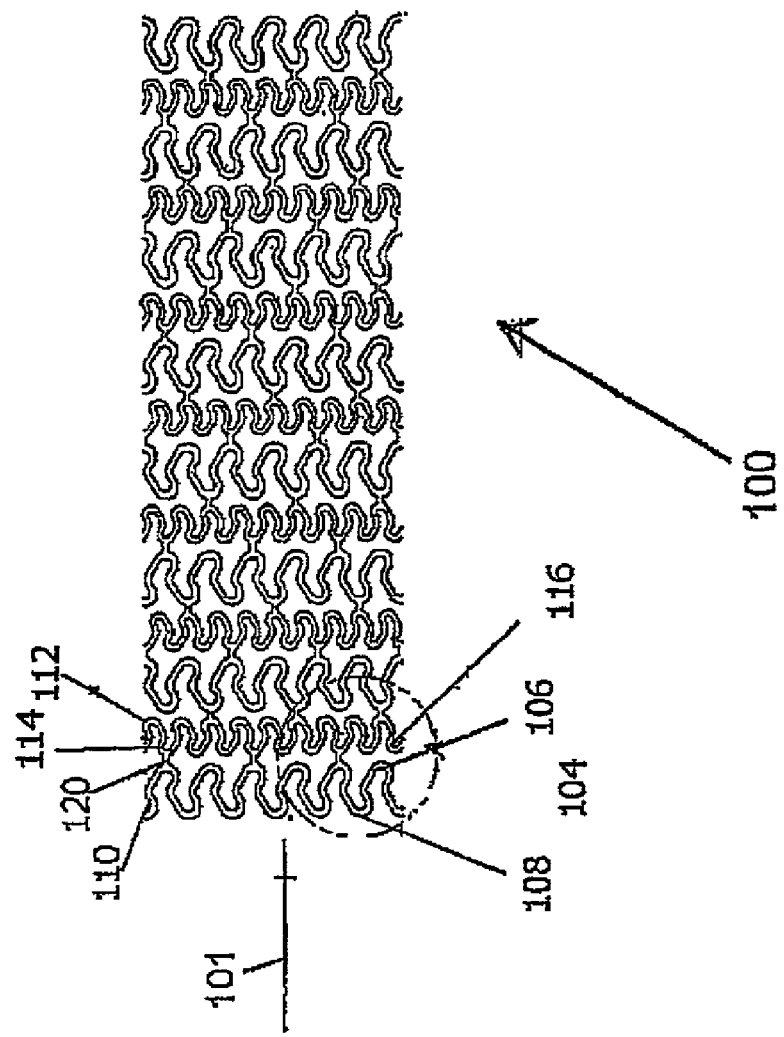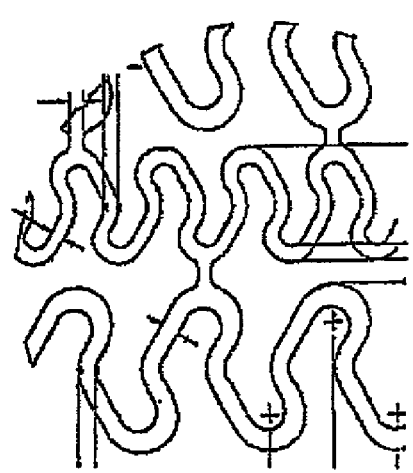
Fig. 13
DETAIL A

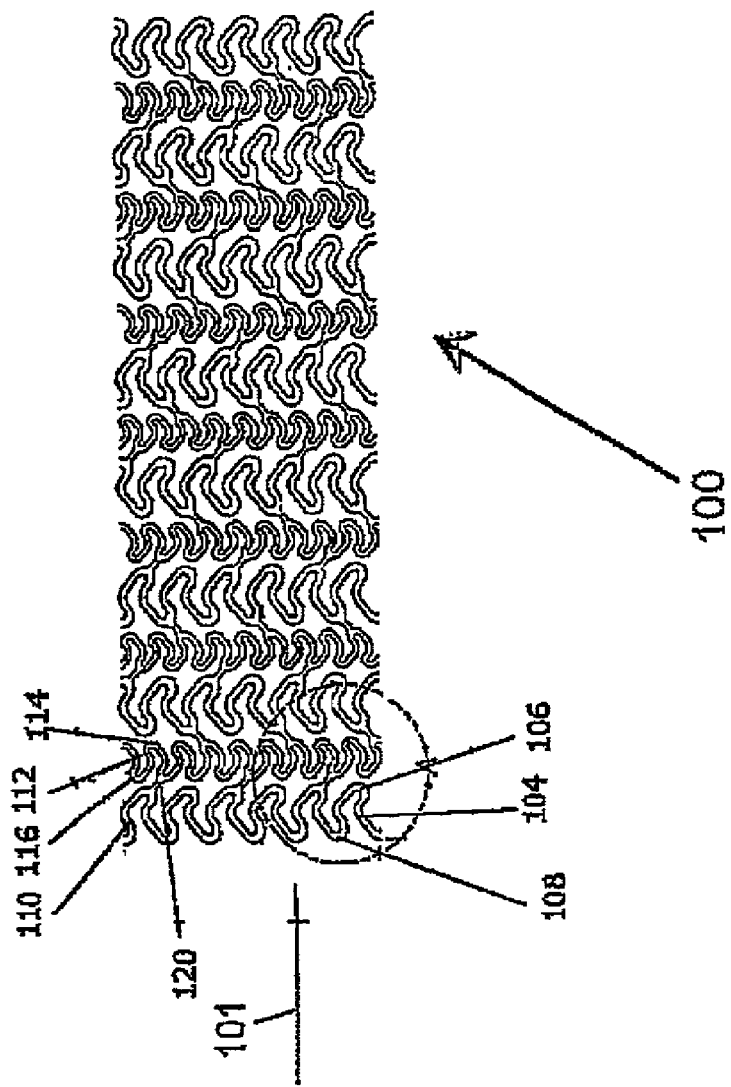
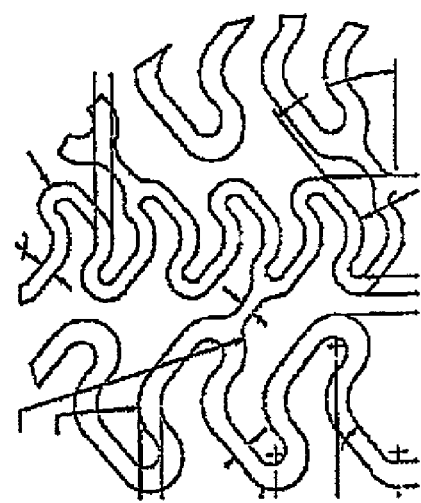
Fig. 14
DETAIL A

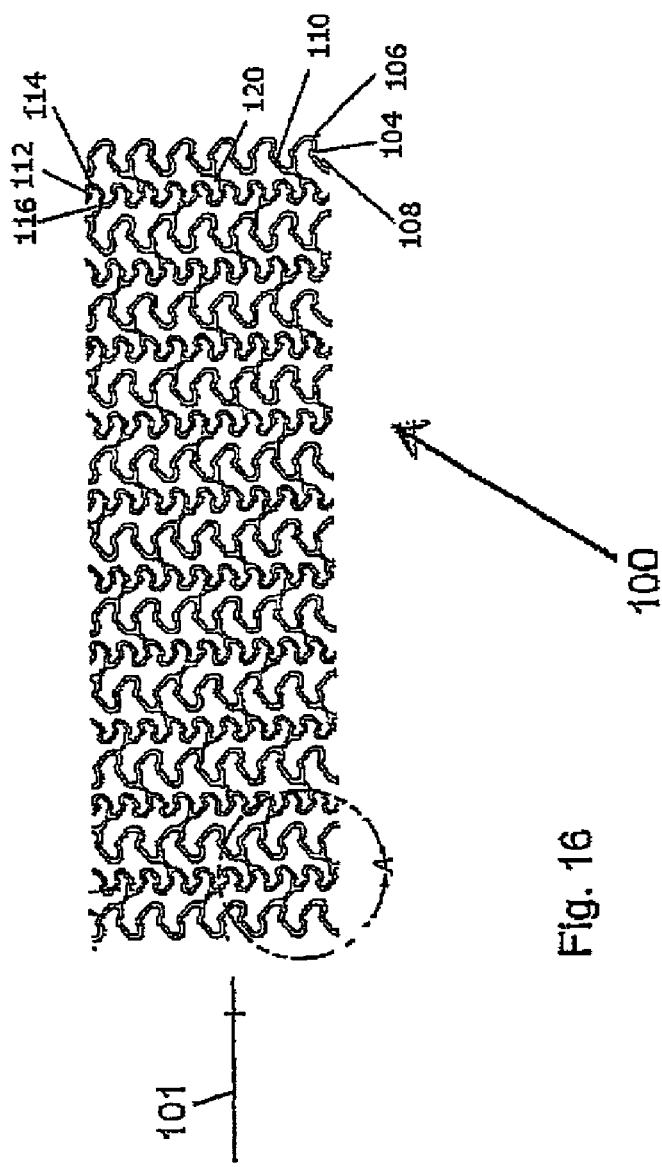
Fig. 16
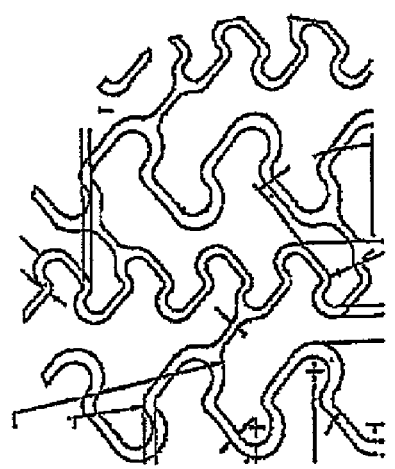
DETAIL A

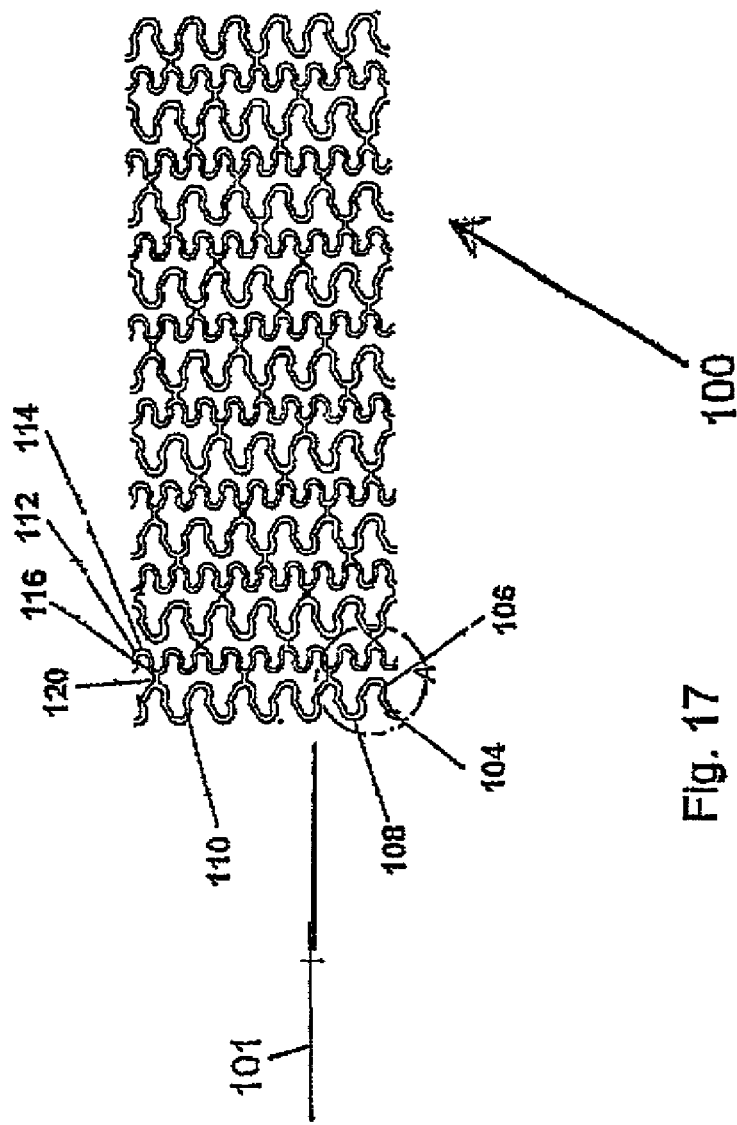
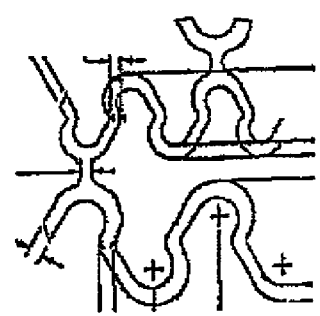
Fig. 17

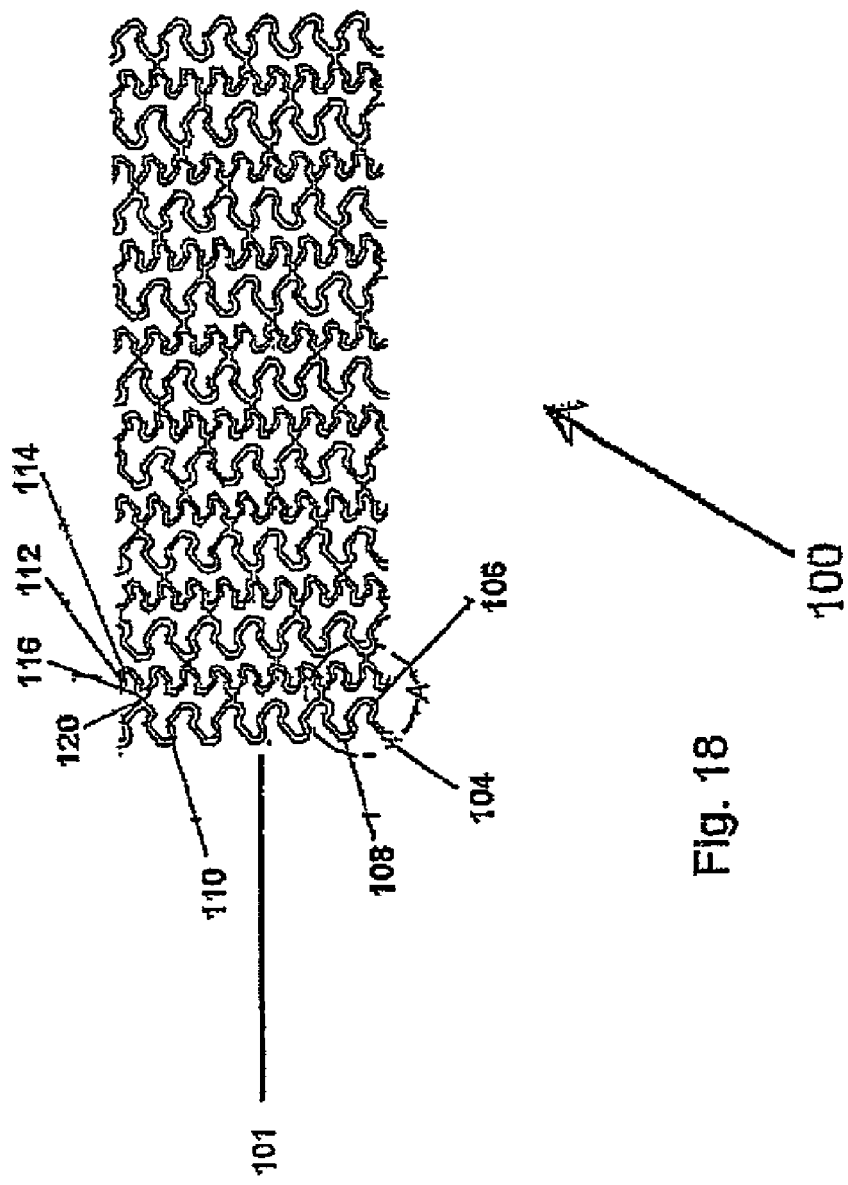
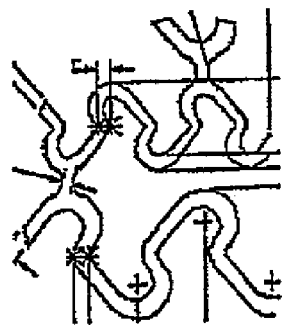
Fig. 18

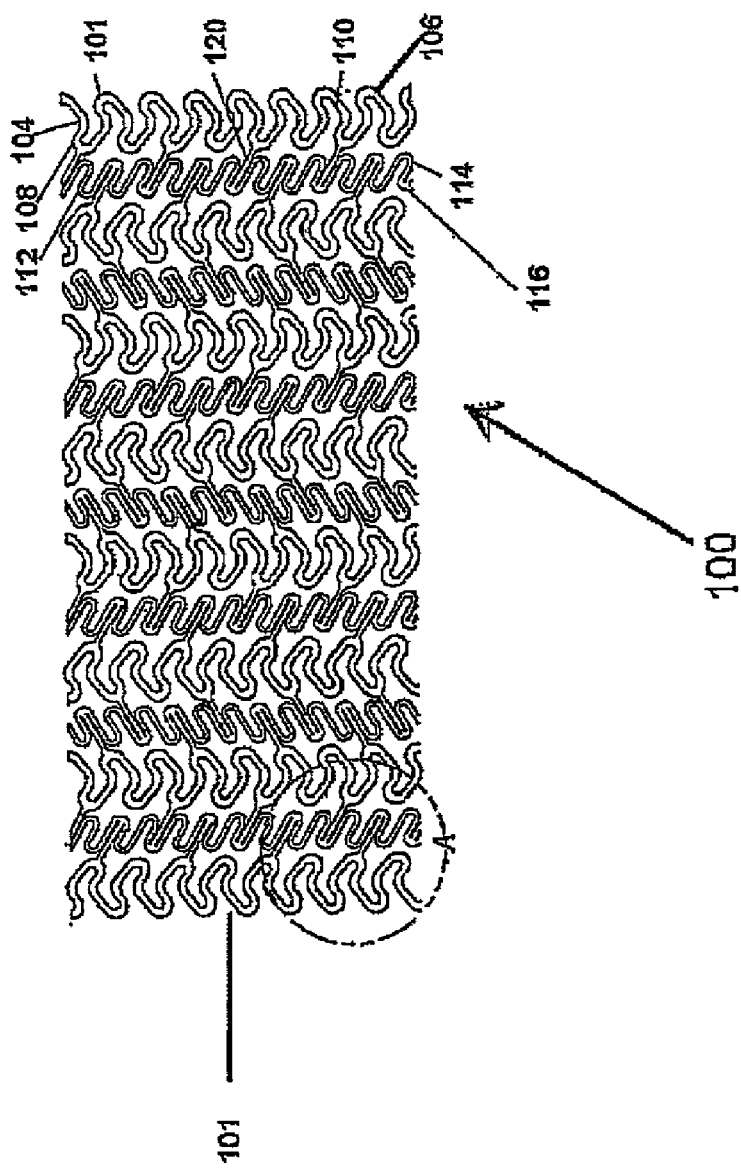
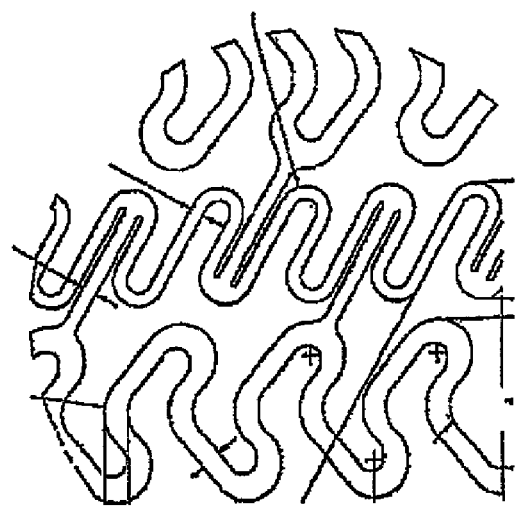
Fig. 19
DETAIL A

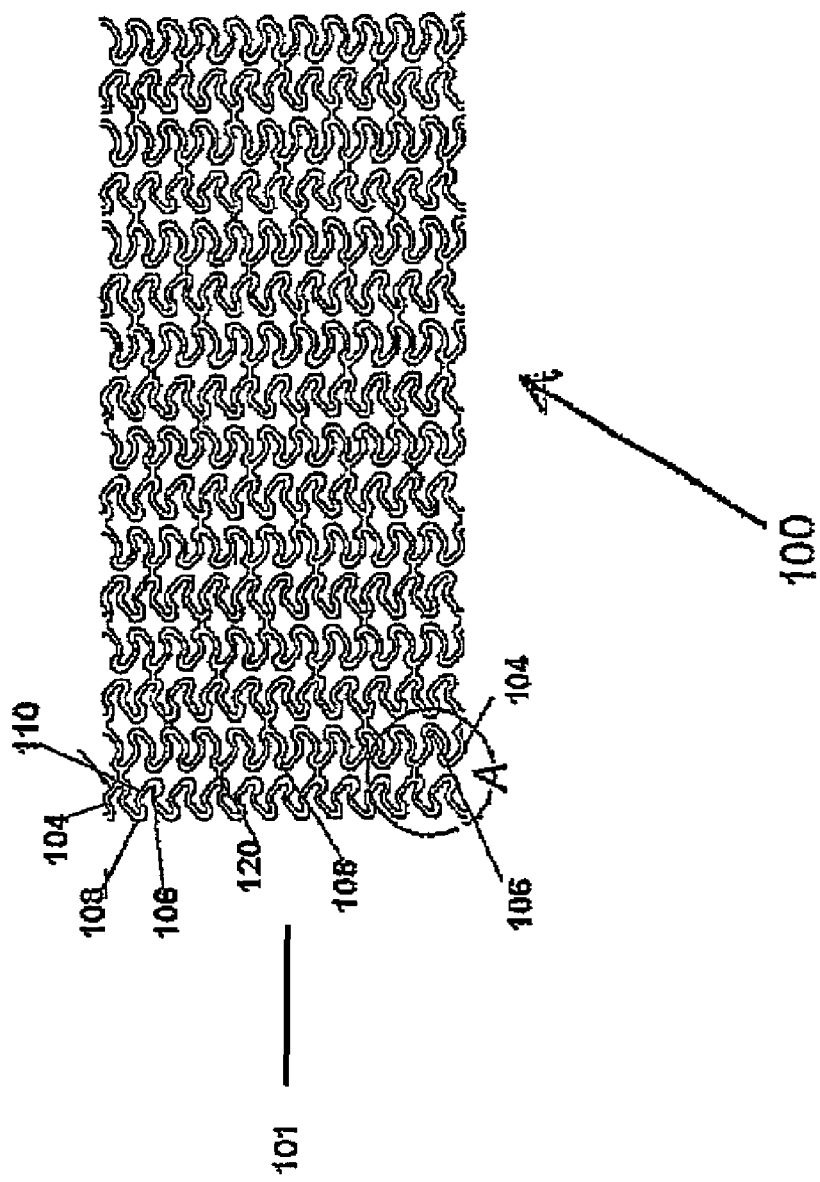
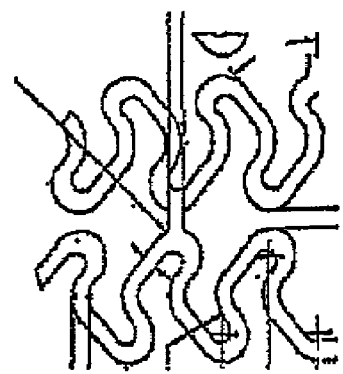
Fig. 20
DETAIL A

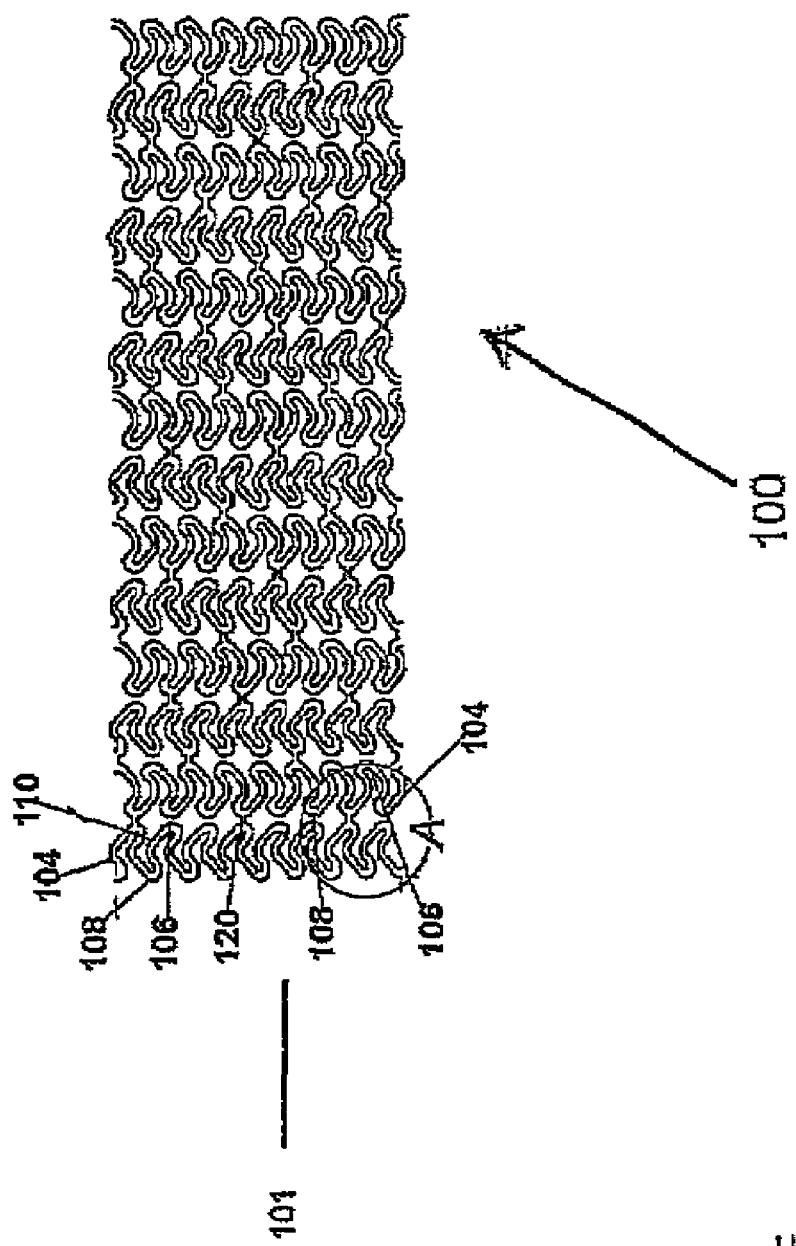
Fig. 21
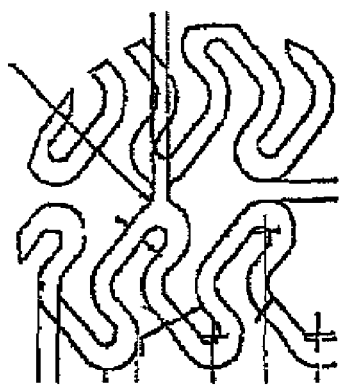
DETAIL A

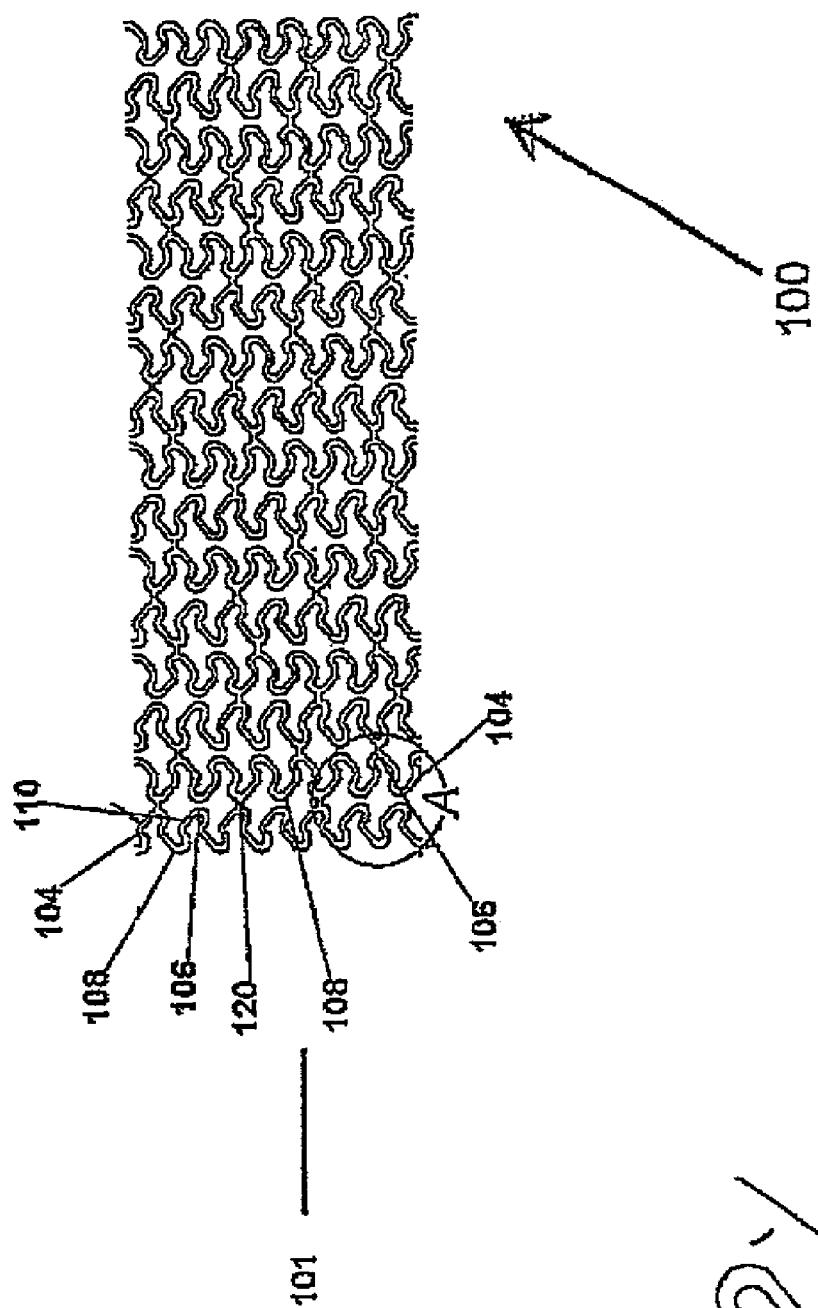
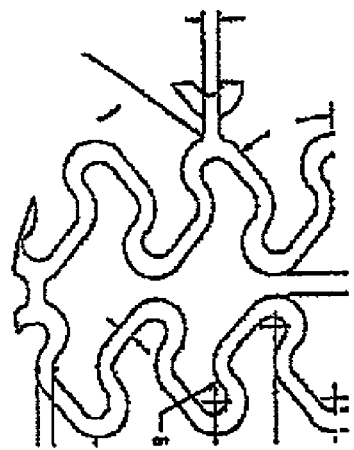
Fig. 23
DETAIL A

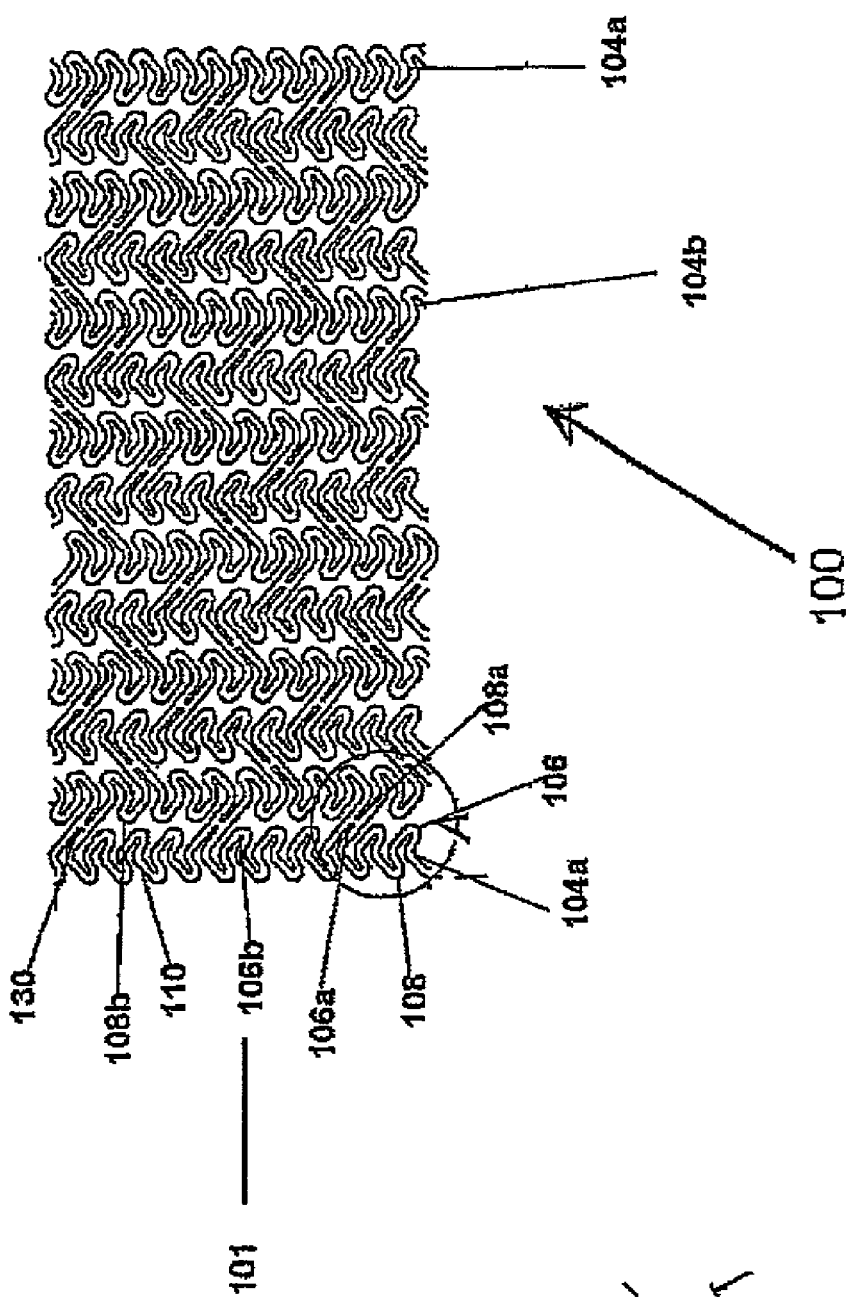
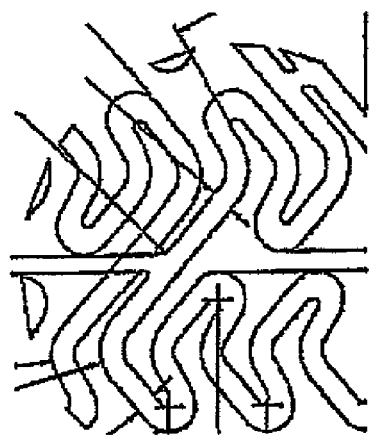
Fig. 26

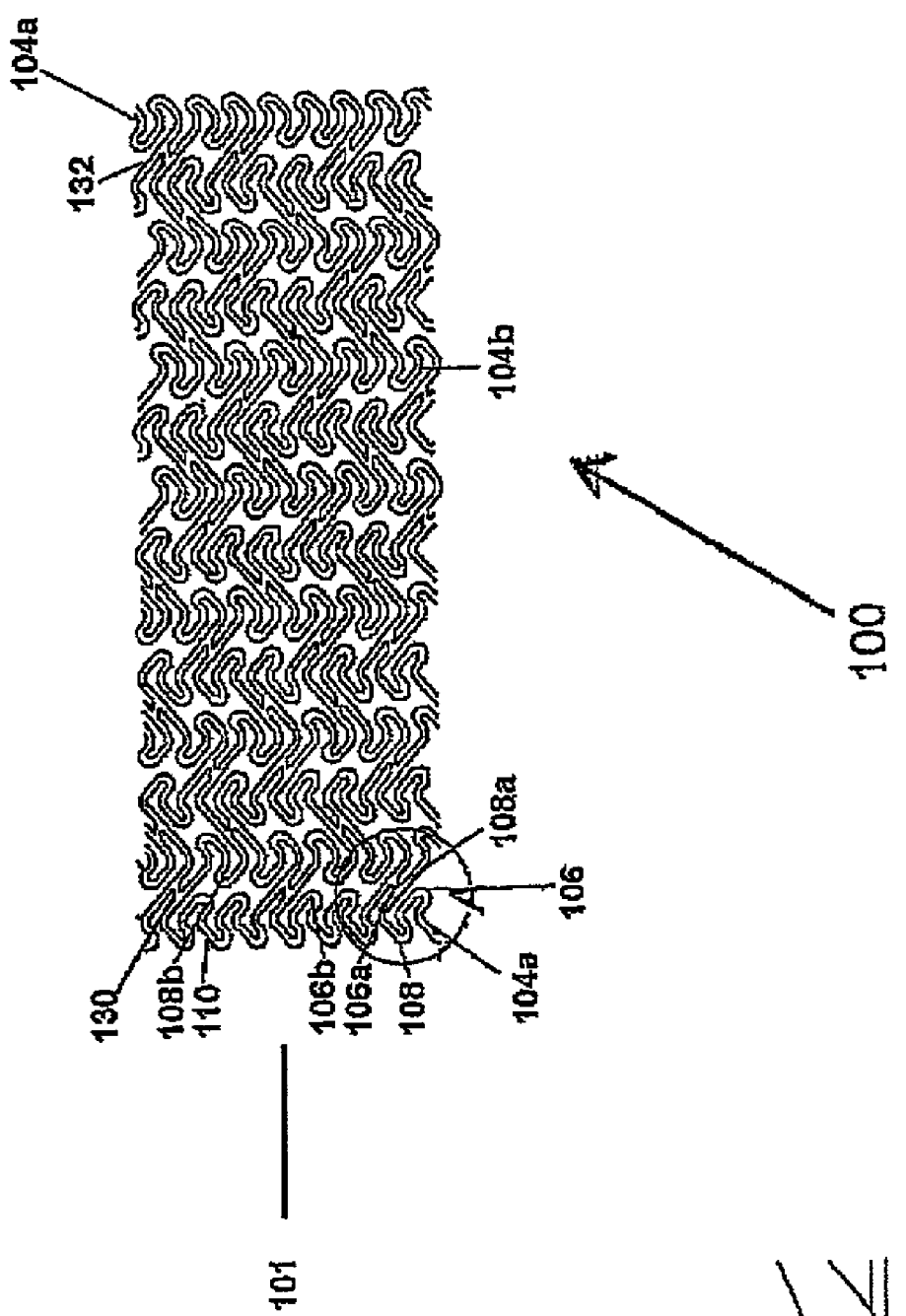
Fig. 30
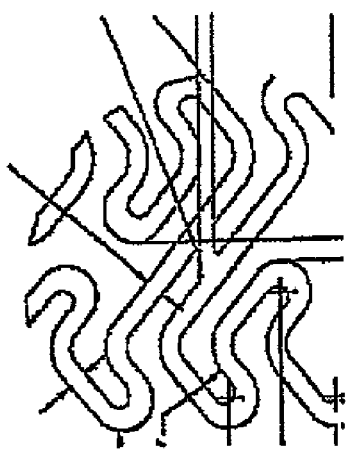
DETAIL A

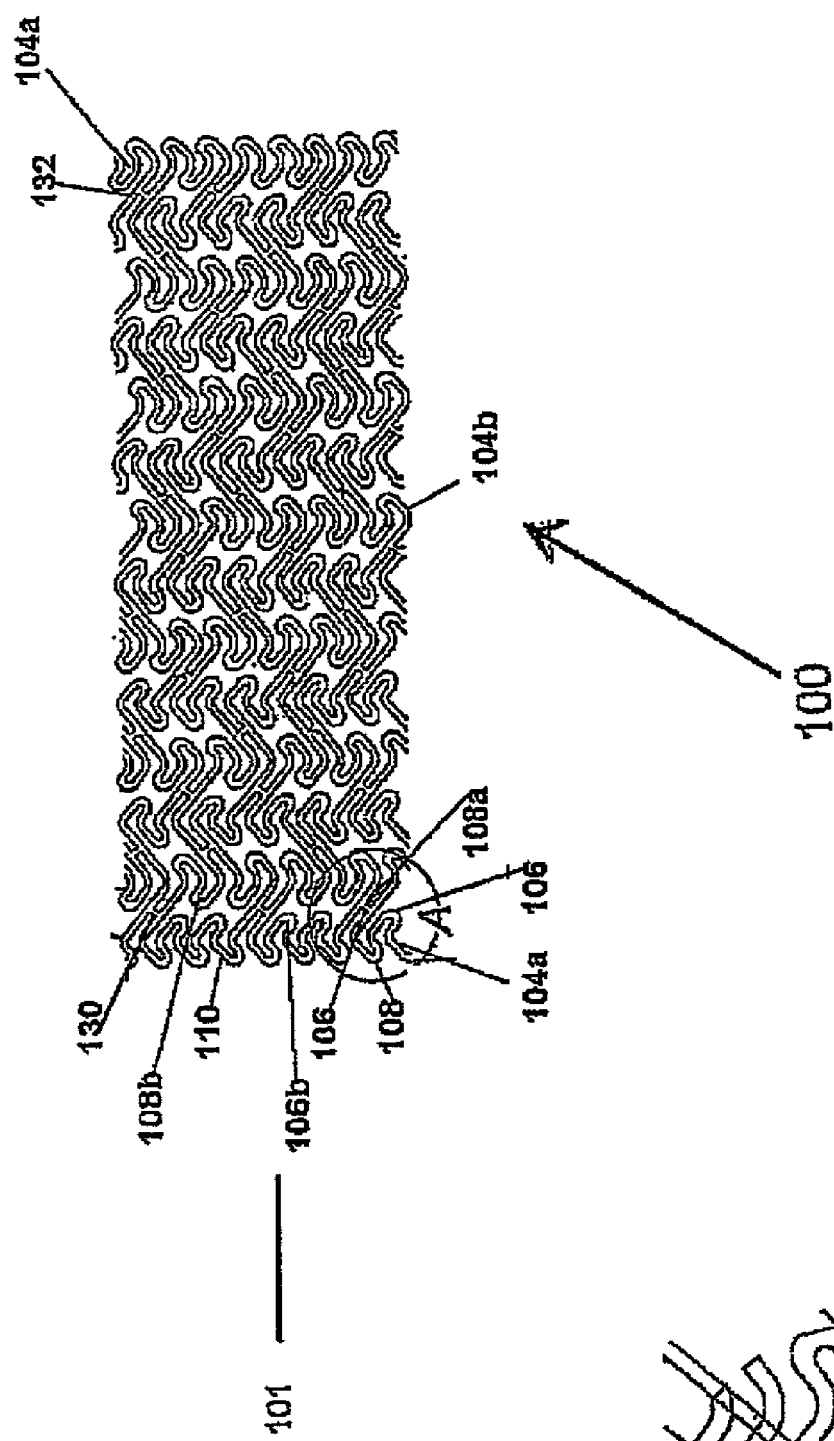
Fig. 32
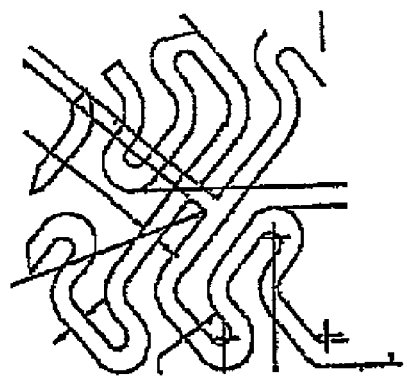
Detail A

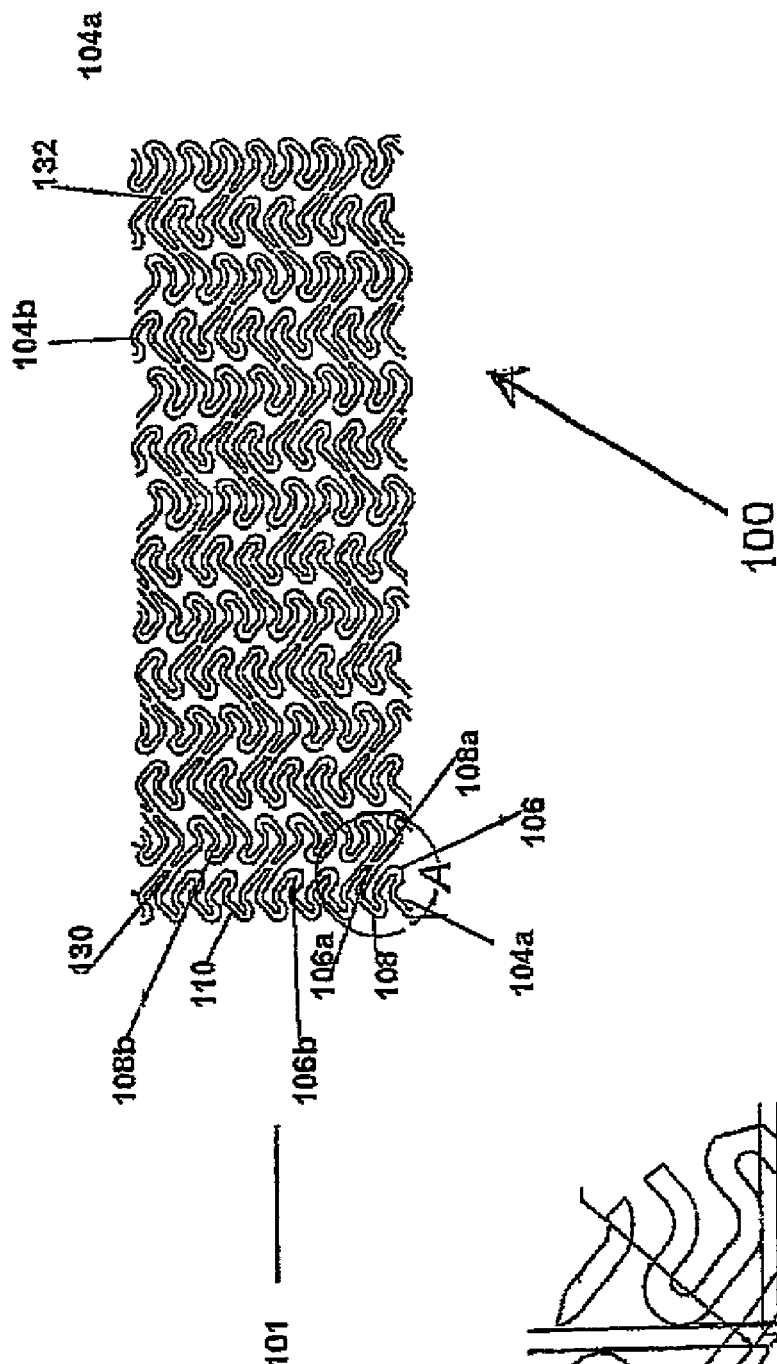
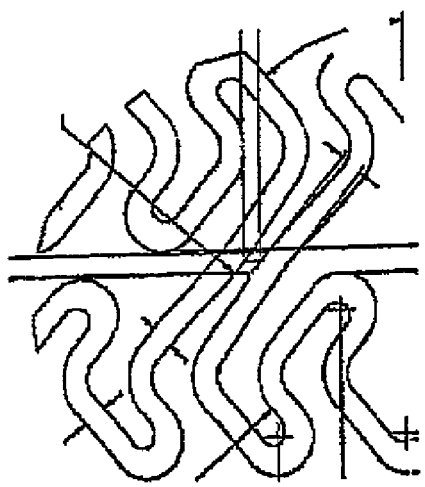
Fig. 33

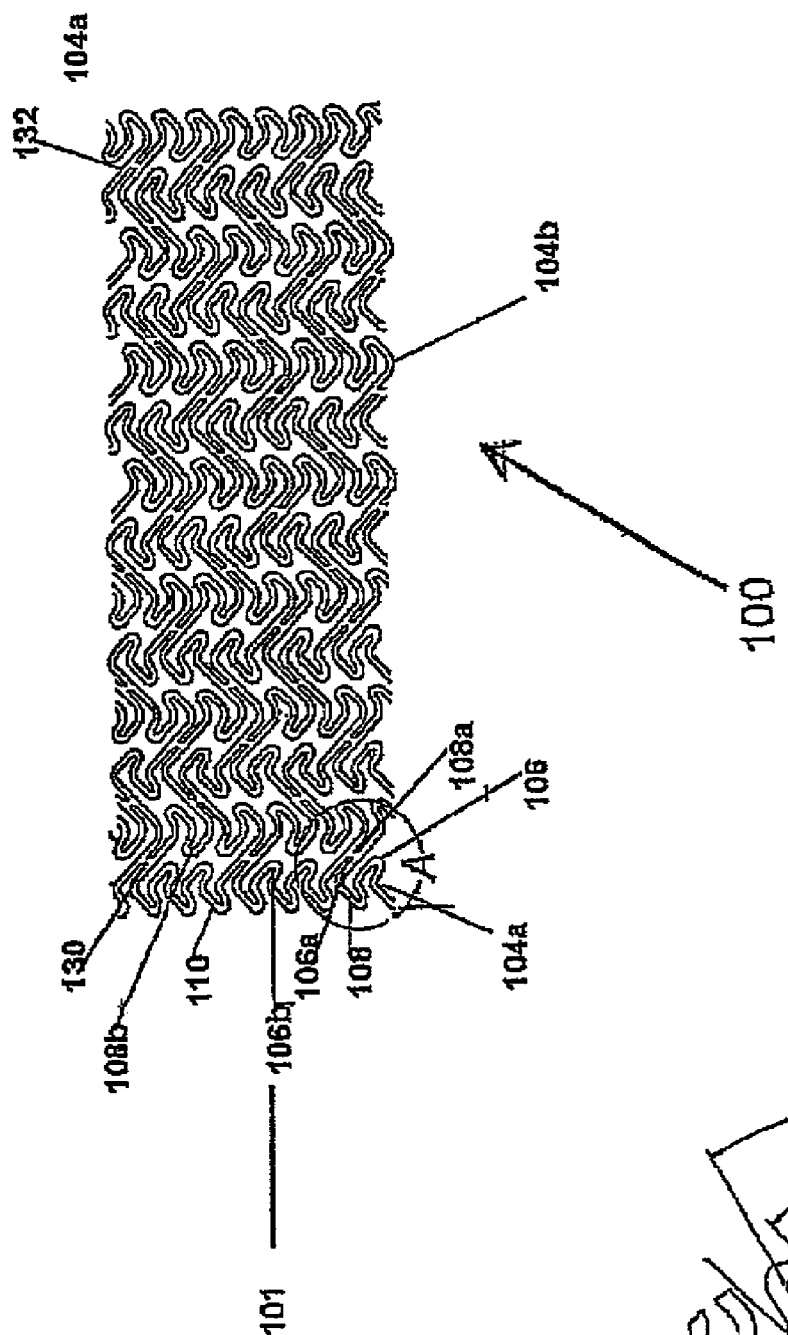
Fig. 34
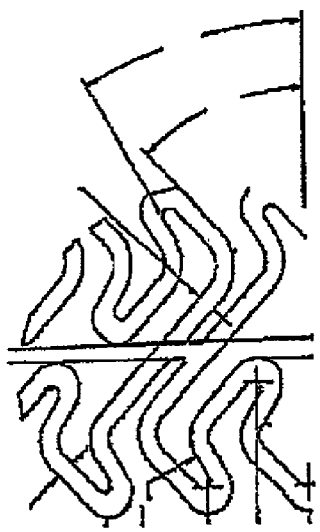
DETAIL A

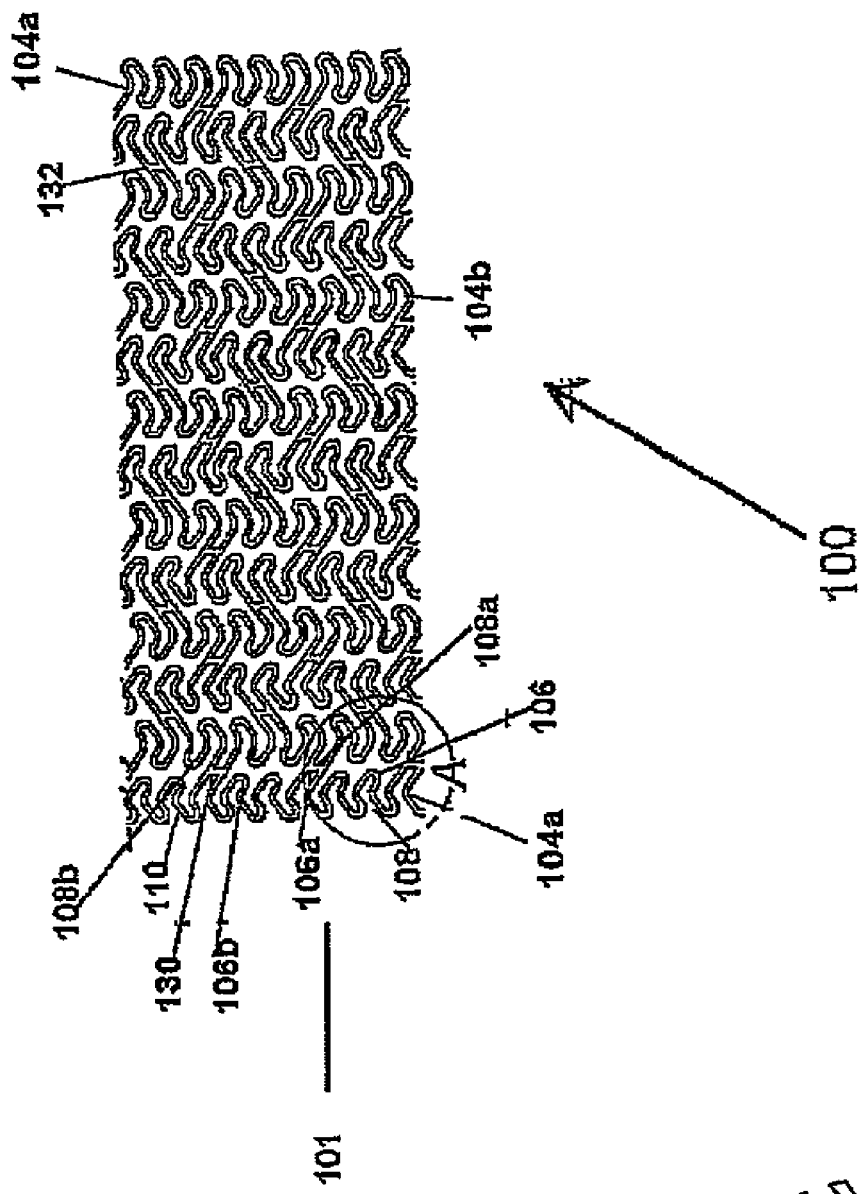
Fig. 35
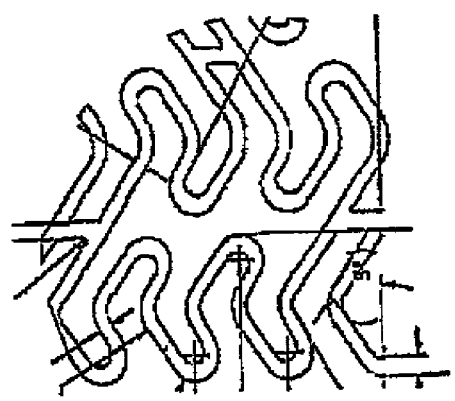
DETAIL A

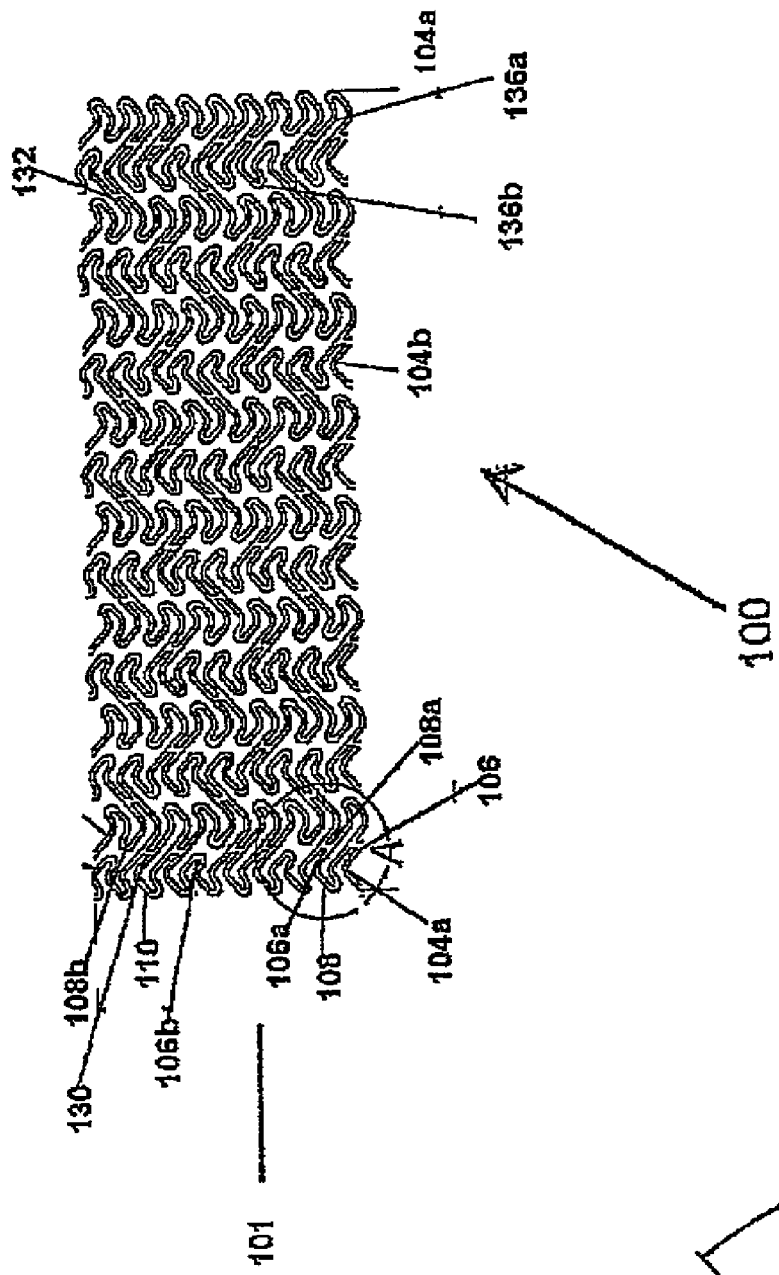
Fig. 37
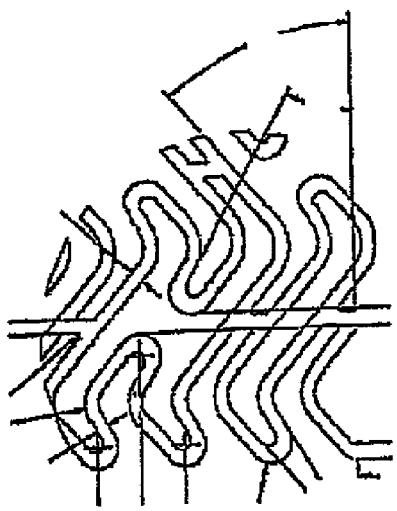
DETAIL A

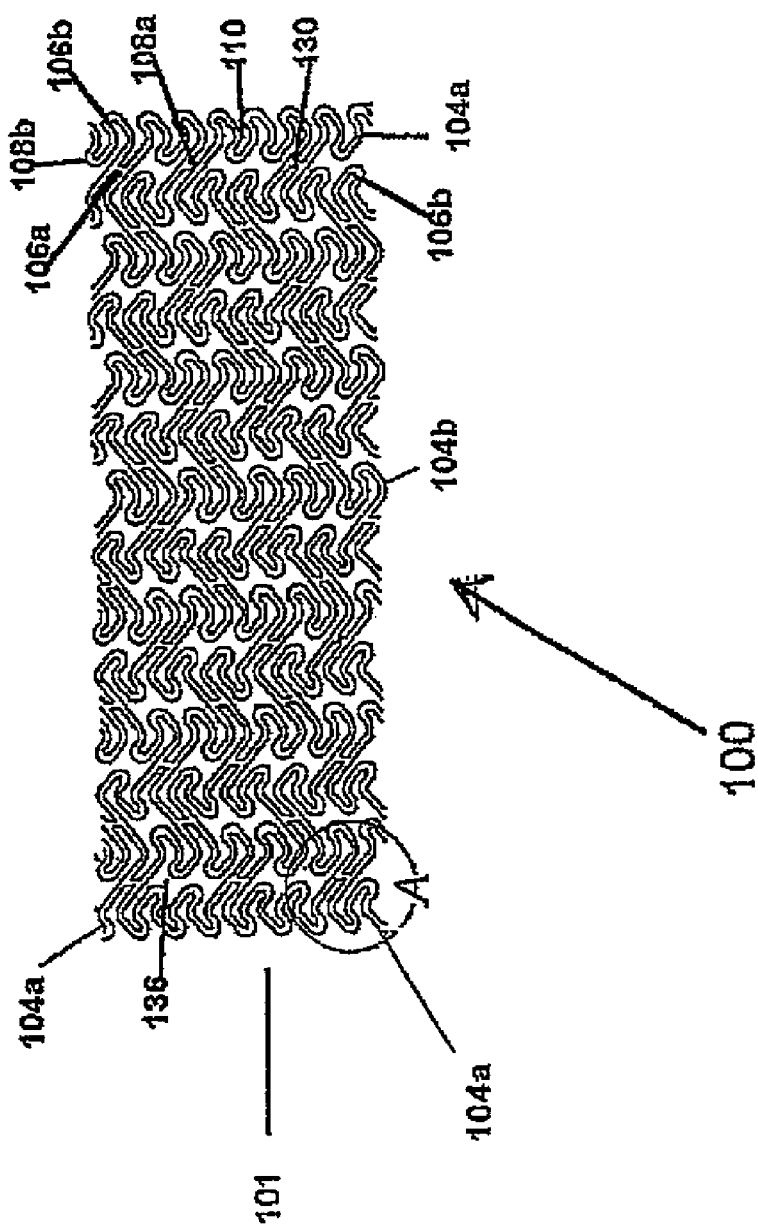
Fig. 39
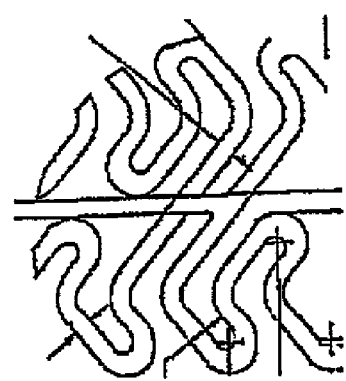
DETAIL A

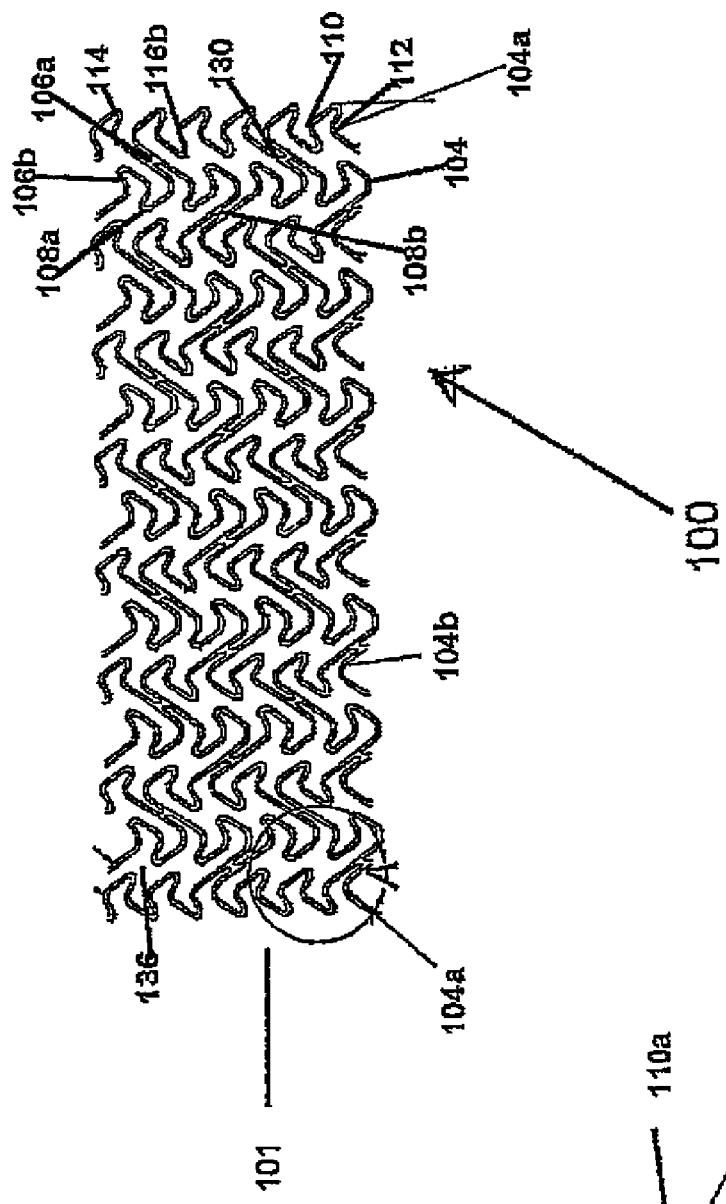
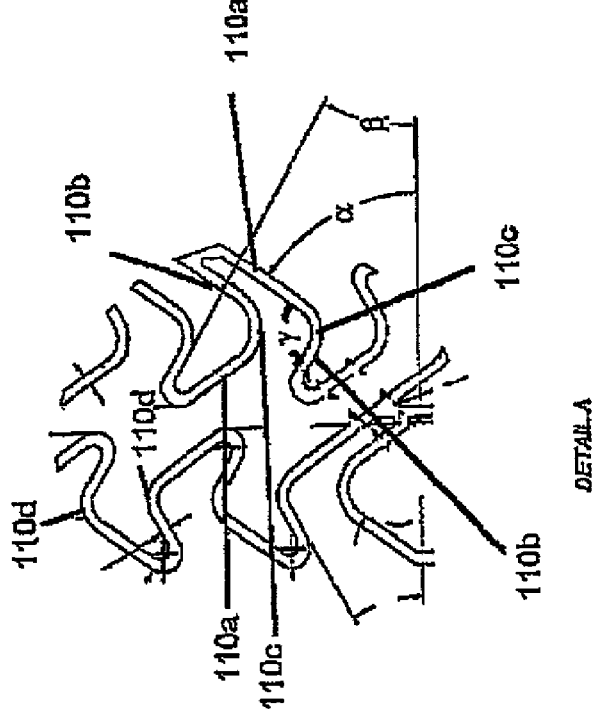
Fig. 40
DETAIL A

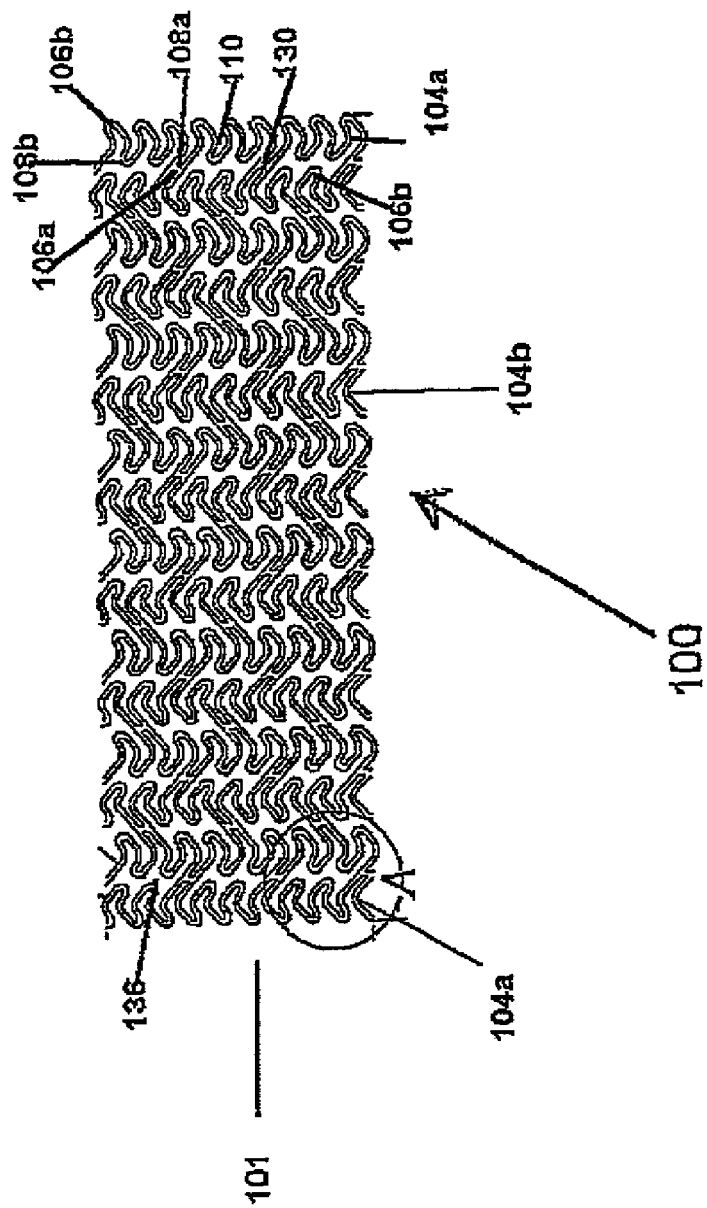
Fig. 41
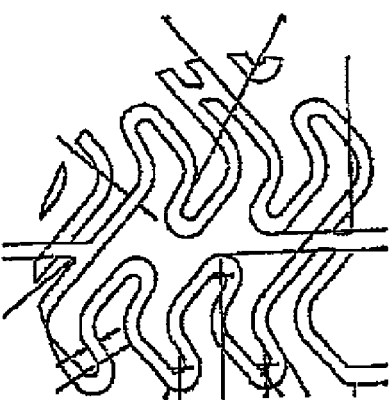
DETAIL A

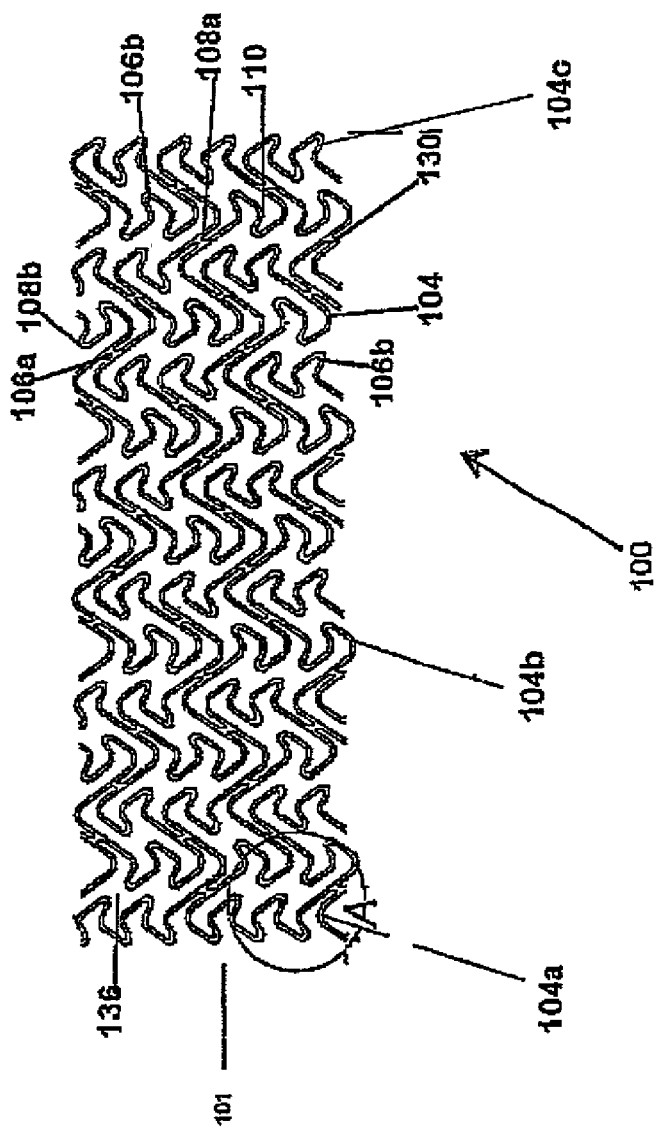
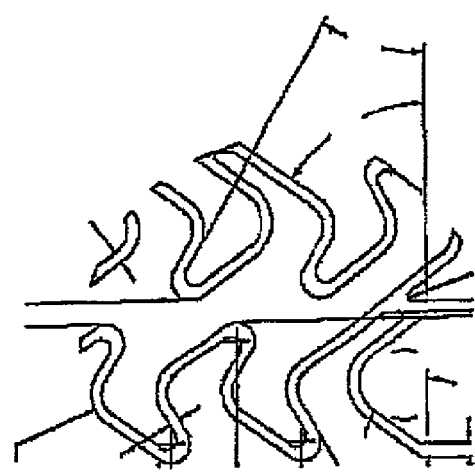
Fig. 45
DETAIL A

STENT

CROSS REFERENCE TO RELATED APPLICATIONS

This Application a continuation-in-part application of U.S. application Ser. No. 10/042,634, filed Jan. 9, 2002 now abandoned, which is a continuation-in-part application, claiming priority from U.S. application Ser. No. 09/957,983 filed Sep. 21, 2001 now U.S. Pat. No. 6,896,696 which claims the benefit of U.S. provisional application No. 60/234,548, filed Sep. 22, 2000, No. 60/272,651 filed Mar. 1, 2001 and No. 60/272,906 filed Mar. 1, 2001, all of which are incorporated herein in their entirety by reference.

BACKGROUND OF INVENTION

The use of stents in bodily lumen is well known. A stent is typically delivered in an unexpanded state to a desired location in a bodily lumen and then expanded. The stent may be expanded via the use of mechanical device such as a balloon or the stent may be self-expanding.

Because a stent often must be delivered through tortuous anatomy, it is desirable for the stent to be flexible. Increased flexibility in a stent, however, typically comes at the expense of scaffolding strength. Moreover, design features which may result in increased flexibility may also result in protruding edges which may damage vessels walls or catheter balloons during delivery of the stent through tortuous vasculature.

Many stents of conventional design include a plurality of serpentine bands which define openings in the sidewall of the stent. Typically, the openings are parallel to the longitudinal axis of the stent. Stents have been produced with openings which are oblique relative to the longitudinal axis of the stent. Stents where all of the openings are parallel to one another, however, may experience excessive torque upon delivery through tortuous vessels and resultant deployment problems.

There remains a need for a stent which has a high degree of flexibility in the unexpanded state, has adequate scaffolding strength and which does not experience excessive torque on delivery.

All US patents and all other published documents mentioned anywhere in this application are incorporated herein by reference in their entirety.

Without limiting the scope of the invention, a brief summary of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well for the purposes of complying with 37 C.F.R. 1.72.

SUMMARY OF INVENTION

In one embodiment, the invention is directed to a stent comprising a plurality of circumferential bands, circumferential bands which are adjacent one another connected one to the other, the stent including first circumferential bands characterized by a first number of alternating first peaks and first troughs joined by bent struts and second circumferential bands characterized by a second number of alternating second peaks and second troughs joined by bent struts, the second number different from the first number.

The first and second circumferential bands each define a pathway around the periphery of the stent. The first and second pathways may be of the same length or of different lengths.

Desirably, the first and second peaks and first and second troughs are oriented at an angle between 0° and 70° with respect to the longitudinal axis of the stent. More desirably, the first and second peaks and first and second troughs are oriented at an angle of at least 10 degrees with respect to the longitudinal axis of the stent and most desirably, the first and second peaks and first and second troughs are oriented at an angle of at least 15 degrees with respect to the longitudinal axis of the stent.

Typically, the first and second circumferential bands may be characterized by a longitudinal extent with the longitudinal extent of each first circumferential band desirably exceeding the longitudinal extent of each second circumferential band.

Optionally, each of the bent struts may be characterized by a width with the width of the bent struts of the first bands exceeding the width of the bent struts of the second bands.

Desirably, bent struts which are circumferentially adjacent one another are parallel to one another. More desirably, bent struts in longitudinally adjacent first and second circumferential bands are non-parallel to one another.

In one embodiment of the invention, first and second circumferential bands which are longitudinally adjacent to one another are connected by at least one connector and desirably, by a plurality of connectors. Typically, the connectors will be straight and non-parallel to the longitudinal axis of the stent. Desirably, the connectors extend from peaks of circumferential bands to troughs of adjacent circumferential bands. Also desirably, the connectors are shorter in length than the longitudinal extent of the second circumferential bands.

Where a plurality of connectors are present between adjacent first and second circumferential bands, circumferentially adjacent connectors are joined via a first pathway along a first circumferential band and a second pathway along a second circumferential band. The first pathway is desirably of the same length as the second pathway.

In one embodiment, each first pathway traverses a total of three peaks and troughs (i.e. two peaks and one trough or one peak and two troughs) and each second pathway traverse a total of five peaks and troughs (i.e. three peaks and two troughs or two peaks and three troughs).

In yet another embodiment, the invention is directed to a stent comprising a plurality of circumferential bands where circumferential bands which are adjacent one another are connected one to the other. The circumferential bands include first circumferential bands characterized by a first number of alternating first peaks and first troughs and second circumferential bands characterized by a second number of alternating second peaks and second troughs. The second number is different from the first number. The first peaks and troughs are oriented non-parallel to the longitudinal axis of the stent and the second peaks and second troughs are oriented non-parallel to the longitudinal axis of the stent. Optionally, the first and second circumferential bands each define a pathway around the periphery of the stent and the first and second pathways are the same length.

Desirably, the peaks and troughs are oriented at an angle of at least 10 degrees with respect to the longitudinal axis of the stent. More desirably, the peaks and troughs are oriented at an angle of at least 15 degrees with respect to the longitudinal axis of the stent.

Desirably, the first and second circumferential bands are each characterized by a longitudinal extent with the longitudinal extent of the first circumferential bands exceeding the longitudinal extent of the second circumferential bands.

Also desirably, first peaks and first troughs which are circumferentially adjacent one another are connected by struts and second peaks and second troughs which are circumferentially adjacent one another are connected by struts. Each of the struts is characterized by a width. The width of the struts of the first bands exceeds the width of the struts of the second bands. Typically, struts which are circumferentially adjacent one another are parallel to one another.

First and second circumferential bands which are longitudinally adjacent one another may be connected by a single connector or by a plurality of connectors. The connectors may be of any shape. In one embodiment, straight connectors are used. The connectors may be oriented parallel to the longitudinal axis or, in another embodiment, non-parallel to the longitudinal axis. Connectors with curved portions may also be used.

The connectors may extend from any region of one band to any region of an adjacent band. In one embodiment, the connectors extend from peaks of circumferential bands to troughs of adjacent circumferential bands. In one desirable embodiment, first and second circumferential bands which are longitudinally adjacent one another are connected by a plurality of connectors and the connectors are shorter in length than the longitudinal extent of the second circumferential bands. Circumferentially adjacent connectors may be joined via a first pathway along a first circumferential band and a second pathway along a second circumferential band with the first pathway being of the same length as the second pathway.

Desirably, the struts in first bands which are longitudinally adjacent one another are non-parallel to one another. More desirably, the struts in first bands which are longitudinally adjacent one another slant in opposing directions relative to the longitudinal axis of the stent.

In yet another embodiment of the invention, the first circumferential bands are connected to the second circumferential bands via straight connectors which extend between portions of similar curvature on adjacent circumferential bands. Desirably, the connectors extend between peaks of first circumferential bands and peaks of second circumferential bands and between troughs of second circumferential bands and troughs of first circumferential bands.

Typically, the connectors are shorter in length than the longitudinal extent $L_1$ of first circumferential bands.

In another embodiment, the invention is directed to a stent comprising a sidewall with a plurality of openings therein. Each opening is bounded by at least a first stent member and a second stent member. The first stent member is of a larger width than the second stent member. The first stent member comprises a plurality of bent first struts which extend non-parallel to the longitudinal axis of the stent and the second stent member comprises a plurality of bent second struts which extend non-parallel to the longitudinal axis of the stent. The bent first struts define finger like first projections which are non-parallel to the longitudinal axis of the stent and the bent second struts define finger like second projections which are non-parallel to the longitudinal axis of the stent with the number of second projections exceeding the number of first projections.

In one embodiment, each opening is defined by first projections which are nonparallel to the second projections.

In another embodiment, the openings comprise first openings and second openings, with each first opening defined by first projections which are parallel to the second projections. Typically each second opening is defined by first projections which are non-parallel to second projections.

In another embodiment, the invention is directed to a stent comprising a sidewall, the sidewall having a plurality of openings therein. Each opening is bounded by at least a first stent member and a second stent member. The first stent member is of a larger width than the second stent member. The first stent member comprises a plurality of bent first struts which extend non-parallel to the longitudinal axis of the stent and the second stent member comprises a plurality of bent second struts which extend non-parallel to the longitudinal axis of the stent. The bent first struts define finger like first projections which are non-parallel to the longitudinal axis of the stent and the bent second struts define finger like second projections which are non-parallel to the longitudinal axis of the stent. The number of first projections exceeds the number of second projections.

In yet another embodiment, the invention is directed to a stent comprising a plurality of adjacent connected circumferential bands, including first circumferential bands characterized by a first number of alternating first peaks and first troughs joined by bent struts and second circumferential bands characterized by a second number of alternating second peaks and second troughs joined by bent struts where the second number is different from the first number. Each second circumferential band is connected to one adjacent first circumferential band via at least one connector which extends from a peak on the adjacent first circumferential band to a peak on the second circumferential band. Each second circumferential band is also connected to another adjacent first circumferential band via at least one connector which extends from a trough on the another first circumferential band to a trough on the second circumferential band.

The invention is also directed to a stent comprising a plurality of connected serpentine circumferential bands including a first serpentine circumferential band having a first total circumferential length at a proximal end of the stent, a second serpentine circumferential band having a second total circumferential length at a distal end of the stent and a third serpentine circumferential band having a third total circumferential length between the proximal and distal ends of the stent. The first and second total circumferential lengths differ from one another. Desirably, the first, second and third total circumferential lengths differ from one another. More desirably, the first and second total circumferential lengths are less than the third total circumferential length.

The invention is also directed to a stent comprising a plurality of connected serpentine circumferential bands. Each serpentine circumferential band comprises a plurality of peaks and troughs. Adjacent peaks and troughs are connected by bent struts. The serpentine circumferential bands include a first serpentine circumferential band having a first total circumferential length at a proximal end of the stent, a second serpentine circumferential band having a second total circumferential length at a distal end of the stent and a third serpentine circumferential band having a third total circumferential length between the proximal and distal ends of the stent. At least one of the first and second total circumferential lengths differs from the third total circumferential length. Desirably, the first, second and third total circumferential lengths differ from one another. More desirably, the first and second total circumferential lengths are less than the third total circumferential length.

The invention is also directed to a stent comprising a plurality of connected serpentine circumferential bands. Each serpentine circumferential band comprises a plurality of peaks and troughs with adjacent peaks and troughs connected by bent struts. Adjacent serpentine circumferential bands are connected one to the other in one or more regions of overlap where a peak in one serpentine band overlaps with a trough in an adjacent serpentine circumferential band. The one or more regions of overlap extend in a longitudinal direction.

The invention is also directed to a stent comprising a plurality of connected serpentine circumferential bands. Each serpentine circumferential band comprises a plurality of peaks and troughs. Adjacent peaks and troughs are connected by nested bent struts. Serpentine circumferential bands which are adjacent one another are connected via a plurality of connections. The stent includes two serpentine circumferential bands which are connected via a first number of connections and two serpentine circumferential bands which are connected via a second number of connections, the second number different from the first number.

The invention is also directed to a stent comprising a plurality of adjacent serpentine circumferential bands containing alternating troughs and peaks. Adjacent serpentine circumferential bands have a plurality of cells therebetween. At least two adjacent serpentine circumferential bands have a plurality of first cells therebetween and a plurality of second cells therebetween. The second cells are larger than the first cells.

The invention is also directed to a stent comprising a plurality of serpentine circumferential bands including a first serpentine circumferential band comprising a plurality of peaks and troughs, adjacent peaks and troughs connected by bent struts and a second serpentine circumferential band comprising a plurality of peaks and troughs, adjacent peaks and troughs connected by relatively straight struts. The first and second serpentine circumferential bands are connected to one another.

Without being bound by theory, bent struts have been found to provide more wall coverage than straight struts. Furthermore, using bent struts typically requires more material, i.e. metal, and thus provides improved radiopacity as well.

Additional details and/or embodiments of the invention are discussed below.

BRIEF DESCRIPTION OF DRAWINGS

FIG. 1a is a flat layout view of an inventive stent.

FIG. 1b shows an enlarged view of region A of the stent shown in flat layout view in FIG. 1a.

FIG. 2a is a flat layout view of an embodiment of the inventive stent of the present invention which is similar to that shown in FIG. 1a.

FIG. 2b shows an enlarged view of region A of the stent shown in flat layout view in FIG. 2a.

FIG. 3a shows an alternative embodiment of the inventive stent of the present invention.

FIG. 3b shows an enlarged view of region A of the stent shown in flat layout view in FIG. 3a.

FIG. 4b shows an enlarged view of region A of the stent shown in flat layout view in FIG. 4a.

FIG. 5b shows an enlarged view of region A of the stent shown in flat layout view in FIG. 5a.

FIG. 6b shows an enlarged view of region A of the stent shown in flat layout view in FIG. 6a.

FIG. 7a is a flat layout view of an embodiment of the inventive stent of the present invention.

FIG. 7b shows an enlarged view of region A of the stent shown in flat layout view in FIG. 7a.

FIG. 8b shows an enlarged view of region A of the stent shown in flat layout view in FIG. 8a.

FIG. 9b shows an enlarged view of region A of the stent shown in flat layout view in FIG. 9a.

FIG. 10b shows an enlarged view of region A of the stent shown in flat layout view in FIG. 10a.

FIG. 12-19 show flat layout views of other embodiments of the inventive stents of the present invention, the stents having large and small amplitude circumferential bands.

FIGS. 20-25 show flat layout views of other embodiments of the inventive stents of the present invention, the stents having circumferential bands of the same amplitude.

FIGS. 26-45 show flat layout views of other embodiments of the inventive stents of the present invention, the stents having overlapping circumferential bands.

DETAILED DESCRIPTION

Figure 2A:
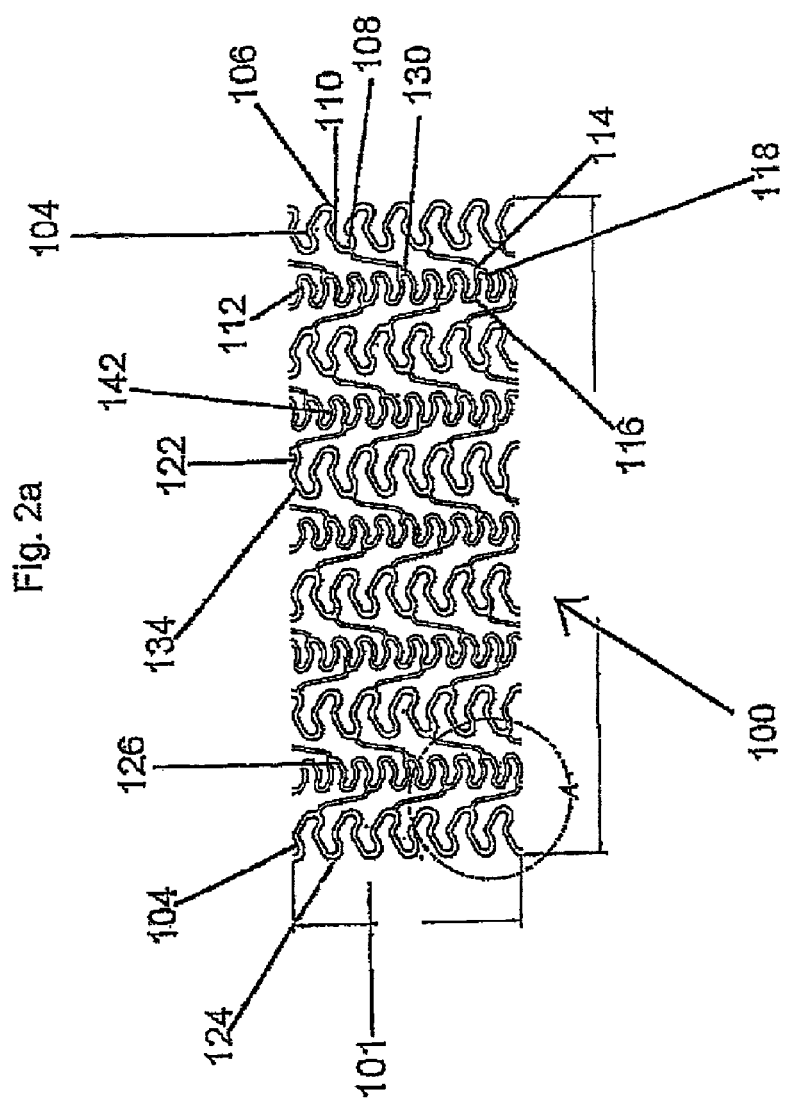

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Also for the purposes of this disclosure, the term 'bent strut' does not implicate a method of manufacture and is intended to include struts which have curves, struts which are angled, and struts which are curvilinear, regardless of how the struts or the stent as a whole are manufactured. Bent struts as referred to herein typically have two segments joined by a bent portion.

Finally, for the purposes of this disclosure, the expression 'total circumferential length' refers to the length of a circumferential band as the band is traversed about the circumference of the stent.

In one embodiment, the invention is directed to a stent such as that shown by way of example at 100 in FIG. 1a comprising a plurality of circumferential bands. Circumferential bands which are adjacent one another are connected one to the other. The circumferential bands include first circumferential bands 104 characterized by a first number of alternating first peaks 106 and first troughs 108 joined by bent struts 110 and second circumferential bands 112 characterized by a second number of alternating second peaks 114 and second troughs 116 joined by bent struts, 118. Typically, as shown in FIG. 1a, the second number of second peaks and troughs is different from the first number of first peaks and troughs and desirably exceeds the first number.

The first and second circumferential bands each define a pathway around the periphery of the stent. The first and second pathways may be of the same length or of different lengths. Desirably, the first and second pathways are the same length.

Also desirably, the first and second peaks and first and second troughs are oriented at an angle between 0° and 70° with respect to the longitudinal axis of the stent, more desirably they are oriented at an angle of at least 10 degrees with respect to the longitudinal axis of the stent, and most desirably, the first and second peaks and first and second troughs are oriented at an angle of at least 15 degrees with respect to the longitudinal axis of the stent.

Typically, as shown in FIG. 1b, the first and second circumferential bands may be characterized by longitudinal extents $L_1$ and $L_2$. The longitudinal extent of each first circumferential band $L_1$ desirably exceeds the longitudinal extent $L_2$ of the individual second circumferential bands.

Each of the bent struts may be characterized by a width. Optionally, the width of the bent struts of the first bands $W_1$ exceeds the width of the bent struts of the second bands $W_2$.

Desirably, as shown in FIG. 1a, bent struts which are circumferentially adjacent one another are parallel to one another. More desirably, as shown in FIG. 1a, bent struts in longitudinally adjacent first and second circumferential bands are non-parallel to one another.

In one embodiment of the invention, as shown in FIG. 1a, first and second circumferential bands which are longitudinally adjacent one another are connected by at least one connector 120 and desirably, by a plurality of connectors. Typically, the connectors will be straight and non-parallel to the longitudinal axis 101 of the stent. In other embodiments of the invention, other types of connectors may be used for example connectors with one or more curves and/or connectors of different lengths. Desirably, as shown in FIG. 1a, the connectors extend from peaks of circumferential bands to troughs of adjacent circumferential bands. Also desirably, as shown in FIG. 1a, the connectors are shorter in length than the longitudinal extent $L_2$ of the second circumferential bands.

Where a plurality of connectors are present between adjacent first and second circumferential bands, circumferentially adjacent connectors are joined via a first pathway along a first circumferential band and a second pathway along a second circumferential band, the first pathway desirably being of the same length as the second pathway.

In the embodiment of FIG. 1a, each first pathway traverses a total of three peaks and troughs (i.e. two peaks and one trough or one peak and two troughs) and each second pathway traverse a total of five peaks and troughs (i.e. three peaks and two troughs or two peaks and three troughs).

In other words, between circumferentially adjacent connectors which connect first and second circumferential bands together, in the first band, there are a total of three peaks and troughs between the connectors, and in the second circumferential band there are a total of five peaks and troughs between connectors.

Without being bound by theory, the alternating orientation of adjacent first and second circumferential bands is believed to prevent significant rotation and build-up of torque and the accompanying degradation of stent performance.

In another embodiment, the invention is directed to a stent such as that shown by way of example at 100 in FIG. 2a comprising a plurality of circumferential bands substantially similar to those shown in FIG. 1a. As in the embodiment shown in FIG. 1a, the first and second circumferential bands each define a pathway around the periphery of the stent. The first and second pathways may be of the same length or of different lengths. Desirably, the first and second pathways are the same length.

Also as in the embodiment shown in FIG. 1a, the first circumferential bands 104 are characterized by a first number of alternating first peaks 106 and first troughs 108 joined by bent struts 110 and second circumferential bands 112 characterized by a second number of alternating second peaks 114 and second troughs 116 joined by bent struts, 118. Typically, as shown in FIG. 1a, the second number of second peaks and troughs is different from the first number of first peaks and troughs and desirably exceeds the first number.

In the embodiment shown in FIG. 2a, however, in contrast to that shown in FIG. 1a, the connectors do not extend between the nearest neighboring peaks and troughs, but rather every first peak of every first circumferential band 104 is connected to every third trough of a second adjacent circumferential band.

Figure 2B:
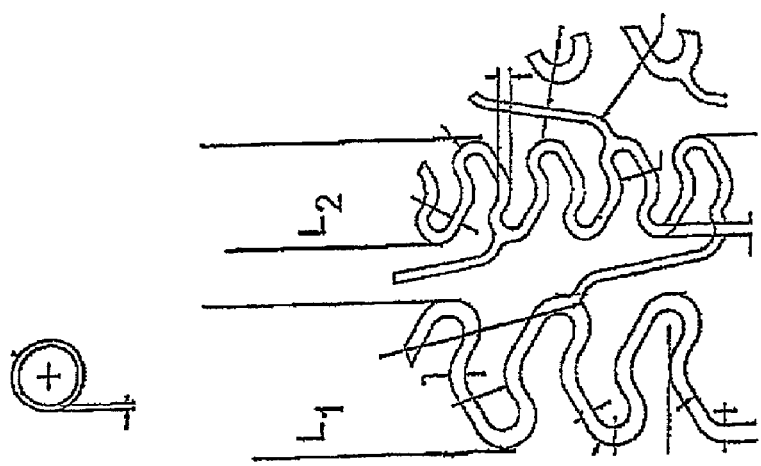

As in FIG. 1b, the first and second circumferential bands may be characterized by longitudinal extents $L_1$ and $L_2$ as shown in FIG. 2b. The longitudinal extent of each first circumferential band $L_1$ desirably exceeds the longitudinal extent $L_2$ of the individual second circumferential bands.

Again as in FIG. 1a, the first and second circumferential bands which are longitudinally adjacent one another are connected by at least one connector 120 and desirably, by a plurality of connectors. Desirably, as shown in FIG. 2a, the connectors extend from peaks of circumferential bands to troughs of adjacent circumferential bands as in FIG. 1a. However, in the embodiment shown in FIG. 2a, the connectors are significantly longer in length than the longitudinal extent $L_2$ of the second circumferential bands.

Where a plurality of connectors are present between adjacent first and second circumferential bands, circumferentially adjacent connectors are joined via a first pathway along a first circumferential band and a second pathway along a second circumferential band, the first pathway desirably being of the same length as the second pathway.

In the embodiment shown in FIG. 2a, each first pathway traverses a total of four peaks and troughs (i.e. two peaks and two troughs) and each second pathway traverse a total of six peaks and troughs (i.e. three peaks and three troughs).

In another embodiment, the invention is directed to a stent such as that shown by way of example at 300 in FIG. 3a comprising a plurality of circumferential bands. This embodiment is also similar to the embodiments shown in FIGS. 1a and 2a.

Circumferential bands which are adjacent one another are connected one to the other. The circumferential bands include first circumferential bands 304 characterized by a first number of alternating first peaks 306 and first troughs 308 joined by bent struts 310 and second circumferential bands 312 characterized by a second number of alternating second peaks 314 and second troughs 316 joined by bent struts. The number of second peaks and troughs is different from the number of first peaks and troughs and desirably exceeds the first number.

The first and second circumferential bands each define a pathway around the periphery of the stent. The first and second pathways may be of the same length or of different lengths but are desirably the same length.

As shown in FIG. 3b, the first and second troughs are oriented at an angle of at least 10 degrees with respect to the longitudinal axis 301 of the stent. More desirably, the first and second peaks and first and second troughs are oriented at an angle of at least 15 degrees with respect to the longitudinal axis of the stent. In the particular embodiment shown in FIG. 3b, the first and second peaks and first and second troughs, are actually oriented at an angle of about 40 degrees with respect to the longitudinal axis of the stent.

Typically, as shown in FIG. 3b, the first and second circumferential bands may be characterized by longitudinal lengths $L_1$ and $L_2$ which may be of the same length, or of a different length. Desirably, $L_1$ exceeds the longitudinal extent $L_2$ of the individual second circumferential bands.

Each of the bent struts may be characterized by a width. Optionally, the width of the bent struts of the first bands $W_1$ exceeds the width of the bent struts of the second bands $W_2$.

The first and second circumferential bands which are longitudinally adjacent one another are connected by at least one connector 320 and preferably by a plurality of connectors. In this particular embodiment, the connectors are straight, and are nonparallel to the longitudinal axis 301 of the stent 300. Also in the embodiment shown in FIG. 3a, the connectors are significantly shorter than the longitudinal extent of the circumferential bands $L_2$. Other connectors may be optionally used, however including connectors having more curves or being of a different length.

In this embodiment, the connectors extend between peaks of circumferential bands to troughs of adjacent circumferential bands. In this particular embodiment, the connectors are shorter in length than the extent $L_2$ of the second circumferential bands.

This may be optionally described in terms of first and second pathways. Where a plurality of connectors are present between adjacent first and second circumferential bands, circumferentially adjacent connectors are joined via a first pathway along a first circumferential band and a second pathway along a second circumferential band, the first pathway desirably being of the same length as the second pathway.

In the embodiment shown in FIG. 3a, the first pathway traverses a total of four peaks and troughs (two peaks and two troughs) and the second pathway traverses a total of six peaks and troughs (three peaks and three troughs).

Figure 4A:
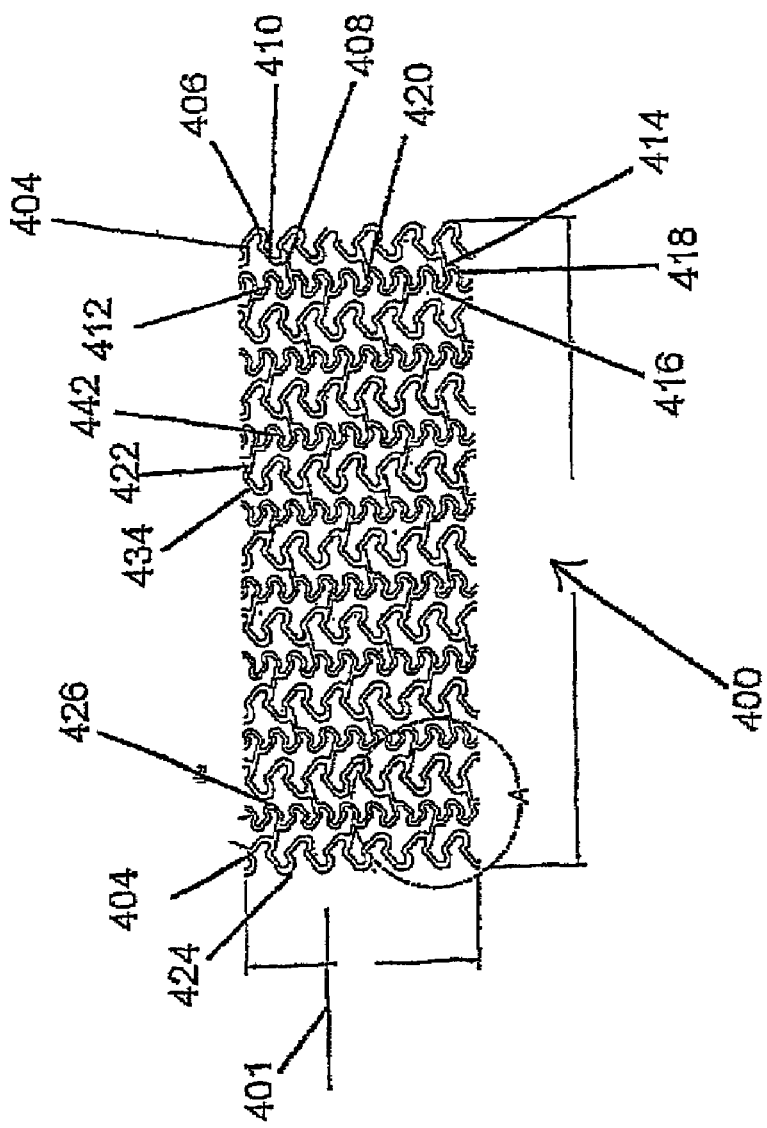
FIG. 4a is a flat layout view of an embodiment of the inventive stent of the present invention.
Figure 4B:
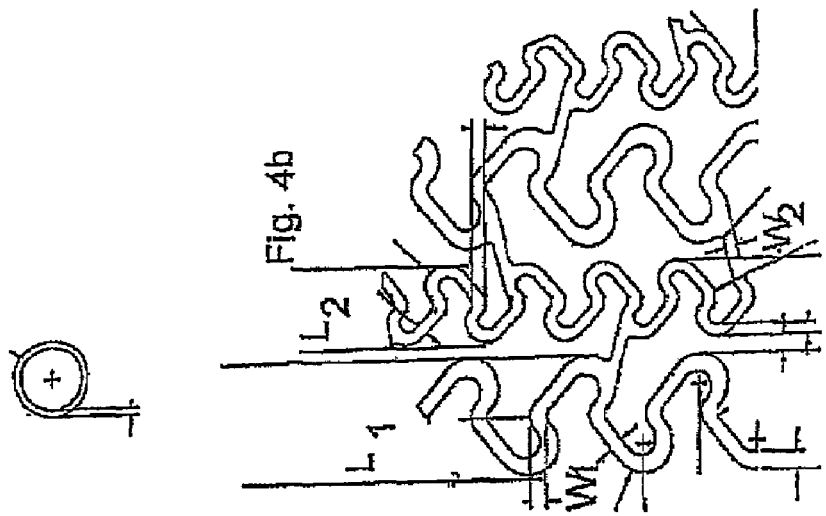

FIG. 4a illustrates an embodiment similar to those shown in FIGS. 1a-3a as described above.

Again, there are first and second circumferential bands which define a pathway around the periphery of the stent. The first and second pathways may be of the same length or of different lengths but are desirably the same length.

The first and second circumferential bands which are longitudinally adjacent one another are connected by at least one connector 420 and preferably by a plurality of connectors. In this particular embodiment, the connectors are straight, and are nonparallel to the longitudinal axis 401 of the stent 400. Other connectors may be optionally used, however including connectors having more curves or being of a different length.

In this embodiment, the connectors extend between peaks of circumferential bands to troughs of adjacent circumferential bands. In this particular embodiment, the connectors are shorter in length than the extent $L_2$ of the second circumferential bands.

This may be optionally described in terms of first and second pathways. Where a plurality of connectors are present between adjacent first and second circumferential bands, circumferentially adjacent connectors are joined via a first pathway along a first circumferential band and a second pathway along a second circumferential band, the first pathway desirably being of the same length as the second pathway.

Again, as in the embodiment shown in FIG. 3a, the embodiment shown in FIG. 4a includes a first pathway which traverses a total of four peaks and troughs (two peaks and two troughs) and the second pathway traverses a total of six peaks and troughs (three peaks and three troughs).

The connectors in the embodiment shown in FIG. 4a are at a different angle relative to the longitudinal axis 401 of stent 400 than those shown in FIG. 3a, the angle being smaller relative to the longitudinal axis in the embodiment shown in FIG. 4a.

An alternative embodiment of the inventive stent of the present invention is shown generally at 500 in FIG. 5a and again includes a plurality of circumferential bands. Circumferential bands which are adjacent one another are connected one to the other. The circumferential bands include first circumferential bands 504 characterized by a first number of alternating first peaks 506 and first troughs 508 joined by bent struts 510 and second circumferential bands 512 characterized by a second number of alternating second peaks 514 and second troughs 516 joined by bent struts 518. In this particular embodiment, the number of second peaks and troughs is the same as the number of first peaks and troughs.

The first and second circumferential bands each define a pathway around the periphery of the stent. The first and second pathways may be of the same length or of a different length. In the embodiment shown in FIG. 5a, the first and second pathways are of the same length.

The first and second peaks and first and second troughs are oriented at an angle of at least 10 degrees with respect to the longitudinal axis 501 of the stent 500, and desirably are oriented at an angle of at least 15 degrees with respect to the longitudinal axis 501.

Figure 5A:
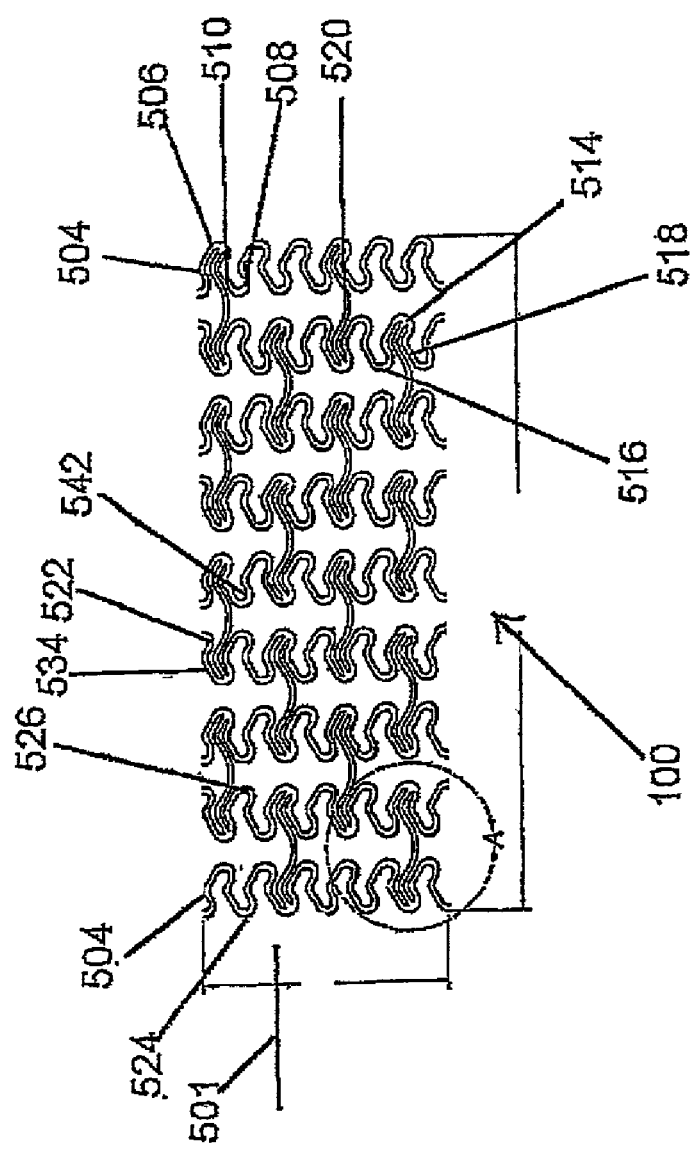
FIG. 5a is a flat layout view of an embodiment of the inventive stent of the present invention.
Figure 5B:
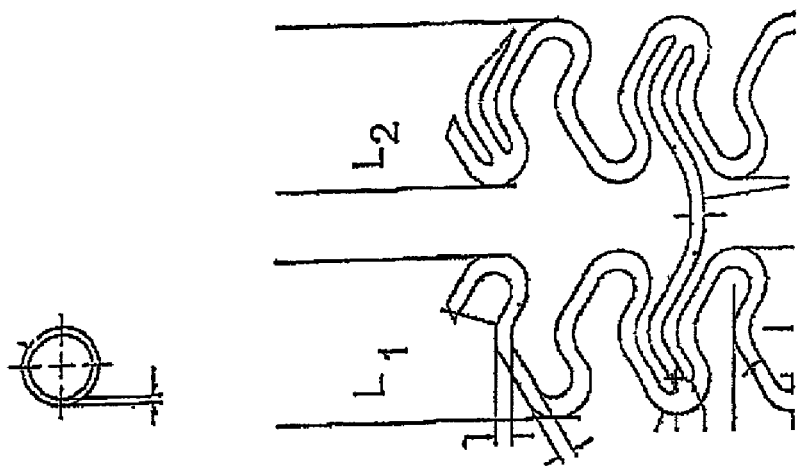

In this particular embodiment, as shown in FIG. 5b, the longitudinal extent $L_1$ of the first circumferential band is substantially equal in length to the longitudinal extent $L_2$ of the second circumferential band.

Also in the embodiment shown in FIG. 5b, the width of each of the bent struts of the first bands $W_1$ is equal to the width of the bent struts of the second bands $W_2$. Optionally, the widths may be different. For example, the width of the first bands $W_1$ may exceed the width of the second bands $W_2$.

In the embodiment shown in FIG. 5a, first and second circumferential bands which are longitudinally adjacent one another are connected by at least one connector 520 and desirably, by a plurality of connectors. Typically, in this embodiment, the connectors will be curved as opposed to the straight connectors as shown in some of the other embodiments. In this embodiment, the connectors extend from the troughs of circumferential bands to troughs of adjacent circumferential bands. The connectors are shown longer in length than the longitudinal extents $L_1$ and $L_2$ of the circumferential bands.

Where a plurality of connectors are present between adjacent first and second circumferential bands, circumferentially adjacent connectors are joined via a first pathway along a first circumferential band and a second pathway along a second circumferential band, the first pathway desirably being of the same length as the second pathway. Each first pathway traverses a total of six peaks and troughs (three peaks and three troughs) and each second pathway traverses a total of six peaks and troughs (three peaks and three troughs).

Figure 6A:
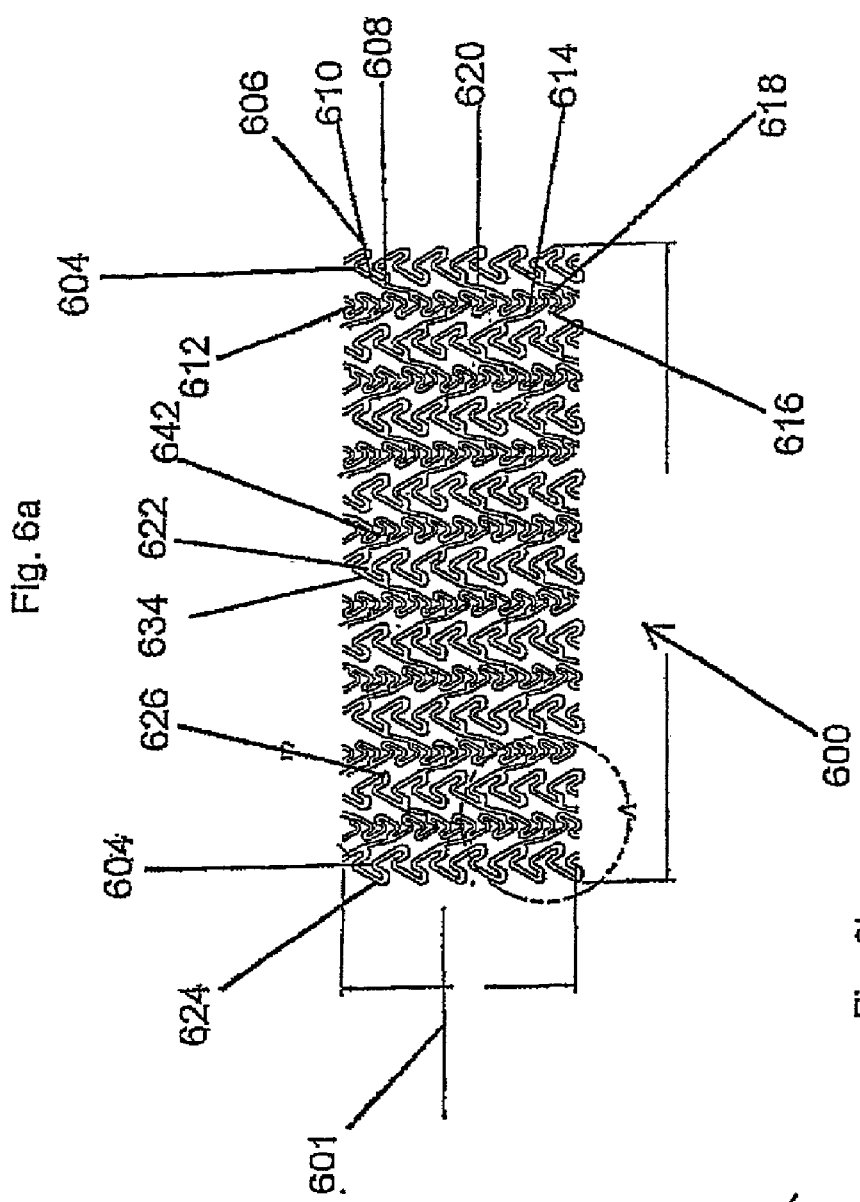
FIG. 6a is a flat layout view of an embodiment of the inventive stent of the present invention.
Figure 6B:
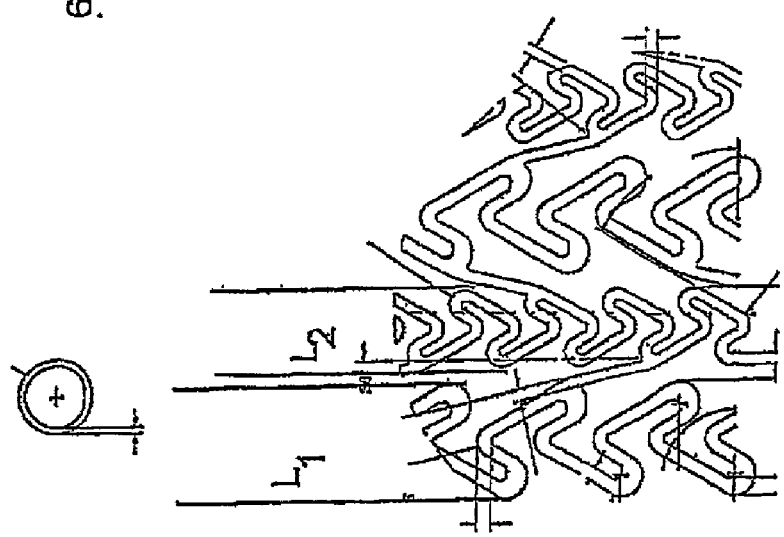

In yet another alternative embodiment of the inventive stent of the present invention shown generally at 600 in FIG. 6a, the stent includes a plurality of circumferential bands wherein circumferential bands which are adjacent one another are connected one to the other. The circumferential bands include first circumferential bands 604 characterized by a first number of alternating first peaks 606 and first troughs 608 and second circumferential bands 612 characterized by a second number of alternating second peaks 614 and second troughs 616. The second number is different from the first number. The first peaks and troughs are oriented non-parallel to the longitudinal axis 601 of the stent 600 and the second peaks and second troughs are oriented non-parallel to the longitudinal axis 601 of the stent. Desirably, the peaks and troughs are oriented at an angle of at least 10 degrees with respect to the longitudinal axis of the stent. More desirably, the peaks and troughs are oriented at an angle of at least 15 degrees with respect to the longitudinal axis of the stent.

The first and second circumferential bands each define a pathway around the periphery of the stent and the first and second pathways are the same length.

The stent is further characterized by bent struts which exhibit a configuration similar to finger-like projections. Each of the bent struts may be characterized by a width. Optionally, the width of the bent struts of the first bands $W_1$ exceeds the width of the bent struts of the second bands $W_2$.

Desirably, as shown in FIG. 6a, bent struts which are circumferentially adjacent one another are parallel to one another. Bent struts in longitudinally adjacent first and second circumferential bands may or may not be parallel to one another, however.

In the embodiment shown in FIG. 6a, first and second circumferential bands which are longitudinally adjacent one another are connected by at least one connector 620 and desirably, by a plurality of connectors. Typically, the connectors will be substantially straight and non-parallel to the longitudinal axis 601 of the stent. In other embodiments of the invention, other types of connectors may be used for example connectors with one or more curves and/or connectors of different lengths. Desirably, as shown in FIG. 6a, the connectors extend from peaks of circumferential bands to troughs of adjacent circumferential bands. Also desirably, as shown in FIG. 6a, the connectors are similar in length to the longitudinal extent $L_2$ of the second circumferential bands.

Where a plurality of connectors are present between adjacent first and second circumferential bands, circumferentially adjacent connectors are joined via a first pathway along a first circumferential band and a second pathway along a second circumferential band, the first pathway desirably being of the same length as the second pathway.

In the embodiment of FIG. 6a, each first pathway traverses a total of four peaks and troughs (i.e. two peaks and two troughs) and each second pathway traverse a total of six peaks and troughs (i.e. three peaks and three troughs).

Figures 7A, 7B:
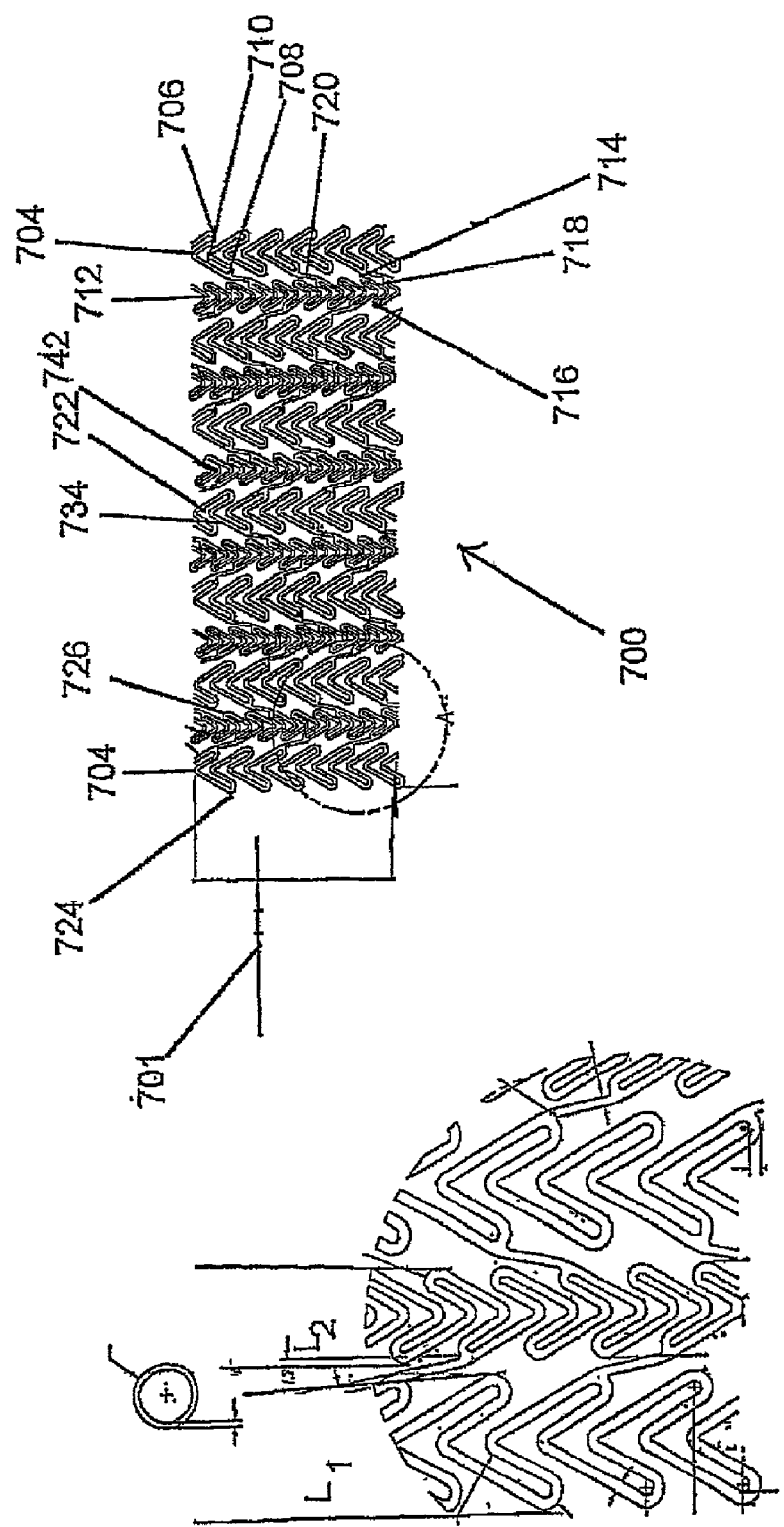

Yet another alternative embodiment of the inventive stent of the present invention is shown generally at 700 in FIG. 7a, the stent includes a plurality of circumferential bands wherein circumferential bands which are adjacent one another are connected one to the other. The circumferential bands include first circumferential bands 704 characterized by a first number of alternating first peaks 706 and first troughs 708 and second circumferential bands 712 characterized by a second number of alternating second peaks 714 and second troughs 716. The second number is different from the first number. The first peaks and troughs are oriented non-parallel to the longitudinal axis 701 of the stent 700 and the second peaks and second troughs are oriented non-parallel to the longitudinal axis 701 of the stent. Desirably, the peaks and troughs are oriented at an angle of at least 10 degrees with respect to the longitudinal axis of the stent. More desirably, the peaks and troughs are oriented at an angle of at least 15 degrees with respect to the longitudinal axis of the stent.

The first and second circumferential bands each define a pathway around the periphery of the stent and the first and second pathways are the same length.

The stent is further characterized as having bent struts exhibiting finger-like projections which are similar to those in the embodiment shown in FIG. 6a. Each of the bent struts may be characterized by a width. Optionally, the width of the bent struts of the first bands $W_1$ exceeds the width of the bent struts of the second bands $W_2$.

Desirably, as shown in FIG. 7a, bent struts which are circumferentially adjacent one another are parallel to one another. Bent struts in longitudinally adjacent first and second circumferential bands may or may not be parallel to one another, however.

In the embodiment shown in FIG. 7a, first and second circumferential bands which are longitudinally adjacent one another are connected by at least one connector 720 and desirably, by a plurality of connectors. Typically, the connectors are slightly curvilinear and are non-parallel to the longitudinal axis 701 of the stent. In other embodiments of the invention, other types of connectors may be used for example connectors with one or more curves and/or connectors of different lengths. Desirably, as shown in FIG. 7a, the connectors extend from peaks of circumferential bands to troughs of adjacent circumferential bands. Also desirably, as shown in FIG. 7a, the connectors are shorter in length than the longitudinal extent $L_2$ of the second circumferential bands.

Where a plurality of connectors are present between adjacent first and second circumferential bands, circumferentially adjacent connectors are joined via a first pathway along a first circumferential band and a second pathway along a second circumferential band, the first pathway desirably being of the same length as the second pathway.

In the embodiment of FIG. 7a, each first pathway traverses a total of four peaks and troughs (i.e. two peaks and two troughs) and each second pathway traverse a total of six peaks and troughs (i.e. three peaks and three troughs).

Figure 8A:
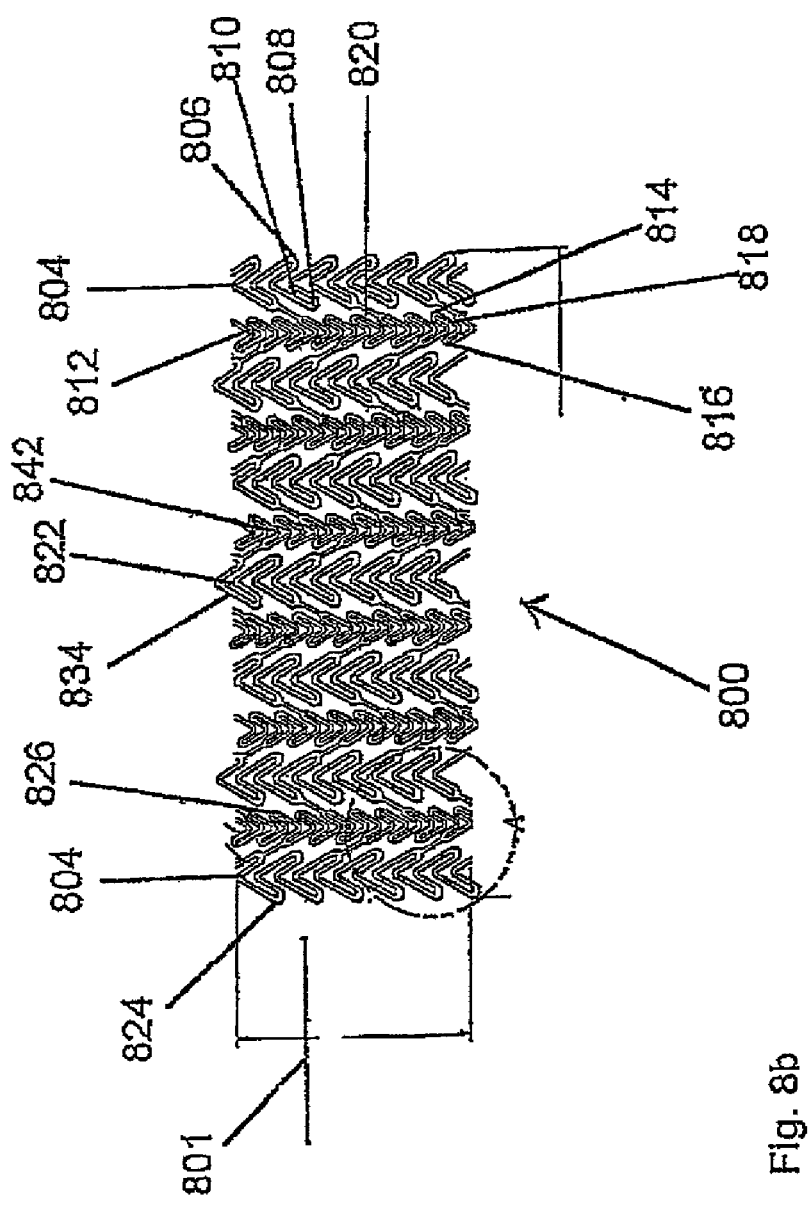
FIG. 8a is a flat layout view of an embodiment of the inventive stent of the present invention.
Figure 8B:
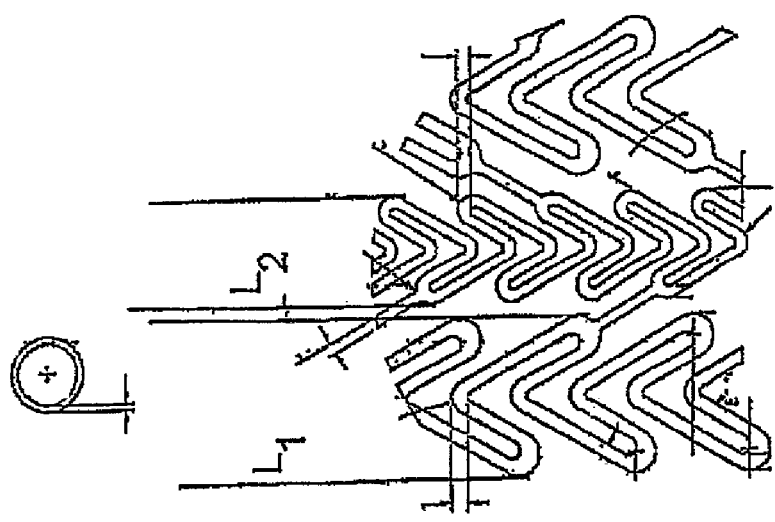

An alternative embodiment of the inventive stent of the present invention is shown in FIG. 8a. In this embodiment, the stent is substantially similar to that shown in FIG. 7a. The connectors 820 shown in the embodiment in FIG. 8a are straight while those shown in FIG. 7a are slightly curvilinear. The connectors 820 are again shorter in shorter in length than the longitudinal extent $L_2$ of the second circumferential bands.

Again, a plurality of connectors are shown present and between adjacent first and second circumferential bands. The circumferentially adjacent connectors are again joined via a first pathway along a first circumferential band and a second pathway along a second circumferential band, the first pathway desirably being of the same length as the second pathway. Again in the embodiment of FIG. 8a, each first pathway traverses a total of four peaks and troughs (i.e. two peaks and two troughs) and each second pathway traverse a total of six peaks and troughs (i.e. three peaks and three troughs).

Figure 9A:
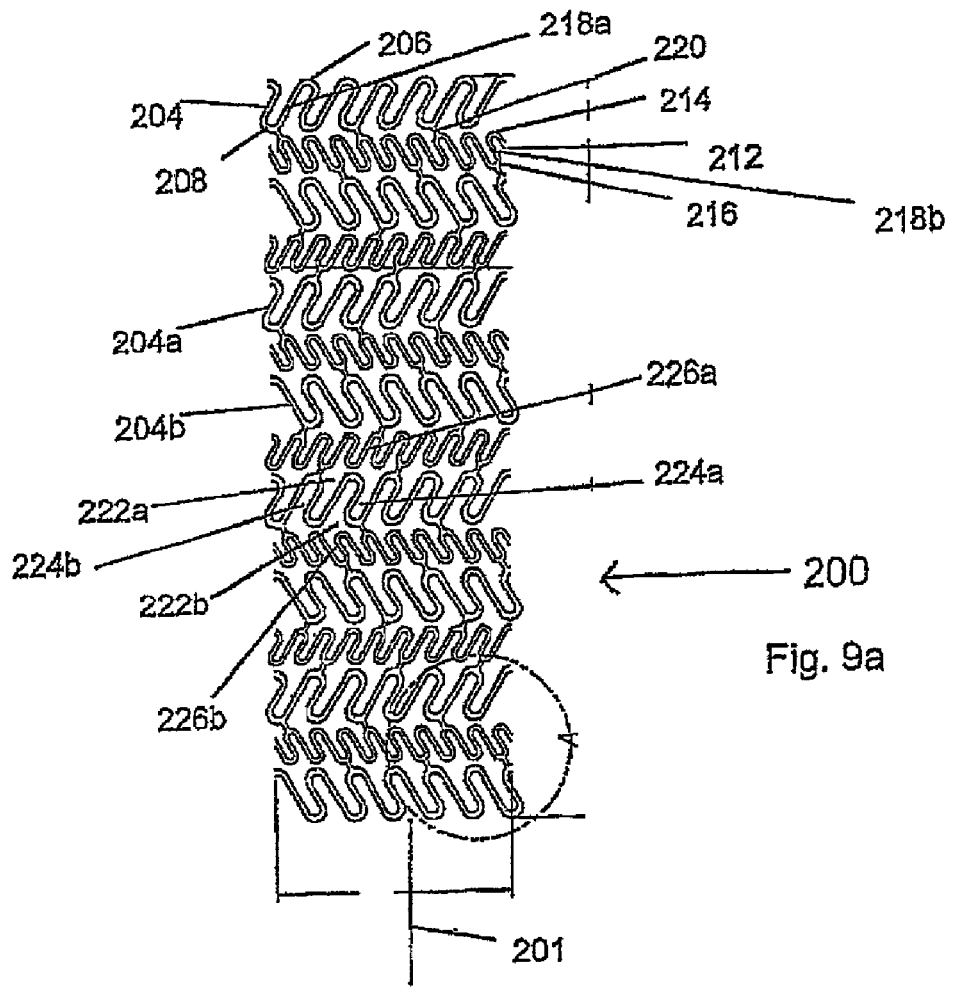
FIG. 9a is a flat layout view of an inventive stent of the present invention.
Figure 9B:
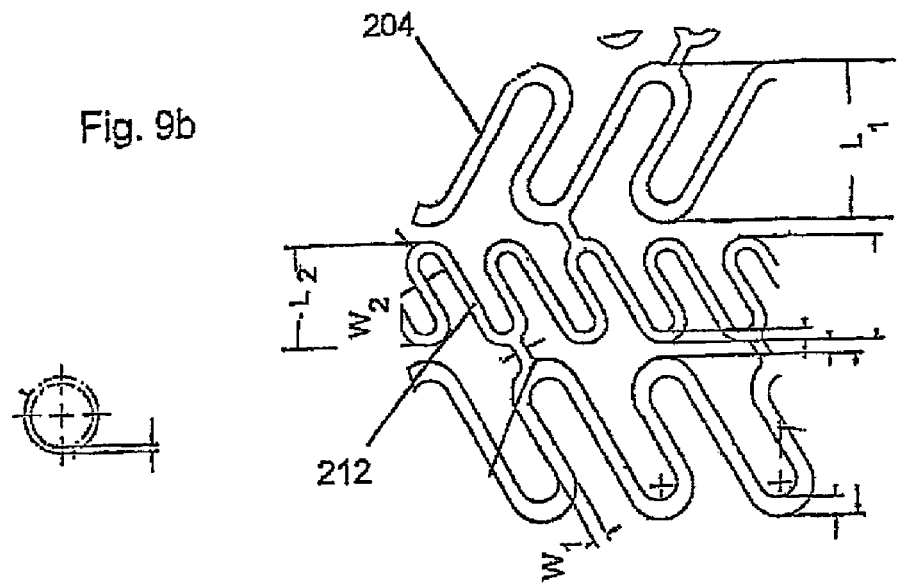

Desirably, as shown in FIG. 9b, the first and second circumferential bands 204 and 212 are each characterized by a longitudinal extent with the longitudinal extent $L_1$ of each the first circumferential bands exceeding the longitudinal extent $L_2$ of the second circumferential bands.

In yet another embodiment, as shown generally at 200 in FIG. 9a, the invention is directed to a stent including a plurality of circumferential bands where circumferential bands which are adjacent one another are connected one to the other. The circumferential bands include first circumferential bands 204 characterized by a first number of alternating first peaks 206 and first troughs 208 and second circumferential bands 212 characterized by a second number of alternating second peaks 214 and second troughs 216. The second number is different from the first number. The first peaks and troughs are oriented non-parallel to the longitudinal axis 201 of the stent and the second peaks and second troughs are oriented non-parallel to the longitudinal axis of the stent. Desirably, the peaks and troughs are oriented at an angle of at least 10 degrees with respect to the longitudinal axis of the stent. More desirably, the peaks and troughs are oriented at an angle of at least 15 degrees with respect to the longitudinal axis of the stent. Optionally, the first and second circumferential bands each define a pathway around the periphery of the stent and the first and second pathways are the same length.

Desirably, as shown in FIG. 9b, the first and second circumferential bands 204 and 212 are each characterized by a longitudinal extent with the longitudinal extent $L_1$ of each the first circumferential bands exceeding the longitudinal extent $L_2$ of the second circumferential bands.

Also desirably, first peaks and first troughs which are circumferentially adjacent one another are connected by struts 218a and second peaks and second troughs which are circumferentially adjacent one another are connected by struts 218b. Each of the struts is characterized by a width with the width $W_1$ of the struts of the first circumferential bands exceeding the width $W_2$ of the struts of the second circumferential bands.

Typically, as shown in FIG. 9a, struts which are circumferentially adjacent one another are parallel to one another.

First and second circumferential bands which are longitudinally adjacent one another may be connected by a single connector or by a plurality of connectors. The connectors may be of any shape. In one embodiment, as shown in FIG. 9a, straight connectors 220 may be used. The connectors may be oriented non-parallel to the longitudinal axis, as shown in FIG. 9b or, in another embodiment, oriented parallel to the longitudinal axis.

The connectors may extend from any region of one circumferential band to any region of an adjacent circumferential band. In the embodiment of FIG. 9a, the connectors extend from peaks of circumferential bands to troughs of adjacent circumferential bands. In the embodiment of FIG. 9a, first and second circumferential bands 204 and 212 which are longitudinally adjacent one another are connected by a plurality of connectors 220 and the connectors are shorter in length than the longitudinal extent $L_2$ of the second circumferential bands. Circumferentially adjacent connectors may be joined via a first pathway along a first circumferential band and a second pathway along a second circumferential band with the first pathway desirably being of the same length as the second pathway.

Desirably, as shown in FIG. 9a, the struts 218a in first circumferential bands which are longitudinally adjacent one, for example first circumferential bands 204a and 204b, are non-parallel to one another. More desirably, as shown in FIG. 9a, the struts in first circumferential bands which are longitudinally adjacent one another slant in opposing directions relative to the longitudinal axis of the stent. Without being bound by theory, the alternating orientation of adjacent first circumferential bands is believed to prevent significant rotation and build-up of torque and the accompanying degradation of stent performance.

In another embodiment of the invention, the first circumferential bands are connected to the second circumferential bands via straight connectors which extend between portions of similar curvature on adjacent circumferential bands. As shown by way of example in FIG. 10a, connectors 220a extend between peaks 206 of first circumferential band 204a and peaks 214 of second circumferential band 212. Connectors 220b extend between troughs 216 of second circumferential band 212 and troughs 208 of first circumferential bands 204b.

Figure 10A:
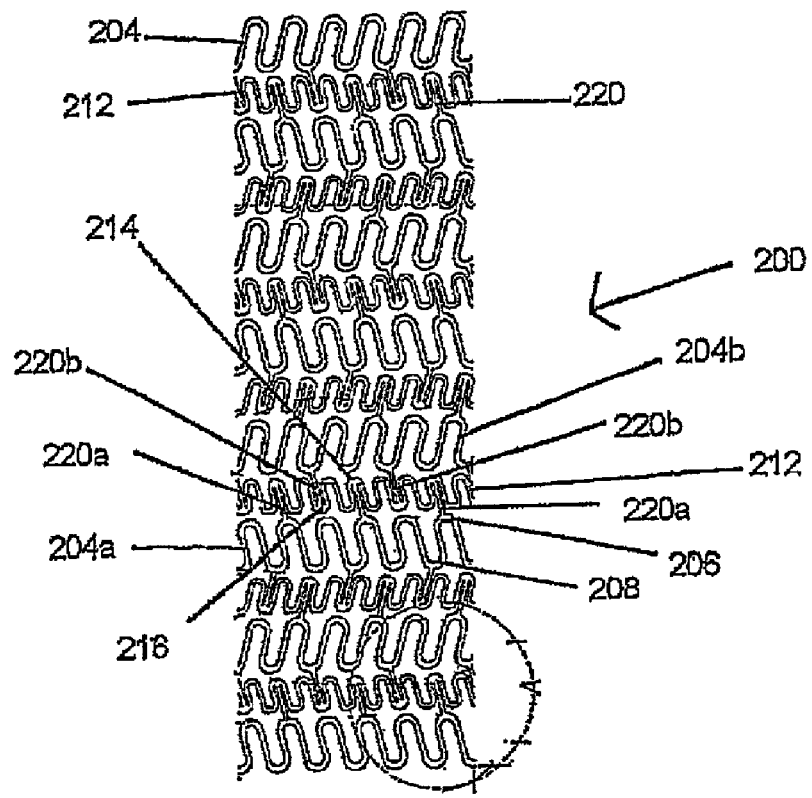
FIG. 10a is a flat layout view of an inventive stent of the present invention.
Figure 10B:
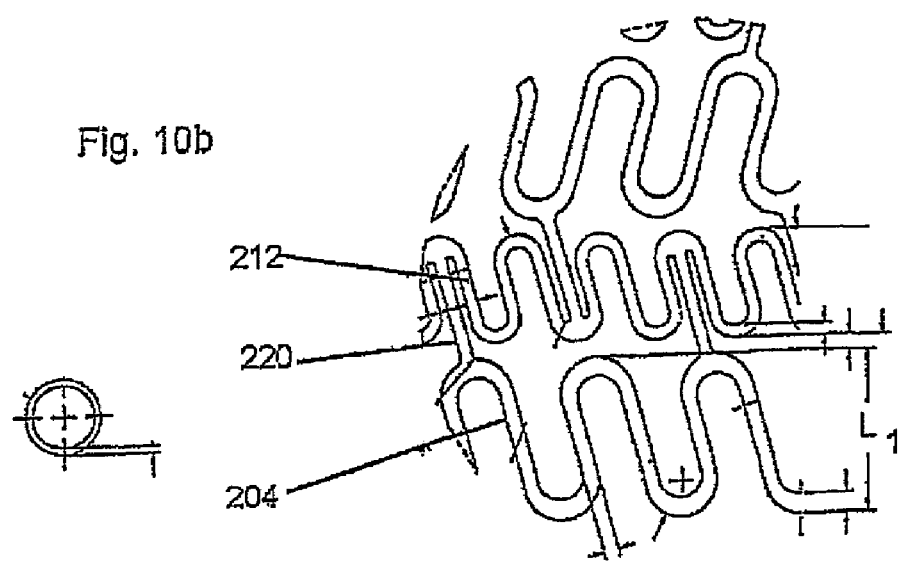

In the embodiment of FIG. 10a, connectors 220a and 220b are shorter in length than the longitudinal extent $L_1$ of first circumferential bands 204 but longer than the connectors of the embodiment of FIG. 10a. In other embodiments of the invention, longer connectors may be used. Any of the other connectors disclosed herein may also be used to achieve different properties.

Figure 11:
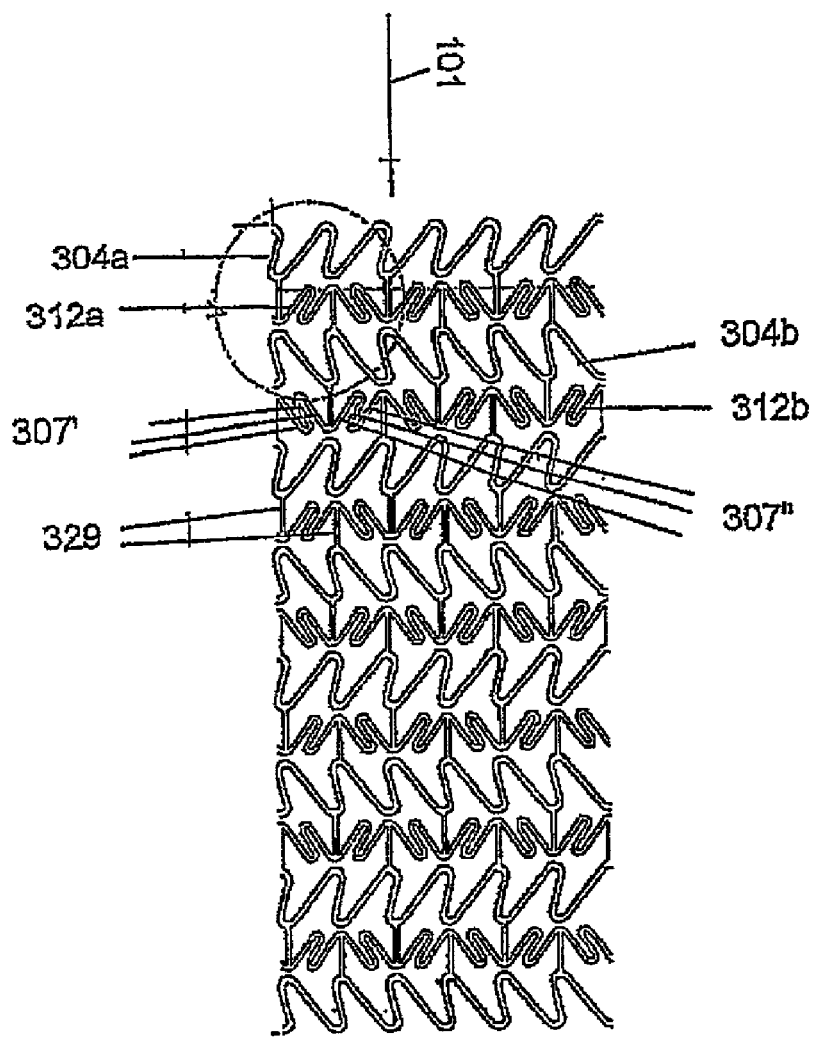
FIG. 11 shows a flat layout view of an alternative embodiment of the inventive stent of the present invention.

The invention is also directed to other embodiments in which the orientation of the struts in the first circumferential bands alternates between consecutive first circumferential bands relative to the longitudinal axis. In the embodiment of FIG. 11, the orientation of the struts in adjacent first circumferential bands 304a,b relative to the longitudinal axis alternates. Moreover, each second circumferential band 312a,b may comprise a plurality of consecutive struts 307' oriented in a first direction relative to the longitudinal axis of the stent and a plurality of consecutive struts 307" oriented in a second direction opposite the first direction and relative to the longitudinal axis of the stent. Adjacent circumferential bands are connected via connectors 329. Desirably, in the embodiment of FIG. 11, the connectors are oriented longitudinally. Any of the other connectors disclosed herein may be used to achieve stents with other characteristics.

First circumferential bands 304a,b may be longer or the same length about the periphery of the stent as second circumferential bands 312a,b. First circumferential bands 304a,b are desirably wider than second circumferential bands 312a,b. Also desirably, the first circumferential bands have fewer peaks and troughs than the second circumferential bands.

It is further within the scope of the invention to vary the number of connectors extending between adjacent circumferential bands in any of the embodiments disclosed herein. For example, adjacent circumferential bands in the middle of the stent may be joined by more connectors than adjacent circumferential bands at the proximal and/or distal ends of the stent so that the proximal and/or distal ends of the stent are more flexible. The middle portion of the stent may have fewer connectors than the proximal and/or distal ends of the stent to achieve greater flexibility in the middle of the stent than in the proximal and/or distal ends of the stent. The number of connectors may increase over the length of the stent to provide a stent with increasing rigidity over its length.

The invention is also directed to a stent such as that shown by way of example in FIG. 1a, comprising a sidewall with a plurality of openings 122 therein. Each opening is bounded by at least a first stent member and a second stent member. The first stent member 134 (shown shaded) is of a larger width than the second stent member 142 (shown shaded). The first stent member 134 comprises a plurality of bent first struts 110 which extend non-parallel to the longitudinal axis 101 of the stent and the second stent member 142 comprises a plurality of bent second struts 118 which extend non-parallel to the longitudinal axis of the stent. The bent first struts define finger like first projections 124 (shown shaded) which are non-parallel to the longitudinal axis of the stent and the bent second struts define finger like second projections 126 which are non-parallel to the longitudinal axis of the stent with the number of first projections exceeding the number of second projections.

Desirably, as shown in the embodiment of FIG. 1a, each opening is defined by first projections which are non-parallel to second projections.

In another embodiment, as shown by way of example in FIG. 9a, the stent comprises a plurality of openings including first openings 222a and second openings 222b. Each first opening 222a includes first projections 224a which are parallel to second projections 226a. Each second opening 222b includes first projections 224b which are non-parallel to second projections 226b.

The stent of FIG. 9a also has first openings and second openings where each first opening includes first projections which are parallel to second projections. Each second opening includes first projections which are non-parallel to second projections.

In another embodiment, the invention is directed to a stent such as that shown at 100 in FIG. 12 comprising a plurality of circumferential bands. Circumferential bands which are adjacent one another are connected one to the other. At least a portion of the stent, and, desirably, as shown in FIG. 12, the entirety of the stent consists of first circumferential bands 104 characterized by a first number of alternating first peaks 106 and first troughs 108 joined by bent struts 110 and second circumferential bands 112 characterized by a second number of alternating second peaks 114 and second troughs 116 joined by bent struts 118. Typically, as shown in FIG. 12, the second number of second peaks and troughs is different from the first number of first peaks and troughs and desirably exceeds the first number. First circumferential bands which are adjacent to second circumferential bands are connected thereto by at least one, and desirably, as shown in FIG. 12, a plurality of connectors 120. Connectors 120 extend from troughs of first circumferential bands to troughs of second circumferential bands and from peaks of second circumferential bands to peaks of first circumferential bands. Connectors 120 are bent and are generally parallel to the struts of the first circumferential bands.

In the embodiment of FIG. 12, with the exception of the connectors of the end bands, each connector which extends in distal direction is separated by one struts 110 from a connector extending in a distal direction.

In the embodiment of FIG. 13, adjacent first circumferential bands 104 and second circumferential bands 112 are connected to one another via one and desirably a plurality of connectors 120 which extend from peaks 106 of first circumferential bands to troughs 16 of second circumferential bands 112 and from peaks 114 of second circumferential bands 112 to troughs 108 of first circumferential bands 104. Connectors 120 are desirably significantly shorter than the struts of the second circumferential band 112. More desirably, the length of connectors 120 is on the order of magnitude of the width of the struts 110 of first circumferential band 104. As shown in FIG. 13, each connector which extends in a distal direction is separated from a connector extending in a proximal direction by three struts. Connectors 120 are straight and oriented parallel to the longitudinal axis.

In the embodiment of FIG. 13, as well as in many of the other embodiments of the invention, connectors 120 do not extend from the center of the peaks and troughs but rather extend from corners of the peaks and troughs. In the embodiment of FIG. 12, connectors extend from the center of the peaks and troughs.

The individual sections 110a and 110b of bent struts 110 of the inventive stent of FIG. 13 extend at a more gradual angle relative to the longitudinal axis of the stent than the individual sections of the bent struts of the stent of FIG. 12. Specifically, the sections of the bent struts of the stent of FIG. 12 extend at a 40 degree angle relative to the longitudinal axis and the sections of the bent struts of the stent of FIG. 13 extend at a 30 degree angle relative to the longitudinal axis.

Depending on the alignment of adjacent circumferential bands, the connectors may also be at an angle relative to the longitudinal axis as shown in FIG. 14. Connectors 120 are non-parallel to the longitudinal axis, extending at an oblique angle relative to the longitudinal axis. In the stent of FIG. 14, the orientation of connectors relative to the longitudinal axis reverses along the length of the stent with connectors 120a extending in a first direction and connectors 120b extending in a second opposite direction relative to the longitudinal axis of the stent.

Figure 15:
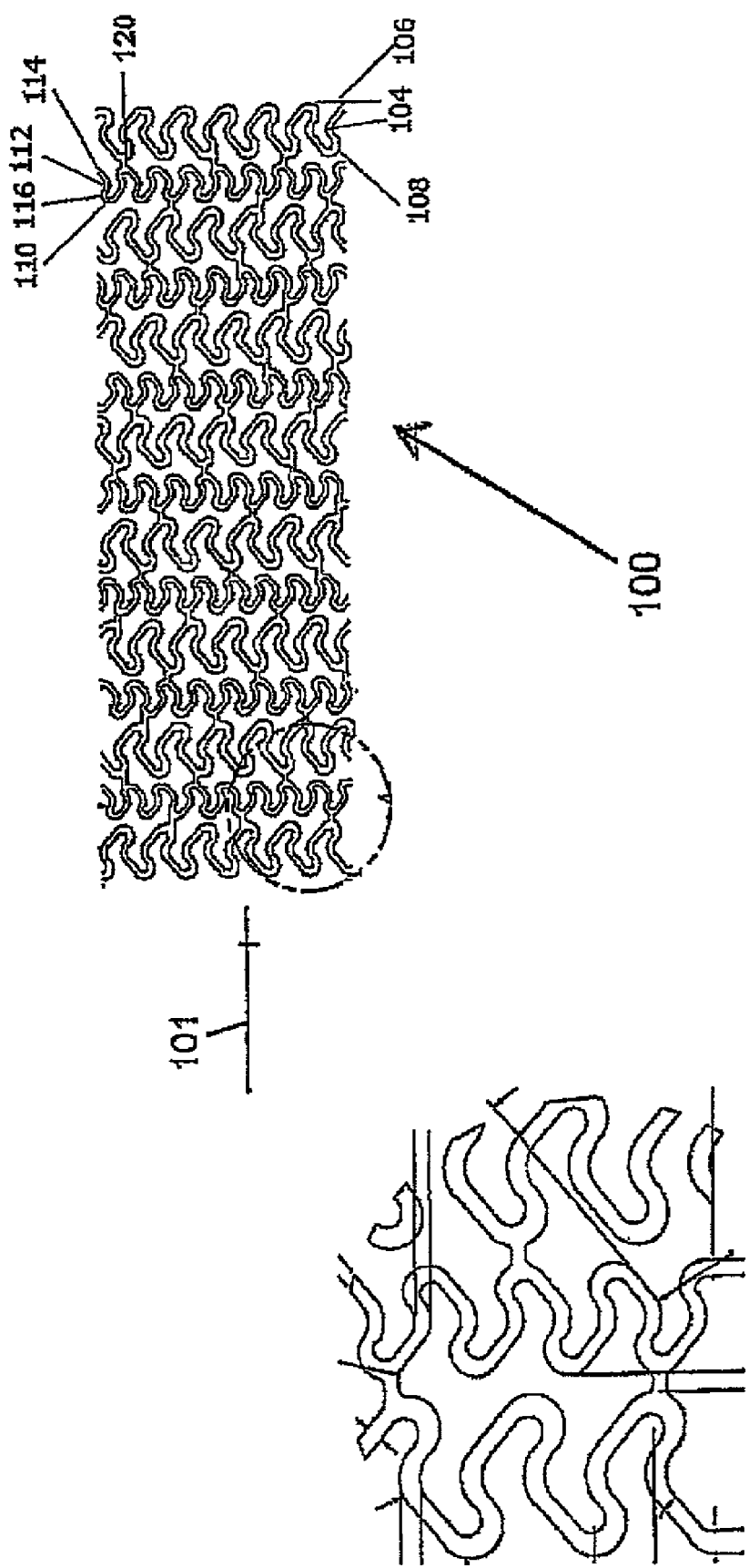
Figure 22:
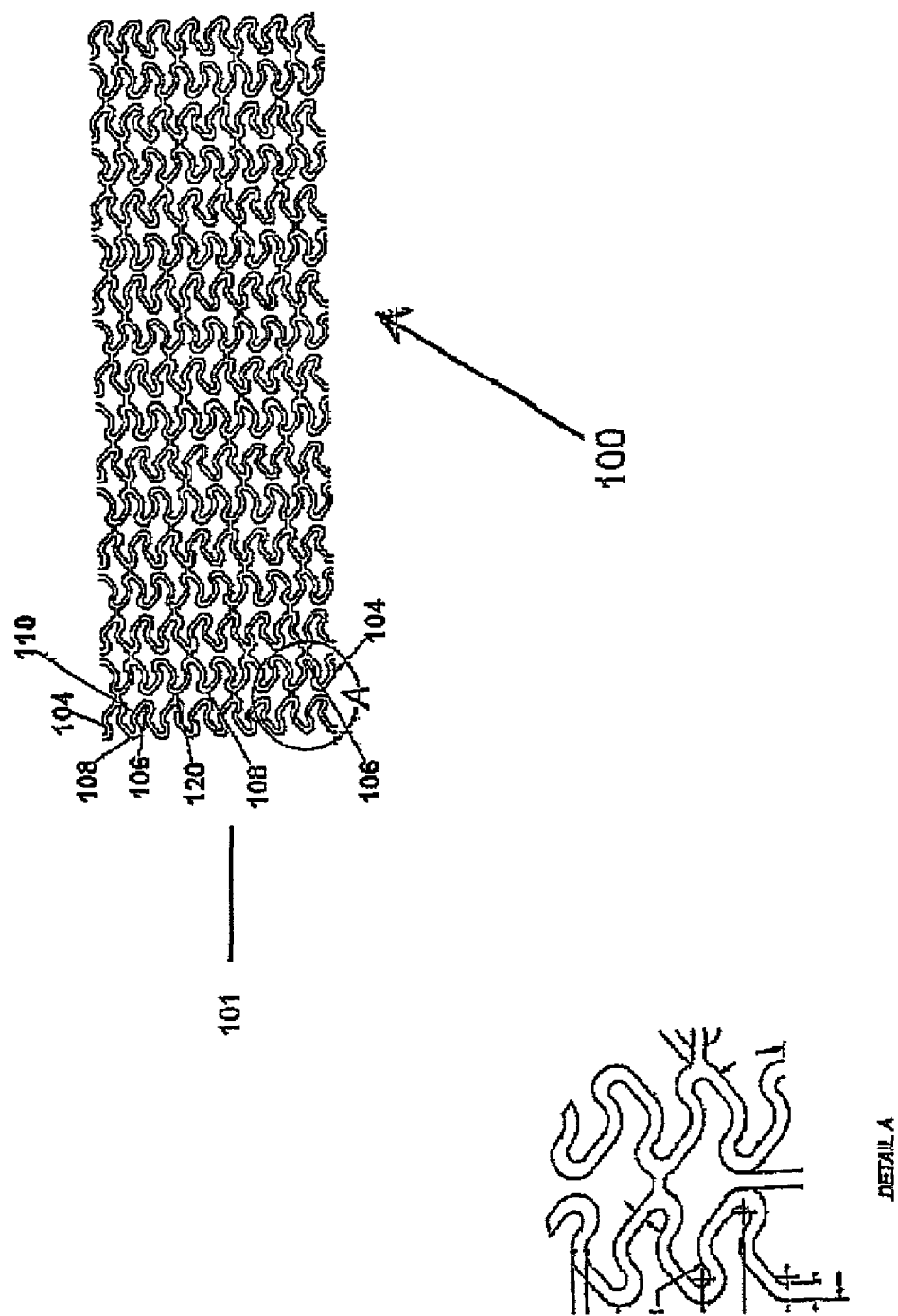

In the embodiment of FIG. 15, the sections 110a and 110b of the bent struts 110 extend at a 40 degree angle relative to the longitudinal axis of the stent. Straight connectors 120 are provided between adjacent circumferential bands 104 and 112.

In the embodiment of FIG. 16, adjacent first and second circumferential bands 104 and 112 are spaced further apart from one another than in some of the previous embodiments. As a result, connectors 120 are longer than in other embodiment where the connectors extend between peaks and troughs. Also, the bent struts 110 of the first circumferential bands 104 are much closer in width to the bent struts 110 of the second circumferential bands 112.

FIG. 17 is an embodiment with narrower bent struts in the first circumferential bands and with connectors 120 which are parallel to the longitudinal axis of the stent.

The embodiment of FIG. 18 is similar to that of FIG. 17, differing in part in that the sections of the bent struts extend at a 40 degree angle relative to the longitudinal axis rather than the 30 degree angle of the struts of FIG. 17.

The stent of FIG. 19 comprises first circumferential bands 104 which have bent struts 110 and second circumferential bands 112 which have relatively straight struts which are not parallel to the longitudinal axis of the stent. The orientation of the struts of the second circumferential bands reverses along the length of the stent. Connectors 120 extend from peaks 106 of first circumferential bands 104 to peaks 114 of second circumferential bands 112 and from troughs 116 of second circumferential bands 112 to troughs 108 of first circumferential bands 104.

In the embodiment of FIG. 20, adjacent circumferential bands 104 are of the same longitudinal extent and have an identical number of peaks 106 and an identical number of troughs 108. Connectors 120 extend from peaks 106 of circumferential bands 104 to troughs 108 of adjacent circumferential bands 104 and from troughs 106 of circumferential bands 104 to peaks 106 of adjacent circumferential bands 104. The connectors 120 are parallel to the longitudinal axis of the stent.

Figure 31:
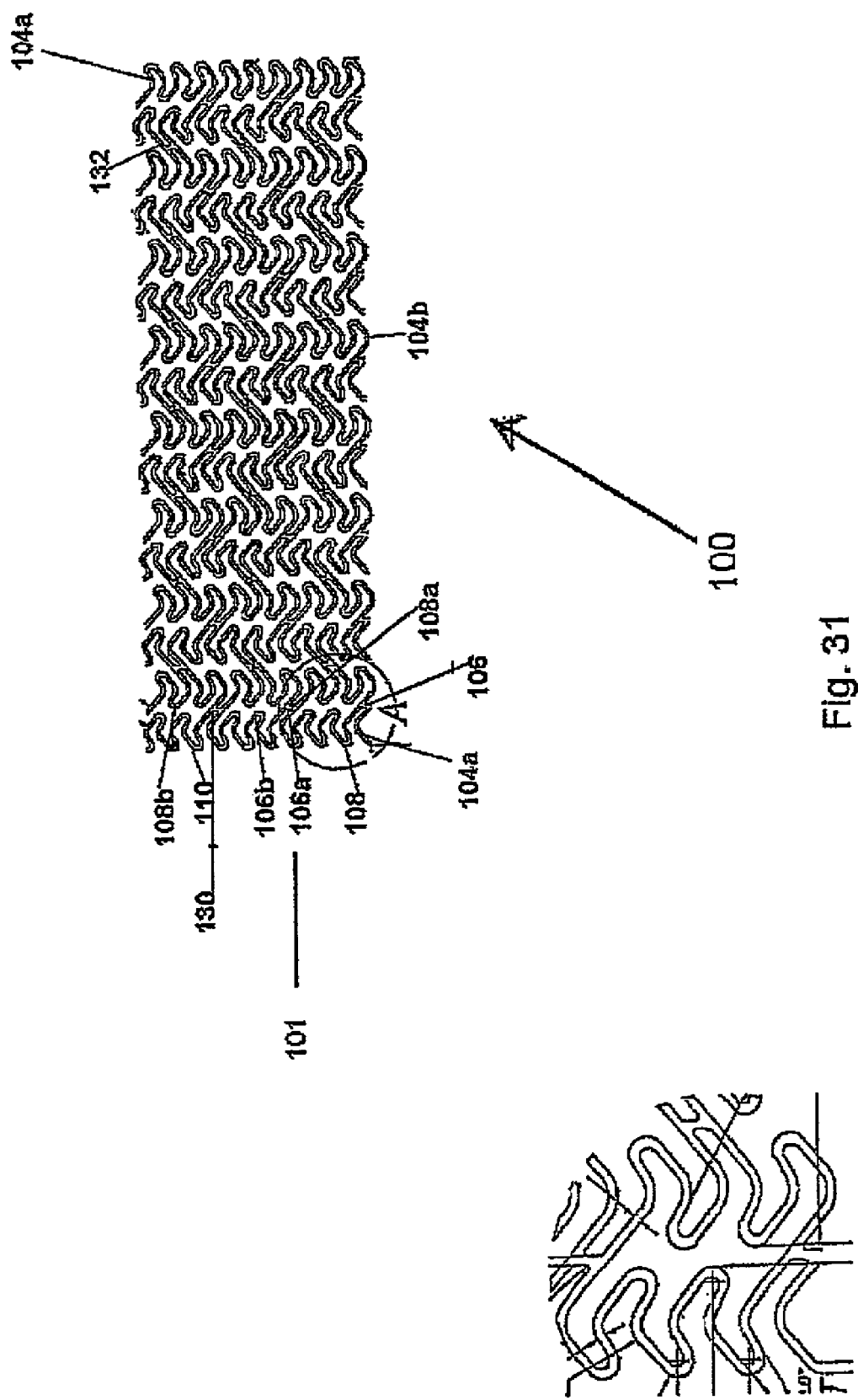
Figure 36:
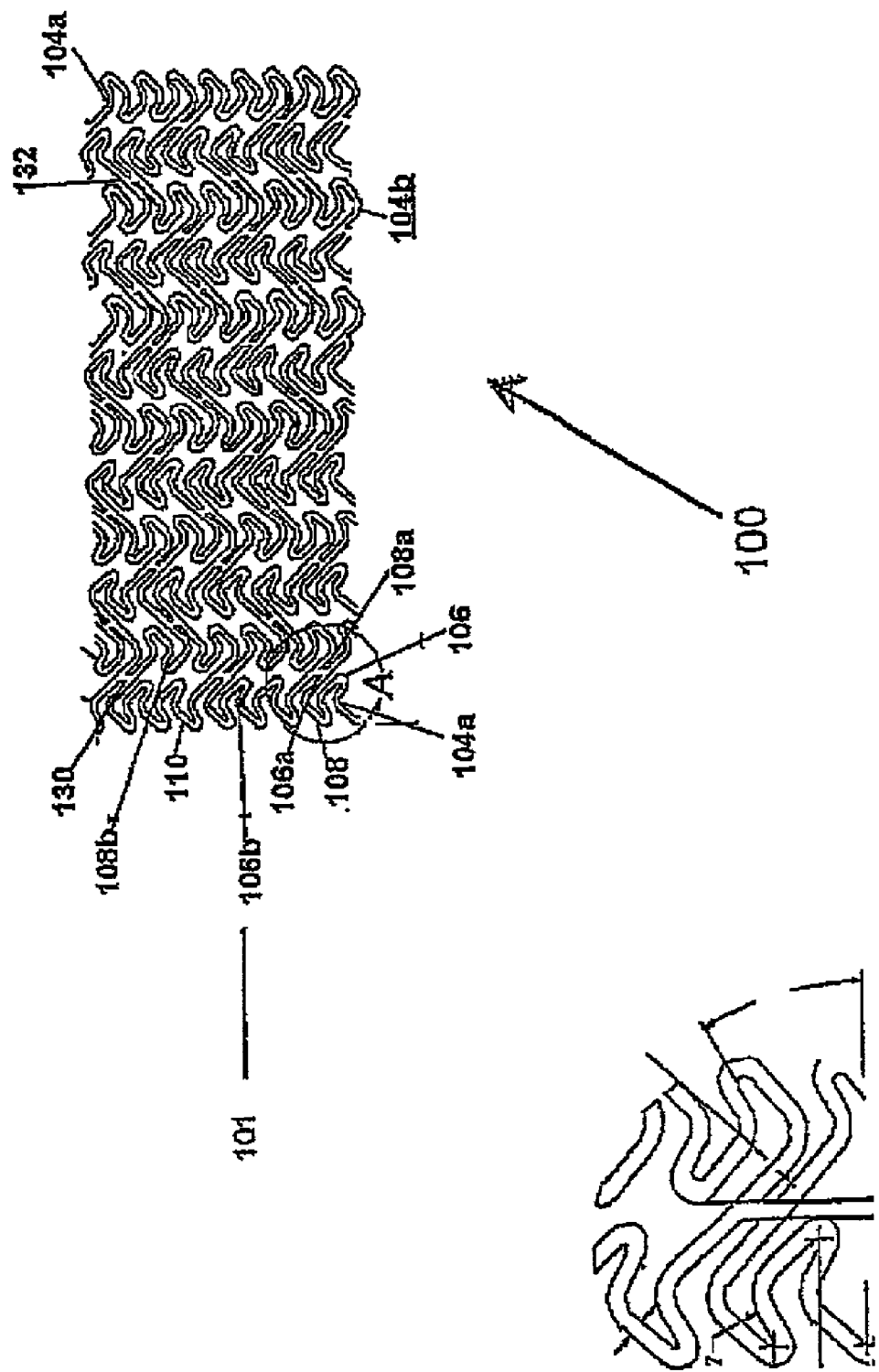

In the embodiment of FIG. 26, adjacent circumferential bands 104 share one or more members 130 in common. One or more peaks 106a of one circumferential band 104 are longer than the remaining peaks 106b and one or more troughs 108a of the adjacent circumferential band 104 are longer than the remaining troughs 108b. The longer peaks 106a intersect with the longer troughs 108a and share a member 130 in common forming an H-shaped structure 132. The resulting H-shaped structure in the embodiment of FIG. 26 is oriented at an oblique angle relative to the longitudinal axis of the stent with the cross-bar portion 130 of the 'H' shaped structure extending in a circumferential direction. In other embodiments of the invention, cross-bar portion 130 of the H-shaped member is oriented in a longitudinal direction, as shown for example in FIG. 30, or in a circumferential direction, as shown for example, in FIG. 31.

Figure 27:
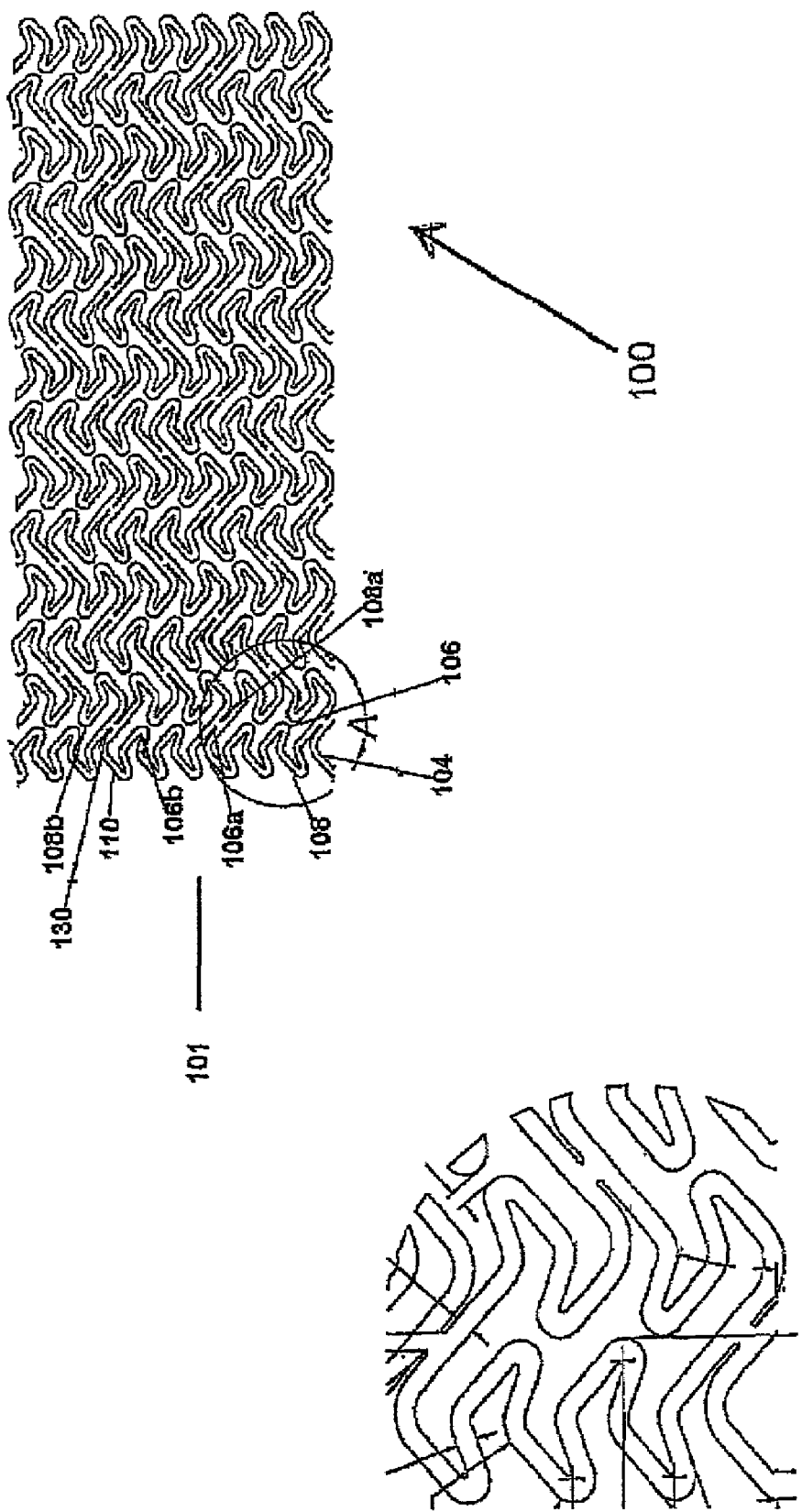
Figure 28:
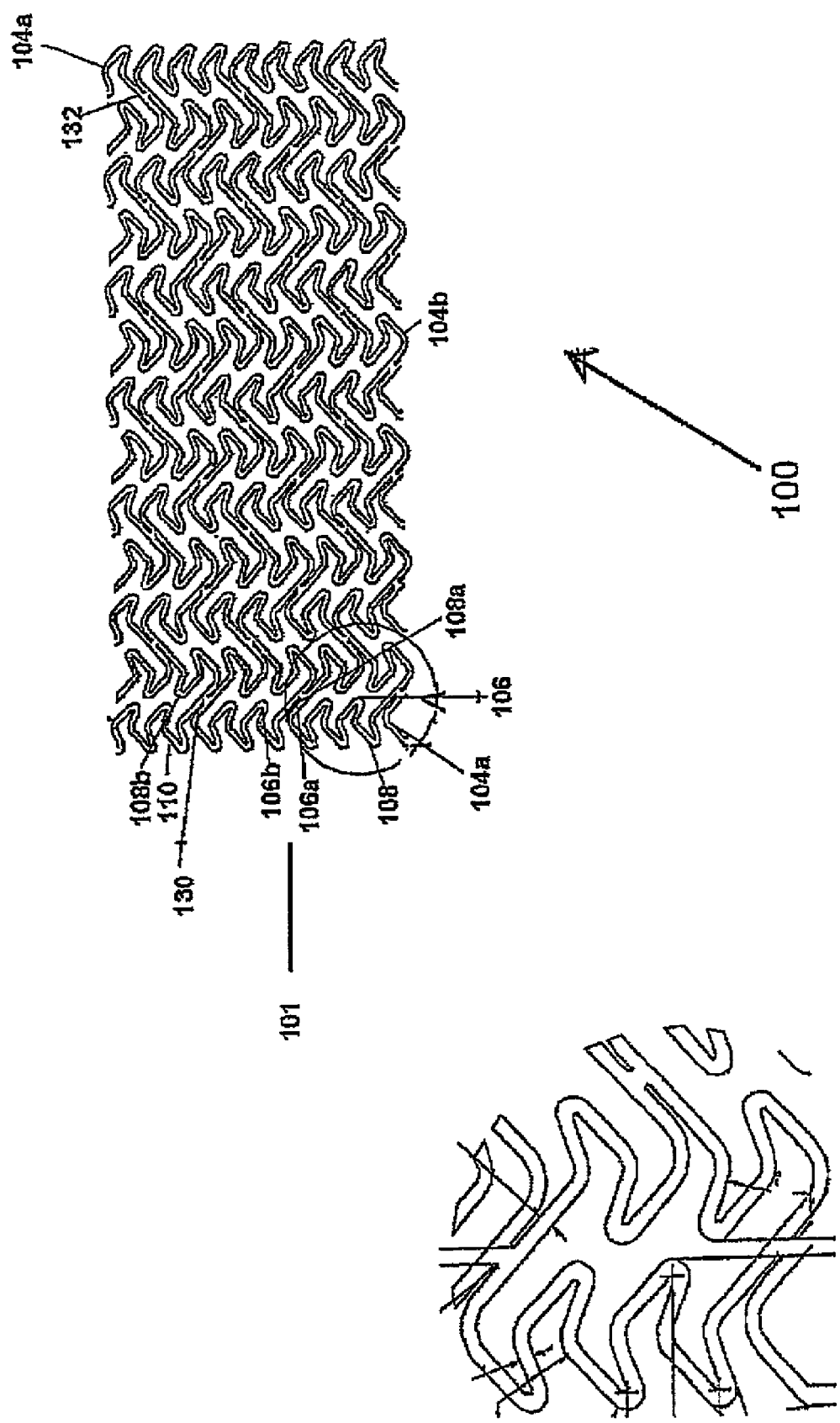
Figure 29:
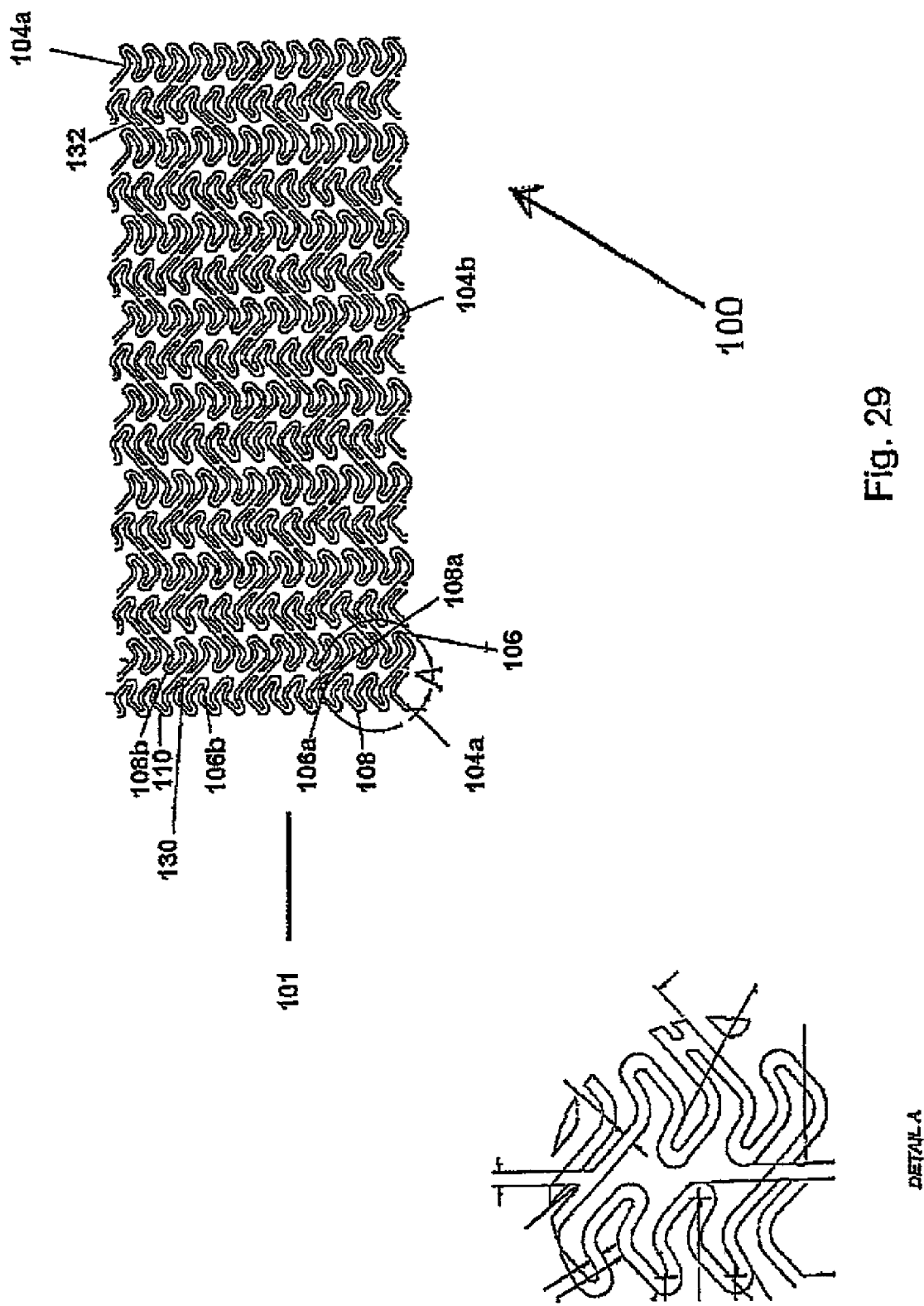

In the embodiment of FIG. 26, there are three overlapping regions 130 between adjacent circumferential bands 104. The distal end of each cell 136 is defined by two full peaks 106 and two full troughs 108 and the proximal end of each cell 136 is defined by two full peaks 106 and two full cells 136. It is also within the scope of the invention for there to be fewer overlapping regions 130 between adjacent circumferential bands 104 or more overlapping regions 130 between adjacent circumferential bands 104. In the embodiment of FIG. 27, there are four overlapping regions 130 between adjacent circumferential bands 104. The distal end of each cell 136 is defined by three full peaks 106 and three full troughs 108 and the proximal end of each cell 136 is defined by three full peaks 106 and three full troughs 136. The 'H' shaped structures 132 extend in an oblique direction relative to the longitudinal axis of the stent.

In the stents of FIGS. 26-37 it is also noted that the total circumferential length of the proximal and distal most circumferential bands 104a is less than the total circumferential length of the other circumferential bands 104b. Desirably, the difference in total circumferential length is on the order of 5%. In another embodiment of the invention, the proximal and distal most circumferential bands are of the same total circumferential length as the other circumferential bands. In another embodiment of the invention, the proximal and distal most circumferential bands are of greater total circumferential length than the other circumferential bands. In yet another embodiment of the invention only of the proximal and distal most circumferential bands are of greater total circumferential length than the other circumferential bands. In yet another embodiment of the invention only of the proximal and distal most circumferential bands are of lesser total circumferential length than the other circumferential bands. Finally, in yet another embodiment of the invention one of the proximal and distal most circumferential bands is of greater total circumferential length than the other circumferential bands and the other of the proximal and distal most circumferential bands is of lesser total circumferential length than the other circumferential bands.

Figure 43:
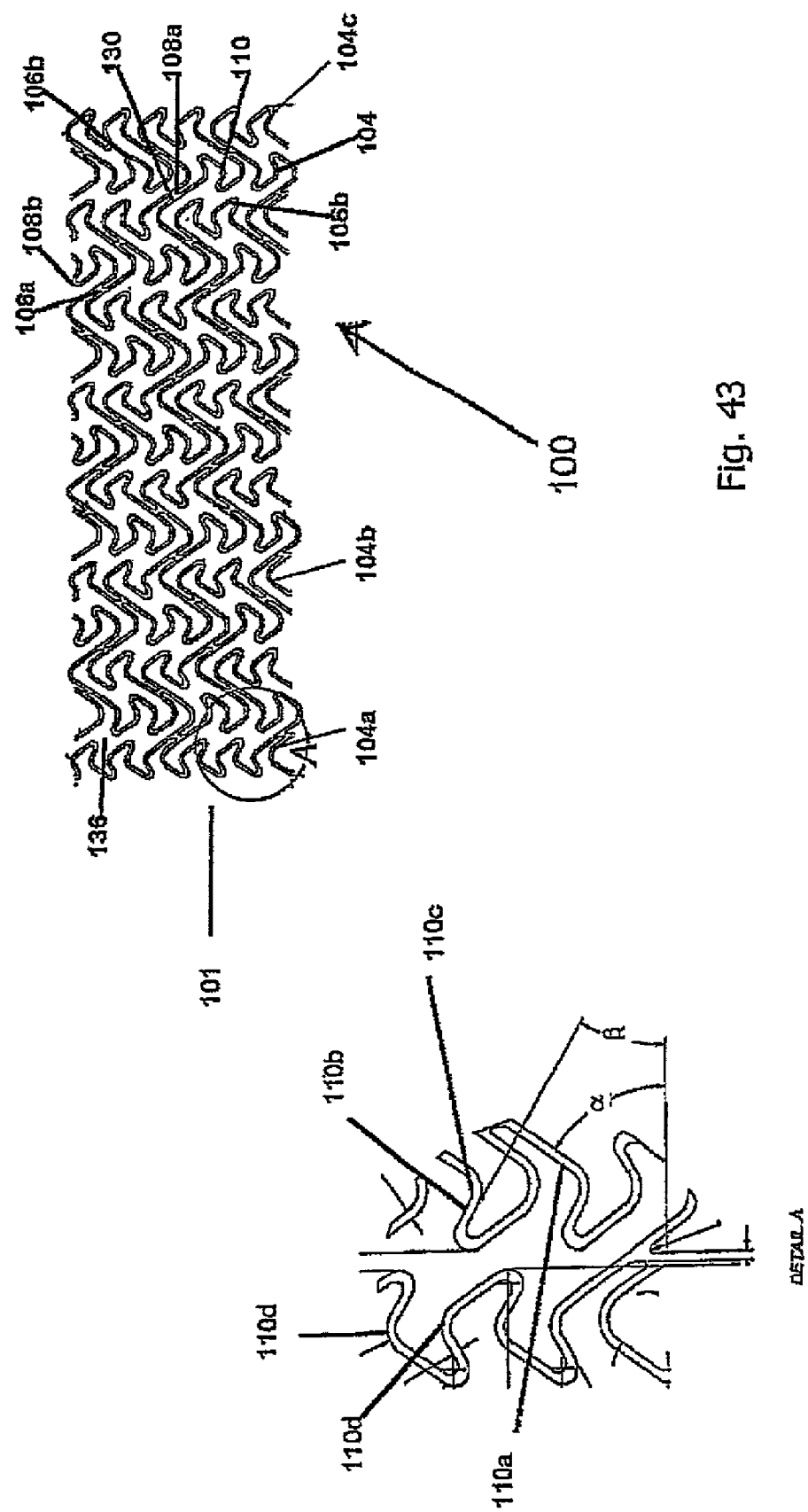
Figure 44:
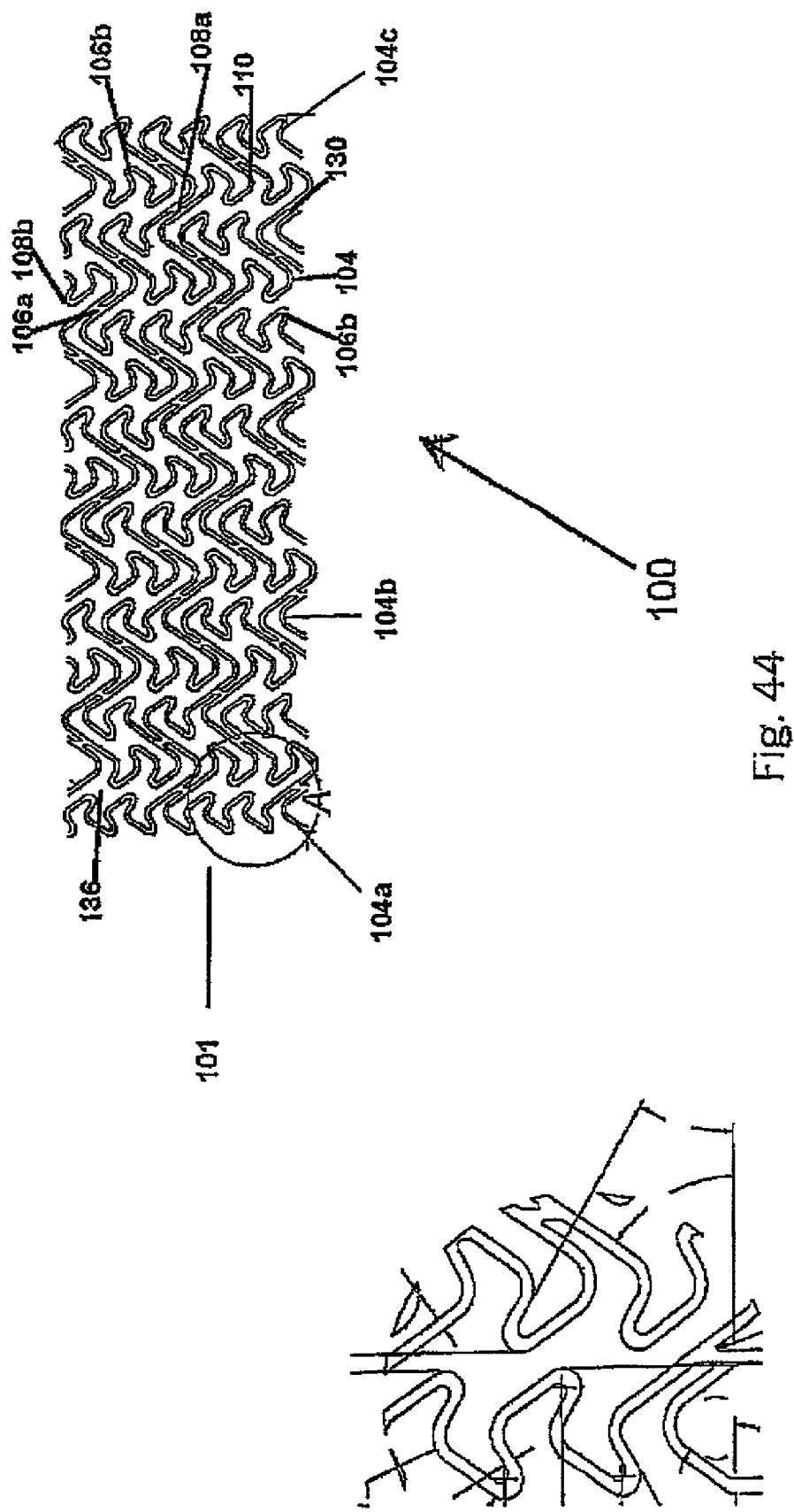

In the stents of FIGS. 43-45, the proximal-most and distal-most circumferential bands 104a,c are of different total circumferential lengths than the remainder of the circumferential bands 104b. In this case, they are shorter than the other circumferential bands 104b. Moreover, the proximal-most bands 104a are of shorter total length than the distal-most circumferential band 104c. In the stents of FIGS. 43-45, adjacent circumferential bands 104 have regions 130 of overlap. More generally, the invention is directed to stents comprising circumferential bands wherein the proximal-most and distal-most circumferential bands are of less total circumferential length than the remainder of the circumferential bands and one of the proximal-most and distal-most circumferential bands is shorter than the other. The circumferential bands may overlap one another or may be connected by connecting which extend through gaps separating adjacent circumferential bands.

The stents of FIGS. 43-45 is also notable in that the number of overlapping regions 130 alternates between 2 and 3 along the length of the stent. This results in alternating regions having three cells 136 extending about the circumference of the stent and regions having two cells 136 extending about the circumference of the stent. More generally, the invention is directed to stents having alternating numbers of overlapping regions or connections between adjacent bands along the length of the stent. Thus, the number of overlapping regions or connections between adjacent bands will alternate between N and M where N and M are different integers greater than or equal to 1. The invention is also directed to stents having alternating numbers of cells in circumferential bands along the length of the stent. Thus, the number of cells arranged about the circumference of the stent will alternate between N and M along the length of the stent where N and M are different integers greater than or equal to 1.

The stents of FIGS. 43-45 also have more cells disposed about the circumference at one end than at the other end.

The invention is also direct to a stent such as that shown by way of example in FIG. 12, comprising a plurality of circumferential bands, with adjacent circumferential bands connected one to the other via a plurality of connectors. The circumferential bands include first circumferential bands 104 characterized by a first number of alternating first peaks 106 and first troughs 108 joined by bent struts 110 and second circumferential bands 12 characterized by a second number of alternating second peaks 114 and second troughs 116 joined by bent struts 118. The second number is different from the first number. Each second circumferential band 112 is connected to one adjacent first circumferential band 104 via at least one connector 120 and desirably a plurality of connectors 120. The one or more connectors 120 extend from peaks 106 on the adjacent first circumferential band 104 to peaks 114 on the second circumferential band 112. Each second circumferential band 112 is also connected to another adjacent first circumferential band 104 via one or more connectors 120 extending from troughs 108 on the another first circumferential band 104 to troughs 116 on the second circumferential band 112.

Desirably, the connectors 120 are not straight. More desirably, as shown in FIG. 12, the connectors 120 are substantially parallel to the bent struts 110 of the first circumferential bands 104.

In the embodiment of FIG. 12, the first and second circumferential bands are each characterized by a longitudinal extent and the longitudinal extent of each first circumferential band 104 exceeds the longitudinal extent of each second circumferential band 112. It is also within the scope of the invention for the first and second circumferential bands to be of the same longitudinal extent.

Also, in the embodiment of FIG. 12, the first circumferential bands 104 are each characterized by a first total circumferential length and the second circumferential bands 112 are each characterized by a second total circumferential length and the first total circumferential length is equal to the second total circumferential length. In other embodiments of the invention, the first and second circumferential bands may be of different total circumferential lengths.

The invention is also directed to a stent, such as that shown by way of example in FIG. 43, comprising a plurality of serpentine circumferential bands 104. Adjacent serpentine circumferential bands 104 are connected one to the other. The serpentine circumferential bands 104 include a first serpentine circumferential band 104a having a first total circumferential length at a proximal end of the stent, a second serpentine circumferential band 104b having a second total circumferential length at a distal end of the stent and a third serpentine circumferential band 104c having a third total circumferential length between the proximal and distal ends of the stent. The first and second total circumferential lengths differ from one another. Desirably, the first, second and third total circumferential lengths differ from one another. More desirably, the first and second total circumferential lengths are less than the third total circumferential length.

As shown in FIG. 43, the serpentine circumferential bands include a band 104a of a first longitudinal extent and a band 104b of a second longitudinal extent different from, and desirably, less than the first longitudinal extent. The first longitudinal extent is greater than the second longitudinal extent.

The stent may optionally have serpentine circumferential bands having a first number of peaks and troughs and serpentine circumferential bands having a second number of peaks and troughs, the second number less than the first number, as shown for example in FIG. 12.

Desirably, as shown in FIG. 43, each serpentine circumferential band 104a-c comprises a plurality of peaks 106 and troughs 108 with bent struts 110 extending between adjacent peaks 106 and troughs 108. Circumferentially adjacent bent struts 110 are nested as they are in many other embodiments disclosed herein.

The invention is also directed to a stent such as that shown by way of example in FIG. 43, comprising a plurality of interconnected serpentine circumferential bands 104a-c, each comprising a plurality of peaks 106 and troughs 108. Adjacent peaks 106 and troughs 108 are connected by bent struts 110. The bent struts 110 are arranged in a nested relationship. The serpentine circumferential bands 104 include a first serpentine circumferential band 104a having a first total circumferential length at a proximal end of the stent, a second serpentine circumferential band 104b having a second total circumferential length at a distal end of the stent and a third serpentine circumferential band 104c having a third total circumferential length between the proximal and distal ends of the stent. At least one of the first and second total circumferential lengths differs from the third total circumferential length.

Desirably, as shown in FIG. 43, both the first and second total circumferential lengths differ from the third total circumferential length. More desirably, at least one of the first and second total circumferential lengths is less than the third total circumferential length.

Figure 38:
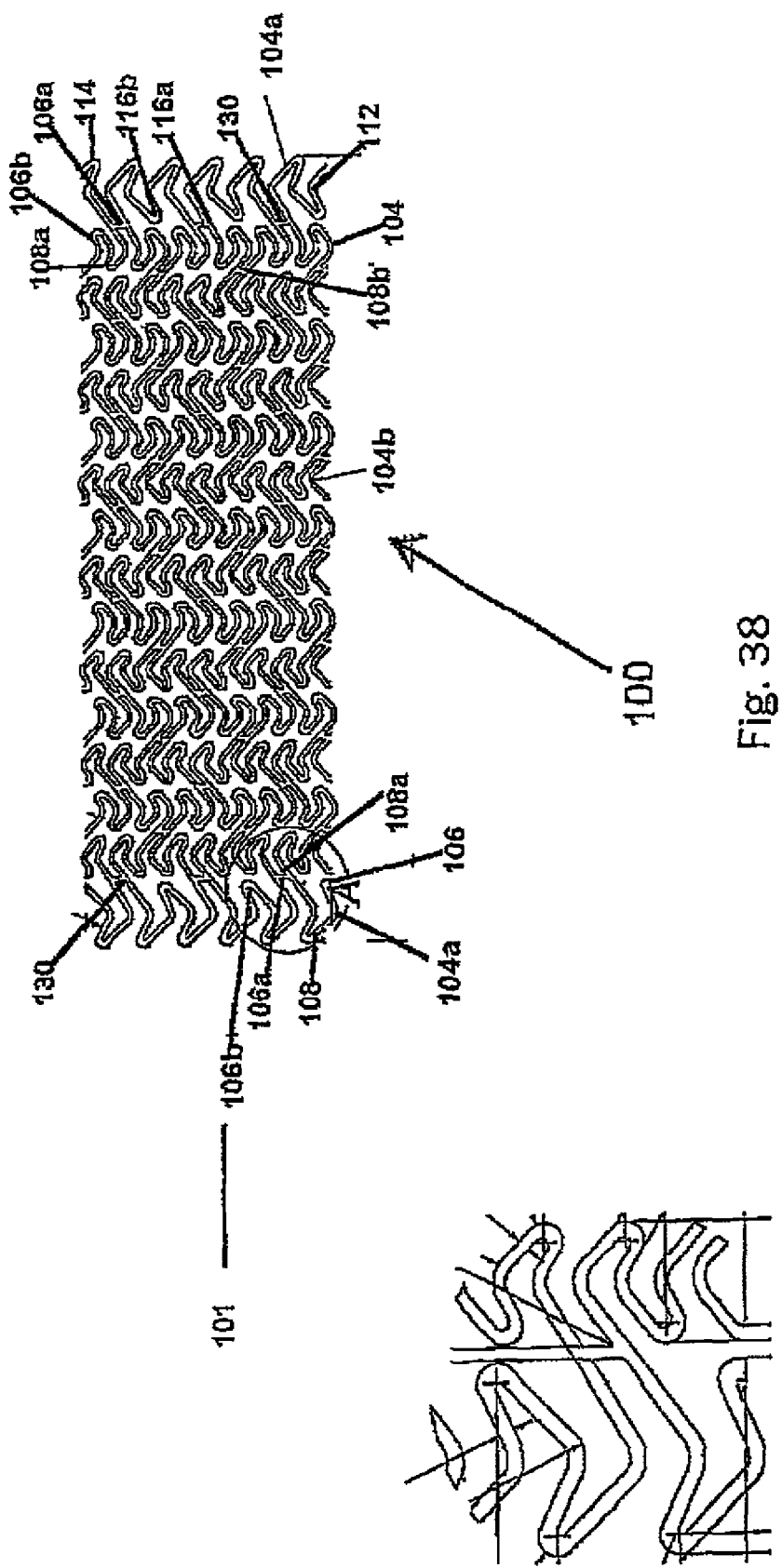
Figure 42:
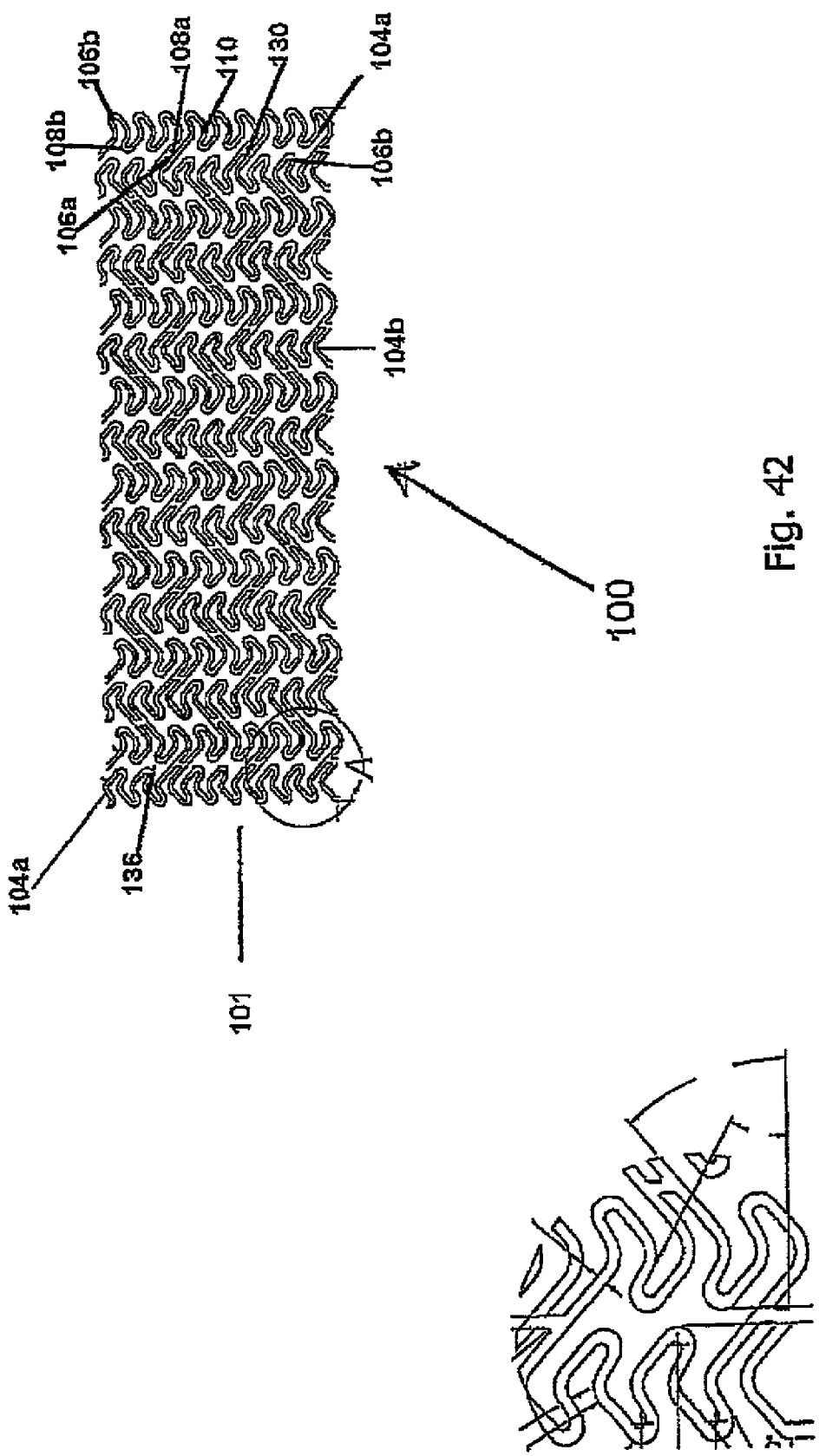

Adjacent serpentine circumferential bands may be connected by connectors extending from peaks to troughs, where the connectors are shorter in length than the bent struts. In the embodiment of FIG. 43, some of the peaks 106a and troughs 108a of adjacent serpentine circumferential bands 104 overlap one another and are joined one to the other. The overlapping peaks 106a and troughs 108a are longer than the remaining peaks 106 and troughs 108. The regions 130 of overlap between adjacent bands extend in a direction oblique to the longitudinal axis of the stent. The region may also extend in a circumferential direction or in a longitudinal direction. Examples of overlap regions 130 extending in these directions are shown in FIGS. 30 and 38.

The invention is also directed to a stent such as that shown in FIG. 30, comprising a plurality of serpentine circumferential bands 104. Each serpentine circumferential band 104 comprises a plurality of peaks 106 and troughs 108 which are connected by bent struts 110. Adjacent serpentine circumferential bands 104 are connected one to the other in one or more regions 130 of overlap where a peak 106a in one serpentine band overlaps with a trough 108a in an adjacent serpentine circumferential band. The one or more regions 130 of overlap extending in a longitudinal direction.

Optionally, at least one serpentine circumferential bands 104 will be of a greater total circumferential length than other of the serpentine circumferential bands 104. In the embodiment of FIG. 30, the proximal-most and distal-most serpentine circumferential bands 104a are of shorter total circumferential length than the remaining serpentine circumferential bands 104b of the stent.

The invention is also directed to a stent, as shown by way of example in FIG. 37, comprising a plurality of serpentine circumferential bands 104 where each serpentine circumferential band 104 comprises a plurality of peaks 106 and troughs 108. Adjacent peaks 106 and troughs 108 are connected by nested bent struts 110. Serpentine circumferential bands 104 which are adjacent one another are connected via a plurality of connections 130. The stent includes two serpentine circumferential bands which are connected via a first number of connections and two serpentine circumferential bands which are connected via a second number of connections, where the second number is different from the first number.

Figure 25:
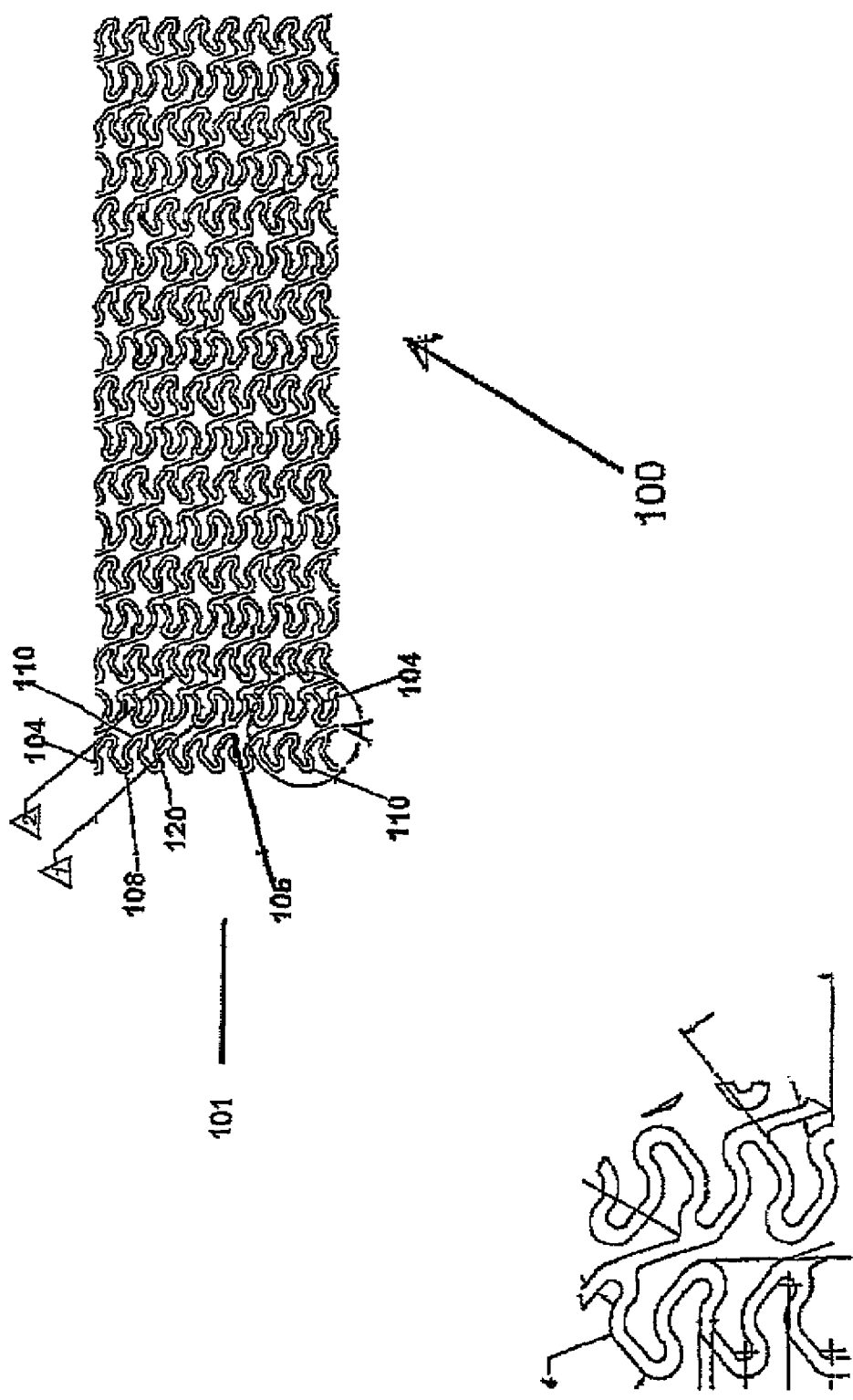

The connections may be in the form of overlapping regions 130 of peaks 106a and troughs 108a on adjacent serpentine circumferential bands 104 or may be form of linear segments extending from one serpentine circumferential band to another serpentine circumferential band. An example of the latter connectors is shown in FIG. 25.

Typically, the stent will have twice as many of the first number of connections as compared to the second number of connections. In the embodiment of FIG. 37, six connections are provided between the proximal-most serpentine circumferential band 104a and the serpentine circumferential band 104b adjacent thereto and six connections are provided between the distal-most serpentine circumferential band 104c and the serpentine circumferential band 104b adjacent thereto. The remainder of the adjacent serpentine circumferential bands 104b have three connections. Other numbers of connections are also within the scope of the invention. By way of example, the proximal-most serpentine circumferential band and the serpentine circumferential band adjacent thereto and/or the distal-most serpentine circumferential band and the serpentine circumferential band adjacent thereto may have four five, six or more connections and the remainder of the serpentine circumferential bands may have three connections.

The stents may optionally be constructed such that at least one of the proximal-most serpentine circumferential band and the distal-most serpentine circumferential band is of a different total circumferential length than other of the serpentine circumferential bands. Typically, the proximal-most and/or distal-most serpentine circumferential bands will be shorter in total circumferential length than the remaining bands. Moreover, the proximal-most serpentine circumferential band may be of a different total length than the distal-most serpentine circumferential band.

The invention is also directed to a stent such as that shown by way of example in FIG. 37 comprising a plurality of adjacent serpentine circumferential bands 104 containing alternating troughs 108 and peaks 106. Adjacent serpentine circumferential bands 104 have a plurality of cells 136 therebetween. At least two adjacent serpentine circumferential bands 104 have a plurality of first cells 136a therebetween and a plurality of second cells 136b therebetween. The second cells 136b are larger than the first cells 136a. Desirably the first and second cells 136a,b alternate with one another about the circumference of the stent. Optionally, as shown in FIG. 37, at least two adjacent serpentine circumferential bands 104 at the proximal end of the stent have a plurality of first cells 136a therebetween and a plurality of second cells 136b therebetween, the second cells 136b larger than the first cells 136a and at least two adjacent serpentine circumferential bands 104 at the distal end of the stent have a plurality of first cells 136a therebetween and a plurality of second cells 136b therebetween, the second cells 136b larger than the first cells 136a. Desirably, the second cells 136b are at least approximately twice the area of the first cells 136a. In the embodiment of FIG. 37, the first cells 136a are bounded at one end by one peak 106 and at another end by one trough 108.

In some embodiments of the invention, circumferentially adjacent struts are not parallel to one another. In the embodiments of FIGS. 40 and 43, for example, as shown in inset A, bent struts 110 comprise first region 110a and second region 110b joined by elbow 110c. First region 110a is longer than second region 110b. Each first region 110a is at an angle α (or 180−α depending on whether first region inclines toward the distal end of the stent or declines toward the distal end of the stent) relative to the longitudinal axis of stent and each second second region 110*b* is at an angle β relative to the longitudinal axis of the stent (or 180–β depending on whether the second region declines toward the distal end of the stent or inclines toward the distal end of the stent). Elbow 110*c* subtends an angle y given by 180–α–β. Desirably, α and β are chosen such that elbow 110*c* subtends an angle γ between about 5 degrees and 90 degrees.

Each peak 104 of the stent has a first region 110*a* of one bent strut and a second region 110*b* of a second bent strut extending therefrom. First region 110*a* and second region 110*b* extending from the peak are non-parallel to one another. Each trough 106 of the stent has a first region 110*a* of one bent strut and a second region 110*b* of a second bent strut extending therefrom. First region 110*a* and second region 110*b* extending from the trough are non-parallel to one another as well.

Because of the difference in length of the first and second regions and the angles of the first and second regions, adjacent inflection points 110*d* of elbows 110*c* on a given circumferential band are staggered slightly in a longitudinal direction as the circumference of the stent is traversed.

These features allow for improved crimpability of the stent.

Desirably, the angle y of the elbow regions of the inventive stents remains constant on expansion of the stent and is substantially the same in the expanded state as it is in the unexpanded state. This feature contributes to compression resistance of the stent.

The invention is also directed to a stent comprising a plurality of serpentine circumferential bands including a first serpentine circumferential band comprising a plurality of peaks and troughs, adjacent peaks and troughs connected by bent struts and a second serpentine circumferential band comprising a plurality of peaks and troughs, adjacent peaks and troughs connected by relatively straight struts. The first and second serpentine circumferential bands are connected to one another. Desirably, the first and second serpentine circumferential bands are connected one to the other via a plurality of connectors which optionally are straight and optionally non-parallel to the longitudinal axis of the stent. Typically, the connectors will extend from peaks on the first serpentine circumferential bands to peaks on the second serpentine circumferential band.

An example of such a stent is shown at 100 in FIG. 19. The stent of FIG. 19 comprises a plurality of the first serpentine circumferential bands and a plurality of the second serpentine circumferential bands where serpentine circumferential bands which are adjacent one another are connected one to the other. In the stent of FIG. 19. the first and second serpentine circumferential bands alternate with one another over the length of the stent.

Any of the inventive stents disclosed above may be provided with a uniform diameter or may taper in portions or along the entire length of the stent. Also, the width and/or thickness of the various portions of the inventive stents may increase or decrease along a given portion of the stent. For example, the width and/or thickness of the circumferential bands and/or connectors may increase or decrease along portions of the stent or along the entire length of the stent. The amplitude and wavelength of several successive first circumferential bands may remain constant while the width and/or thickness of the successive first circumferential bands decrease. Similarly, the amplitude and wavelength of several successive second circumferential bands may remain constant while the width and/or thickness of the successive second circumferential bands decrease.

The inventive stents may also be provided with end effects by modifying the stent such that that one or both ends are more rigid or more flexible than the remainder of the stent. Any of the inventive stents disclosed herein may be modified to have proximal-most and/or distal-most circumferential bands of a greater total circumferential length than the remaining circumferential bands. Any of the inventive stents disclosed herein may also be modified to have proximal-most and/or distal-most circumferential bands of a lesser total circumferential length than the remaining circumferential bands. Moreover, any of the inventive stents disclosed herein may also be modified so that one of the ends has circumferential bands of a lesser total circumferential length than the circumferential band of the other end which in turn is longer or shorter than the total length of any of the remaining circumferential bands.

Also, one or both of the end circumferential bands may be modified to be of a greater longitudinal extent than the remaining circumferential bands or to be of a lesser longitudinal extent than the remaining circumferential bands. Each of the two end circumferential bands may differ in longitudinal extent with one another and with the remaining circumferential bands.

The invention also contemplates modifying the ends of any of the inventive stents so that the two proximal-most and/or two distal-most circumferential bands have more connections therebetween than the remaining circumferential bands or fewer connections therebetween than the remaining circumferential bands.

Further, the proximal-most and/or distal-most circumferential bands may be of a greater mass than the remaining bands or a lower mass than the remaining bands. They may be thicker than the remaining bands or thinner than the remaining bands.

It is understood that the above discussed modifications resulting in end effects may be applied to multiple circumferential bands at one or both ends of the stent and are not limited to the proximal-most and distal-most circumferential bands.

Figure 46:
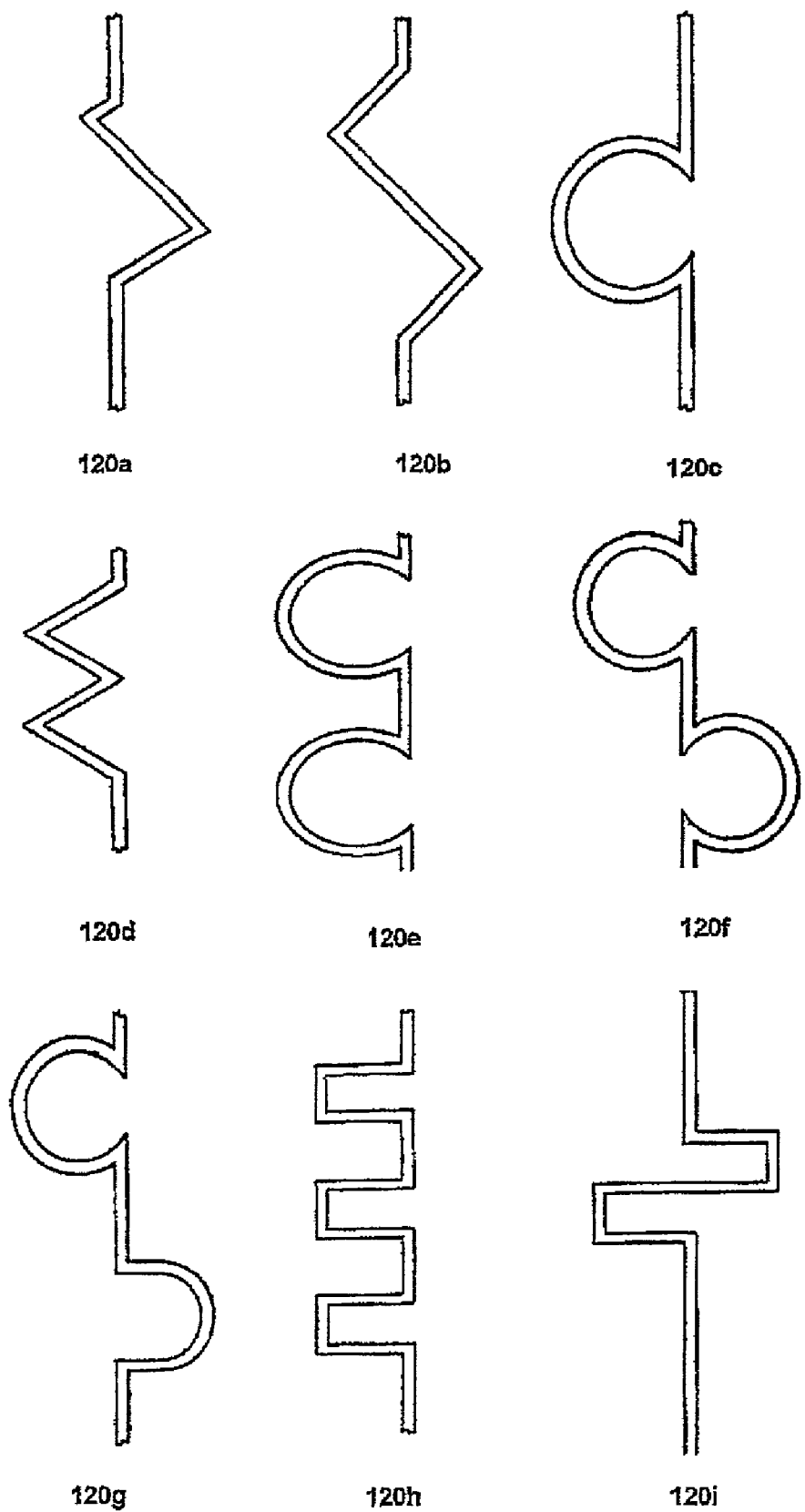
FIG. 46 shows other connectors which may be used in the inventive stents.

The stents disclosed herein may also be modified by employing different types of connections between the circumferential bands. To that end, any of the connectors and connector configurations disclosed herein may be used in any of the disclosed embodiments. For example, in those embodiments in which adjacent circumferential bands overlap, the stent may be modified so that the adjacent circumferential bands do not overlap and are connected by connectors extending between the circumferential bands. Any of the connectors and connector configurations may be used. Other shaped connectors may also be used including those shown at 120*a-i* in FIG. 46. As shown in FIG. 46, the connectors may have one or more bends therein. The connectors may extend from peaks to troughs, from peaks to peaks, from troughs to peaks and/or from troughs to troughs. The connectors may be longer than the individual circumferential bands, which may, but need to occur with connectors with bends therein or they may be shorter than the individual segments.

The stents disclosed herein may also be modified by changing the number of connections between adjacent circumferential bands. Thus, where larger cells are desired, fewer connections between circumferential bands will be provided. Where smaller cells are desired, more connections between bands will be provided. Any of the embodiments shown may also be modified in some portions of the stent but not others. Thus, some sections of the stent may have more connections and other sections may have fewer connections. More flexibility may be achieved by providing fewer connections between adjacent circumferential bands.

The connectors may range on width from being wider than the width of the widest struts in the stent, to being narrower than the narrowest struts in the stent or anywhere inbetween. Regions of different flexibility may also be achieved by using wider connection in some regions, for example the one or both of the ends of the stent and narrower connectors in the other regions of the stent (e.g. the middle) or vice versa.

The invention also contemplates embodiments in which the spacing between adjacent circumferential bands varies in different portions of the stent. For example, the proximal-most circumferential band and/or the distal-most circumferential band may be spaced further apart from the circumferential bands adjacent thereto or may space closer thereto. This would result in using longer connectors between the end bands or shorter connectors, depending on the configuration. In one embodiment, both the proximal-most and the distal-most circumferential bands are more closely spaced to adjacent circumferential bands than the spacing between the remaining circumferential bands and further, the spacing between the proximal-most circumferential band and the circumferential band adjacent thereto differs from the spacing between the distal-most circumferential band and the circumferential band adjacent thereto.

It is also within the scope of the invention for any of the stent disclosed herein to have connectors extending from regions other than peaks and trough or corners of peaks and troughs. For example, the connectors may extend from positions midway between adjacent peaks and troughs, from position one quarter of the way between peaks and troughs, from positions three quarters of the way between peaks and troughs or anywhere else between peaks and troughs.

As shown in the various embodiments, the connections between circumferential bands may extend in a longitudinal direction or may have first and second ends which are circumferentially and longitudinally offset from one another, as in the case of connections extending at an oblique angle. The connections may also include portions which are non-parallel to the longitudinal axis of the stent.

Figure 24:
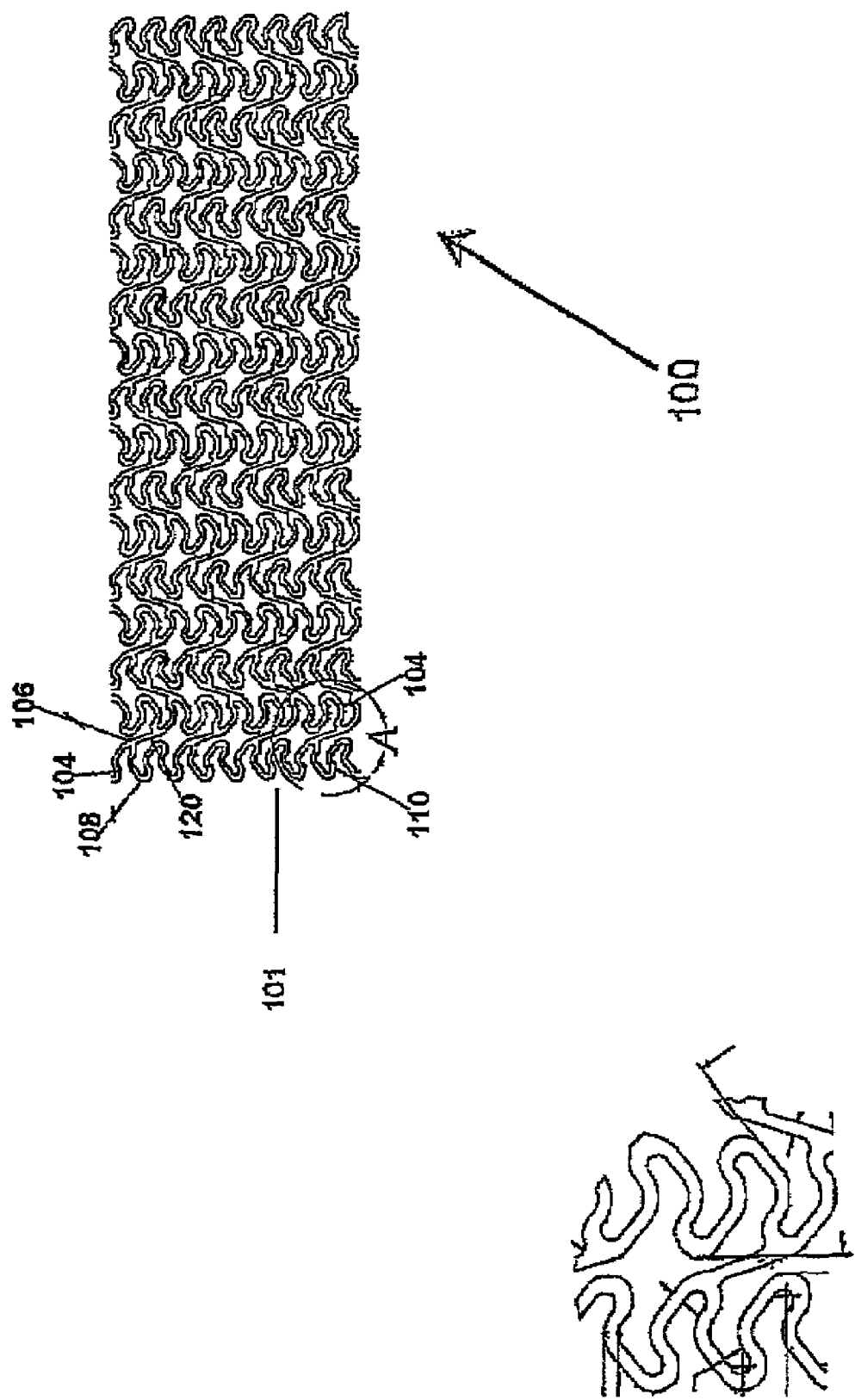

The 'phase relationship' between adjacent circumferential bands may also be modified in any of the embodiments. For example, in embodiments of the invention such as that of FIG. 24, peaks of adjacent cylindrical bands may be in longitudinal alignment with one another or may be unaligned with one another in the longitudinal direction. Similarly, peaks on one band may be longitudinally aligned with troughs on an adjacent circumferential band or may be unaligned with troughs on an adjacent circumferential band. Some of the adjacent circumferential bands may be aligned while other adjacent bands may not be aligned.

Bent struts as referred to herein typically have two segments joined by a bent portion. The segments are straight as shown in the figures but may also be curved, The bent struts may be modified to have more than one bend. For example, a strut having three or more segments and two or more bends may also be used. More generally, substantially bow shaped struts may be used.

The stent patterns disclosed herein may also be used for bifurcated stents. One or more legs and/or the trunk of a bifurcated stent may be provided with any of the stent designs disclosed herein.

The inventive stents may be manufactured using known stent manufacturing techniques. Suitable methods for manufacturing the inventive stents include laser cutting, chemical etching or stamping of a tube. The inventive stents may also be manufactured by laser cutting, chemically etching, stamping a flat sheet, rolling the sheet and, optionally, welding the sheet. Other suitable manufacturing techniques include electrode discharge machining or molding the stent with the desired design.

The stent may also be manufactured by welding individual sections, for example, circumferential bands, together. Any other suitable stent manufacturing process may also be used.

Any suitable stent material may be used in the manufacture of the inventive stents. Examples of such materials include polymeric materials, metals, ceramics and composites. Suitable polymeric materials include thermotropic liquid crystal polymers (LCP's). Where the stent is made of metal, the metal may be stainless steel, cobalt chrome alloys such as elgiloy, tantalum or other plastically deformable metals. Other suitable metals include shape-memory metals such as nickel-titanium alloys generically known as "nitinol", platinum/tungsten alloys and titanium alloys.

The invention also contemplates the use of more than one material in the inventive stents. For example, the first undulating bands and the second undulating bands may be made of different materials. Optionally, the connectors may be made of a different material than the first and/or second undulating bands.

The inventive stents may be provided in mechanically expandable form, in self-expanding form or as a hybrid of the two. Mechanically expandable stents, in accordance with the invention, may be expanded using any suitable mechanical device including a balloon.

The inventive stents may include suitable radiopaque coatings. For example, the stents may be coated with gold or other noble metals or sputtered with tantalum or other metals. The stents may also be made directly from a radiopaque material to obviate the need for a radiopaque coating or may be made of a material having a radiopaque inner core. Other radiopaque metals which may be used include platinum, platinum-tungsten, palladium, platinum-iridium, rhodium, tantalum, or alloys or composites of these metals.

The inventive stents may also be provided with various bio-compatible coatings to enhance various properties of the stent. For example, the inventive stents may be provided with lubricious coatings. The inventive stents may also be provided with drug-containing coatings which release drugs over time. The increased surface area of a stent having bent struts provides for increased drug coatability. The bent struts also provide for point contact with a crimper versus strut/strut contact. Less contact with the crimper results in less disruption of the drug coating.

The inventive stents may also be provided with a sugar or more generally a carbohydrate and/or a gelatin to maintain the stent on a balloon during delivery of the stent to a desired bodily location. Other suitable compounds for treating the stent include biodegradable polymers and polymers which are dissolvable in bodily fluids. Portions of the interior and/or exterior of the stent may be coated or impregnated with the compound. Mechanical retention devices may also be used to maintain the stent on the balloon during delivery. To that end, the use of other coatings on the inventive stents is also within the scope of the invention.

The coating may comprise one or more non-genetic therapeutic agents, genetic materials and cells and combinations thereof as well as other polymeric coatings.

Non-genetic therapeutic agents include anti-thrombogenic agents such as heparin, heparin derivatives, urokinase, and PPack (dextrophenylalanine proline arginine chloromethylketone); anti-proliferative agents such as enoxaprin, angiopeptin, or monoclonal antibodies capable of blocking smooth muscle cell proliferation, hirudin, and acetylsalicylic acid;

anti-inflammatory agents such as dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine, and ropivacaine; anti-coagulants such as D-Phe-Pro-Arg chloromethyl keton, an RGD peptide-containing compound, heparin, antithrombin compounds, platelet receptor antagonists, anti-thrombin anticodies, anti-platelet receptor antibodies, aspirin, prostaglandin inhibitors, platelet inhibitors and tick antiplatelet peptides; vascular cell growth promotors such as growth factor inhibitors, growth factor receptor antagonists, transcriptional activators, and translational promotors;

vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; and agents which interfere with endogenous vascoactive mechanisms.

Genetic materials include anti-sense DNA and RNA, DNA coding for, anti-sense RNA, tRNA or rRNA to replace defective or deficient endogenous molecules, angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin like growth factor, cell cycle inhibitors including CD inhibitors, thymidine kinase ("TK") and other agents useful for interfering with cell proliferation the family of bone morphogenic proteins ("BMP"s"),BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Desirable BMP"s are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNA"s encoding them.

Cells can be of human origin (autologous or allogeneic) or from an animal source (xenogeneic), genetically engineered if desired to deliver proteins of interest at the transplant site. The cells may be provided in a delivery media. The delivery media may be formulated as needed to maintain cell function and viability.

Suitable polymer coating materials include polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as EVA, polyvinyl ethers, polyvinyl aromatics, polyethylene oxides, glycosaminoglycans, polysaccharides, polyesters including polyethylene terephthalate, polyacrylamides, polyethers, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof, coatings from polymer dispersions such as polyurethane dispersions (for example, BAYHDROL®), fibrin, collagen and derivatives thereof, polysaccharides such as celluloses, starches, dextrans, alginates and derivatives, hyaluronic acid, squalene emulsions. Polyacrylic acid, available as HYDROPLUS® (Boston Scientific Corporation, Natick, Mass.), and described in U.S. Pat. No. 5,091,205, the disclosure of which is hereby incorporated herein by reference, is particularly desirable. Even more desirable is a copolymer of polylactic acid and polycaprolactone.

The inventive stents may also be used as the framework for a graft. Suitable coverings include nylon, collagen, PTFE and expanded PTFE, polyethylene terephthalate and KEVLAR, or any of the materials disclosed in U.S. Pat. Nos. 5,824,046 and 5,755,770. More generally, any known graft material may be used including synthetic polymers such as polyethylene, polypropylene, polyurethane, polyglycolic acid, polyesters, polyamides, their mixtures, blends and copolymers.

The inventive stents may find use in coronary arteries, renal arteries, peripheral arteries including iliac arteries, arteries of the neck and cerebral arteries. The stents of the present invention, however, are not limited to use in the vascular system and may also be advantageously employed in other body structures, including but not limited to arteries, veins, biliary ducts, urethras, fallopian tubes, bronchial tubes, the trachea, the esophagus, the prostate and the bowels.

Suitable stent delivery devices such as those disclosed in U.S. Pat. Nos. 6,123,712, 6,120,522 and 5,957,930 may be used to deliver the inventive stents to the desired bodily location. The choice of delivery device will depend on whether a self-expanding or balloon expandable stent is used. The inventive stents may be delivered in conjunction with one or more stent retaining sleeves. An example of stent retaining sleeves is disclosed in U.S. provisional application No. 60/238,178.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to".

Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below (e.g. claim 3 may be taken as alternatively dependent from claim 1; claim 4 may be taken as alternatively dependent on claim 3, or on claim 1, claim 5 may be taken as alternatively dependent on claim 4, claim 3, or on claim 1; etc.).

The disclosure is intended to be illustrative and not exhaustive. This description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

The invention claimed is:

1. A stent comprising a plurality of circumferential bands, each circumferential band forming a closed path about the longitudinal axis of the stent, each circumferential band having a total circumferential length, the total circumferential length being the length of the closed path, circumferential bands which are adjacent one another connected one to the other via a plurality of connectors, the circumferential bands including first circumferential bands characterized by a first number of alternating first peaks and first troughs, each adjacent first peak and first trough being joined by a bent strut and second circumferential bands characterized by a second number of alternating second peaks and second troughs, each adjacent second peak and second trough being joined by a bent strut, the second number different from the first number, each bent strut having a first segment, a second segment and a bent portion, the bent portion extending between the first and second segments and positioned substantially midway between the adjacent peak and trough, each second circumferential band connected to one adjacent first circumferential band via at least one connector, the connector extending from a peak on the adjacent first circumferential band to a peak on the second circumferential band, each second circumferential band connected to another adjacent first circumferential band via at least one connector, the connector extending from a trough on the another first circumferential band to a trough on the second circumferential band.

2. The stent of claim 1 wherein each second circumferential band is connected to one adjacent first circumferential band via a plurality of connectors, the connectors extending from peaks on the adjacent first circumferential band to peaks on the second circumferential band, each second circumferential band connected to another adjacent first circumferential band via a plurality of connectors, the connectors extending from troughs on the another first circumferential band to troughs on the second circumferential band.

3. The stent of claim 2 wherein the connectors are not straight.

4. The stent of claim 2 wherein the connectors are substantially parallel to the bent struts of the first circumferential bands.

5. The stent of claim 2 wherein the first and second circumferential bands are each characterized by a longitudinal extent, the longitudinal extent of each first circumferential band exceeding the longitudinal extent of each second circumferential band.

6. The stent of claim 2 wherein the first circumferential bands are each characterized by a first total circumferential length and the second circumferential bands are each characterized by a second total circumferential length, the first total circumferential length equal to the second total circumferential length.

* * * * *